(12) United States Patent
Richelson et al.

(10) Patent No.: US 8,440,724 B2
(45) Date of Patent: May 14, 2013

(54) INHIBITING NEUROTRANSMITTER REUPTAKE

(75) Inventors: Elliott Richelson, Ponte Vedra Beach, FL (US); Abdul H. Fauq, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 125 days.

(21) Appl. No.: 12/812,337

(22) PCT Filed: Jan. 9, 2009

(86) PCT No.: PCT/US2009/030642
§ 371 (c)(1),
(2), (4) Date: Jul. 9, 2010

(87) PCT Pub. No.: WO2009/089479
PCT Pub. Date: Jul. 16, 2009

(65) Prior Publication Data
US 2010/0280127 A1    Nov. 4, 2010

Related U.S. Application Data

(60) Provisional application No. 61/020,071, filed on Jan. 9, 2008.

(51) Int. Cl.
*A61K 31/135* (2006.01)
(52) U.S. Cl.
USPC ....................................................... 514/649
(58) Field of Classification Search .................. 514/649
See application file for complete search history.

(56) References Cited

U.S. PATENT DOCUMENTS

| 6,069,177 | A | 5/2000 | Carlier et al. |
|---|---|---|---|
| 6,184,222 | B1 | 2/2001 | Heiligenstein |
| 6,700,018 | B2 * | 3/2004 | Richelson et al. ............ 564/363 |
| 6,914,080 | B2 | 7/2005 | Richelson et al. |
| 7,214,826 | B2 | 5/2007 | Richelson et al. |
| 2007/0197662 | A1 | 8/2007 | Richelson et al. |

FOREIGN PATENT DOCUMENTS

| WO | WO02/40006 | 5/2002 |
|---|---|---|
| WO | WO03/007929 | 1/2003 |
| WO | WO2005/120200 | 12/2005 |
| WO | WO2009/089479 | 7/2009 |

OTHER PUBLICATIONS

King, F.D. (Ed.), "Bioisosteres, conformational restriction and prodrugs—case history: an example of a conformational restriction approach," Medical Chemistry: Principles and Practice, 1994, Chapter 14, 206-209.*
Beer et al., "DOV 216,303, a 'triple' reuptake inhibitor: safety, tolerability, and pharmacokinetic profile," *J. Clin. Pharmacol.*, 2004, 44(12):1360-1367.
Bolden-Watson and Richelson, "Blockade by newly-developed antidepressants of biogenic amine uptake into rat brain synaptosomes," *Life Sci.*, 1993, 52:1023-1029.

(Continued)

*Primary Examiner* — Paul Zarek
(74) *Attorney, Agent, or Firm* — Fish & Richardson P.C.

(57) ABSTRACT

This document relates to compounds as well as methods and materials involved in modulating neurotransmitter reuptake. For example, compounds, methods for synthesizing compounds, and methods for inhibiting neurotransmitter reuptake are provided.

9 Claims, 26 Drawing Sheets

3-chloro-N-methyl-2-(naphthalen-2-yl)-3-phenylpropan-1-amine

OTHER PUBLICATIONS

Carlier et al., "Anti-Selective Aldol Reaction of Benzylic Nitriles and Synthesis of γ-Amino Alcohols," *J. Org. Chem.*, 1995, 60:7511-7517.

Carlier et al., "Gamma-Amino Alcohol Wide-Spectrum Reuptake Inhibitor Antidepressant Drug Candidates and Neurochemical Probes," *Proceedings of the Symposium on the Frontiers of Chemistry the Second Conference for Worldwide Chinese Young Chemists (CWCYC-2)*, Dec. 20-23, 1997, Hong Kong, pp. 127-128.

Carlier et al., "Lead Optimization in the Development of SNDRI Antidepressant Drug Candidates and Species-Selective Dopamine Transporter Ligands," *Fifth Chemistry Postgraduate Research Symposium in Hong Kong*, Hong Kong, Apr. 25, 1998, Abstract O-55.

Carlier et al., "Synthesis of a Potent Wide-Spectrum Serotonin-, Norepinephrine-, Dopamine-Reuptake Inhibitor (SNDRI) and a Species-Selective Dopamine-Reuptake Inhibitor Based on the Gamma-Amino Alcohol Functional Group," *Bioorg. Med. Chem. Lett.*, 1998, 8:487-492.

Carlier et al., "HMPA Promotes Retro-Aldol Reaction, Resulting in Syn-Selective Addition of Lithiated 1-Naphthylacetonitrile to Aromatic Aldehdes," *Org. Lett.*, 2000, 2(16):2443-2445.

Chen and Skolnick, "Triple uptake inhibitors: therapeutic potential in depression and beyond," *Exp. Opin. Investig. Drugs*, 2007, 16(9):1365-1377.

Cryan et al., "Assessing antidepressant activity in rodents: recent developments and future needs," *Trends Pharmacol. Sci.*, 2002, 23(5):238-245.

Detke et al., "Active behaviors in the rat forced swimming test differentially produced by serotonergic and noradrenergic antidepressants," *Psychopharmacology*, 1995, 121: 66-72.

Eisensamer et al., "Antidepressants are functional antagonists at the serotonin type 3 (5-HT3) receptor," *Mol. Psychiatry*, 2003, 8(12):994-1007.

Hanna et al., Synthesis of Some Tropane Derivatives of Anticipated Activity on the Reuptake of Norepinephrine and/or Serotonin, *Biorganic and Medicinal Chemistry*, 2007, vol. 15, pp. 7765-7772.

Liang and Richelson, "Triple Reuptake Inhibitors: Next-Generation Antidepressants," *Primary Psychiatry*, 2008, 15(4):50-56.

Liang et al., "Antidepressant-Like Pharmacological Profile of a Novel Triple Reuptake Inhibitor, ($1S,2S$)-3-(Methylamino)-2-(naphthalen-2-yl)-1-phenylpropan-1-ol (PRC200-Ss)," *J. Pharmacol. Exp. Ther.*, 2008, 327(2):573-583.

Lo et al., "Anti-Selective Aldol of Benzylic Nitriles and Synthesis of γ-Hydroxyamine Antidepressant Analogs," *Second Symposium on Chemistry Postgraduate Research in Hong Kong*, Hong Kong, Mar. 11, 1995, Abstract OP-5.

Lowry et al., "Protein Measurement with the Folin Phenol Reagent," *J. Biol. Chem.*, 1951, 193:265-275.

May, "Alfred Burger Award address. A Half Century in Medicinal Chemistry with Major Emphasis on Pain-RelievingDrugs and Their Antagonists," *J. Med. Chem.*, 1992, 35(20):3587-3594.

Munson and Rodbard, "LIGAND: A Versatile Computerized Approach for Characterization of Ligand-Binding Systems," *Analyt. Biochem.*, 1980, 107:220-239.

Pacholczyk et al., "Expression cloning of a cocaine-and antidepressant-sensitive human noradrenaline transporter," *Nature*, 1991, 350:350-354.

Pfenning and Richelson, "Methods for Studying Receptors with Cultured Origin," *Methods in Neurotransmitter Receptor Analysis*, 1990, Raven Cells of Nervous Tissue Press, New York, pp. 147-175.

Popik et al., "Pharmacological Profile of the "Triple" Monoamine Neurotransmitter Uptake Inhibitor, DOV 102,677," *Cell. Mol. Neurobiol.*, 2006, 26:857-873.

Porsolt et al., "Depression: a new animal model sensitive to antidepressant treatments," *Nature*, 1977, 266:730-732.

Pristupa et al., "Pharmacological Heterogeneity of the Cloned and Native Human Dopamine Transporter: Disassociation of [3H]WIN 35, 428 and [3H]GBR 12,935 Binding." *Mol. Pharmacol.*, 1994, 45:125-135.

Ramamoorthy et al., "Antidepressant- and cocaine-sensitive human serotonin transporter: Molecular cloning, expression, and chromosomal localization," *Proc. Natl. Acad. Sci. USA*, 1993, 90:2542-2546.

Richelson and Pfenning, "Blockade by antidepressants and related compounds of biogenic amine uptake into rat brain synaptosomes: Most antidepressants selectively block norepinephrine uptake," *Eur. J. Pharmacol.*, 1984, 104:277-286.

Richelson et al., "A novel series of triple re-uptake inhibitor potential antidepressants," *IXth World Conference on Clinical Pharmacology and Therapeutics*, Quebec City, Canada, Jul. 30, 2008, Abstract 386.

Richelson et al., in "Methods in Neurotransmitter Receptor Analysis" Yamamura et al., Eds.; New York, Raven Press, 1990, pp. 147-175.

Richelson, "Triple reuptake inhibitors as a new generation of antidepressant drugs," *J. Affect Disord.*, 2008, 107 (Suppl 1):S36. (International Society for Affective Disorders, Cape Town, SA, Mar. 16, 2008).

Shaw et al., "Antidepressant-like effects of novel triple reuptake Inhibitors, PRCO25 and PRC050," *Eur. J. Pharmacol.*, 2007, 555:30-36.

Shaw et al., "Antidepressant-like effects of PRC200, a novel norepinephrine, serotonin, and dopamine reuptake inhibitor," *Biol. Psychiatry*, 2006, 59(8):61S-62S, Abstract 196.

Shaw et al., "Reuptake inhibitors," *Current Psychiatry*, 2007, 6(3):31-42.

Skolnick et al., "Antidepressant-like actions of DOV 21,947: a "triple" reuptake inhibitor," *Eur. J. Pharmacol.*, 2003, 461:99-104.

Skolnick et al., "Preclinical and Clinical Pharmacology of DOV 216,303, a "Triple" Reuptake Inhibitor," *CNS Drug Reviews*, 2006, 12(2):123-134.

Steru et al., "The tail suspension test: a new method for screening antidepressants in mice," *Psychopharmacology*, 1985, 85(3):367-370.

Tatsumi et al., "Pharmacological profile of antidepressants and related compounds at human monoamine transporters," *Eur. J. Pharmacol.*, 1997, 340:249-258.

Examination report in European Application No. 05756359.5, mailed May 18, 2009, 4 pages.

Examination report in European Application No. 05756359.5, mailed Sep. 18, 2008, 4 pages.

Supplementary European Search Report in European Application No. 05756359.5, dated Jan. 22, 2008, 3 pages.

Authorized Officer Young Jin Kang. International Search Report and Written Opinion of the International Searching Authority in International Application No. PCT/US2009/030642, mailed Aug. 28, 2009, 9 pages.

Authorized Officer Athina Nickitas-Etienne. International Preliminary Report on Patentability in International Application No. PCT/US2009/030642, issued Jul. 13, 2010, 7 pages.

Authorized Officer Samuel A. Barts. International Preliminary Examination Report in International Application No. PCT/US02/22069, completed Nov. 13, 2003, 3 pages.

Authorized Officer Samuel A. Barts. International Search Report in International Application No. PCT/US02/22069, mailed Dec. 9, 2002, 1 page 2003, 3 pages.

International Search Report and Written Opinion in International Application No. PCT/US05/019866, mailed May 24, 2007, 8 pages.

International Preliminary Report on Patentability in International Application No. PCT/US05/019866, mailed Jun. 28, 2007, 5 pages.

International Preliminary Report on Patentability in International Application No. PCT/US2010/055065, mailed May 18, 2012, 10 pages.

International Search Report and Written Opinion in International Application No. PCT/US2010/055065, mailed Jul. 26, 2011, 14 pages.

* cited by examiner 3-chloro-N-methyl-2-(naphthalen-2-yl)-3-phenylpropan-1-amine (2R,3R)-3-chloro-N-methyl-2-(naphthalen-2-yl)-3-phenylpropan-1-amine (2S,3R)-3-chloro-N-methyl-2-(naphthalen-2-yl)-3-phenylpropan-1-amine (2S,3S)-3-chloro-N-methyl-2-(naphthalen-2-yl)-3-phenylpropan-1-amine (2R,3S)-3-chloro-N-methyl-2-(naphthalen-2-yl)-3-phenylpropan-1-amine 3-fluoro-N-methyl-2-(naphthalen-2-yl)-3-phenylpropan-1-amine (2R,3R)-3-fluoro-N-methyl-2-(naphthalen-2-yl)-3-phenylpropan-1-amine (2S,3R)-3-fluoro-N-methyl-2-(naphthalen-2-yl)-3-phenylpropan-1-amine (2S,3S)-3-fluoro-N-methyl-2-(naphthalen-2-yl)-3-phenylpropan-1-amine (2R,3S)-3-fluoro-N-methyl-2-(naphthalen-2-yl)-3-phenylpropan-1-amine 3-azido-N-methyl-2-(naphthalen-2-yl)-3-phenylpropan-1-amine (2R,3R)-3-azido-N-methyl-2-(naphthalen-2-yl)-3-phenylpropan-1-amine (2S,3R)-3-azido-N-methyl-2-(naphthalen-2-yl)-3-phenylpropan-1-amine (2S,3S)-3-azido-N-methyl-2-(naphthalen-2-yl)-3-phenylpropan-1-amine (2R,3S)-3-azido-N-methyl-2-(naphthalen-2-yl)-3-phenylpropan-1-amine N1-methyl-2-(naphthalen-2-yl)-3-phenylpropane-1,3-diamine (2R,3R)-N1-methyl-2-(naphthalen-2-yl)-3-phenylpropane-1,3-diamine (2S,3R)-N1-methyl-2-(naphthalen-2-yl)-3-phenylpropane-1,3-diamine (2S,3S)-N1-methyl-2-(naphthalen-2-yl)-3-phenylpropane-1,3-diamine (2R,3S)-N1-methyl-2-(naphthalen-2-yl)-3-phenylpropane-1,3-diamine 3-(methylamino)-2-(naphthalen-2-yl)-1-phenylpropyl acetate (2R,3R)-3-(methylamino)-2-(naphthalen-2-yl)-1-phenylpropyl acetate (2S,3R)-3-(methylamino)-2-(naphthalen-2-yl)-1-phenylpropyl acetate (2S,3S)-3-(methylamino)-2-(naphthalen-2-yl)-1-phenylpropyl acetate (2R,3S)-3-(methylamino)-2-(naphthalen-2-yl)-1-phenylpropyl acetate 3-methoxy-N-methyl-2-(naphthalen-2-yl)-3-phenylpropan-1-amine (2R,3R)-3-methoxy-N-methyl-2-(naphthalen-2-yl)-
3-phenylpropan-1-amine (2S,3R)-3-methoxy-N-methyl-2-(naphthalen-2-yl)-
3-phenylpropan-1-amine (2S,3S)-3-methoxy-N-methyl-2-(naphthalen-2-yl)-
3-phenylpropan-1-amine (2R,3S)-3-methoxy-N-methyl-2-(naphthalen-2-yl)-
3-phenylpropan-1-amine 1-methyl-5-(naphthalen-2-yl)-4-phenylhexahydropyrimidine (2R,3R)-1-methyl-5-(naphthalen-2-yl)-
4-phenylhexahydropyrimidine (2S,3R)-1-methyl-5-(naphthalen-2-yl)-
4-phenylhexahydropyrimidine (2S,3S)-1-methyl-5-(naphthalen-2-yl)-
4-phenylhexahydropyrimidine (2R,3S)-1-methyl-5-(naphthalen-2-yl)-
4-phenylhexahydropyrimidine N1,N1-dimethyl-2-(naphthalen-2-yl)-3-phenylpropane-1,3-diamine (2R,3R)-N1,N1-dimethyl-2-(naphthalen-2-yl)-
3-phenylpropane-1,3-diamine (2S,3R)-N1,N1-dimethyl-2-(naphthalen-2-yl)-
3-phenylpropane-1,3-diamine (2S,3S)-N1,N1-dimethyl-2-(naphthalen-2-yl)-
3-phenylpropane-1,3-diamine (2R,3S)-N1,N1-dimethyl-2-(naphthalen-2-yl)-
3-phenylpropane-1,3-diamine Dimer of 3-(methylamino)-2-(naphthalen-2-yl)-1-phenylpropan-1-ol (2R,3R)-3-(methylamino)-2-(naphthalen-2-yl)-1-phenylpropan-1-ol (2S,3S)-3-(methylamino)-2-(naphthalen-2-yl)-1-phenylpropan-1-ol (2S,3R)-3-(methylamino)-2-(naphthalen-2-yl)-1-phenylpropan-1-ol (2*R*,3*S*)-3-(methylamino)-2-(naphthalen-2-yl)-1-phenylpropan-1-ol Tail-Suspension Test in Mice Locomotor Activity Dimer of 3,3'-(butane-1,4diylbis(oxy))bis(N-methyl-2-(naphthalen-2-yl)-3-phenylpropan-1-amine)

(2R,2'R,3R,3'R)-3,3'-(butane-1,4-diylbis(oxy)bis(N-methyl-2-(naphthalen-2-yl)-1-phenylpropan-1-amine)

(2S,2'S,3S,3'S)-3,3'-(butane-1,4-diylbis(oxy)bis(N-methyl-2-(naphthalen-2-yl)-1-phenylpropan-1-amine)

(2S,2'S,3R,3'R)-3,3'-(butane-1,4-diylbis(oxy)bis(N-methyl-2-(naphthalen-2-yl)-1-phenylpropan-1-amine)

(2R,2'R,3S,3'S)-3,3'-(butane-1,4-diylbis(oxy)bis(N-methyl-2-(naphthalen-2-yl)-1-phenylpropan-1-amine)

3-methyl-5-(naphthalen-2-yl)-6-phenyl-1,3-oxazinane (5R,6R)-3-methyl-5-(naphthalen-2-yl)-
6-phenyl-1,3-oxazinane (5S,6R)-3-methyl-5-(naphthalen-2-yl)-
6-phenyl-1,3-oxazinane (5S,6S)-3-methyl-5-(naphthalen-2-yl)-
6-phenyl-1,3-oxazinane (5R,6S)-3-methyl-5-(naphthalen-2-yl)-
6-phenyl-1,3-oxazinane 1,1-dimethyl-5-(naphthalen-2-yl)-4-phenylhexahydropyrimidin-1-ium chloride (4R,5R)-1,1-dimethyl-5-(naphthalen-2-yl)-
4-phenylhexahydropyrimidin-1-ium chloride (4R,5S)-1,1-dimethyl-5-(naphthalen-2-yl)-
4-phenylhexahydropyrimidin-1-ium chloride (4S,5S)-1,1-dimethyl-5-(naphthalen-2-yl)-
4-phenylhexahydropyrimidin-1-ium chloride (4S,5R)-1,1-dimethyl-5-(naphthalen-2-yl)-
4-phenylhexahydropyrimidin-1-ium chloride 5-(naphthalen-2-yl)-6-phenyl-1,3-oxazinane (5R,6R)-5-(naphthalen-2-yl)-
6-phenyl-1,3-oxazinane (5S,6R)-5-(naphthalen-2-yl)-
6-phenyl-1,3-oxazinane (5S,6S)-5-(naphthalen-2-yl)-
6-phenyl-1,3-oxazinane (5R,6S)-5-(naphthalen-2-yl)-
6-phenyl-1,3-oxazinane

INHIBITING NEUROTRANSMITTER REUPTAKE

CROSS-REFERENCE TO RELATED APPLICATIONS

This application is a National Stage application under 35 U.S.C. §371 and claims benefit under 35 U.S.C. §119(a) of International Application No. PCT/US2009/030642, having an International Filing Date of Jan. 1, 2009, which claims the benefit of U.S. Provisional Application Ser. No. 61/020,071, filed Jan. 9, 2008. The disclosures of the prior applications are considered part of (and are incorporated by reference in) the disclosure of this application.

BACKGROUND

1. Technical Field

This document relates to compounds as well as methods and materials involved in modulating neurotransmitter reuptake.

2. Background Information

An imbalance of neurotransmitters in the brain can occur when not enough neurotransmitter is made and released from presynaptic cells or the reuptake of neurotransmitters by presynaptic cells is too rapid. If neurotransmitters such as serotonin, norepinephrine, or dopamine are not made and released in effective amounts or are cleared from the synaptic cleft too quickly, then cell-to-cell communication can be affected. Clinical manifestations of such imbalances include depression and anxiety disorders. Serotonin-, norepinephrine-, dopamine-reuptake inhibitors (SNDRIs) represent a class of antidepressant medications that inhibit the reuptake of these neurotransmitters back into presynaptic cells Inhibiting neurotransmitter reuptake can increase the amount of neurotransmitter present in the synapse, thus helping to normalize the transmission of neuronal signals and alleviate the symptoms of depression and anxiety disorders.

SUMMARY

This document relates to compounds as well as methods and materials involved in modulating neurotransmitter reuptake. For example, this document provides compounds (e.g., amine compounds), methods for synthesizing compounds (e.g., amine compounds), and methods for inhibiting neurotransmitter reuptake. The compounds provided herein can be used as antidepressant medications for inhibiting neurotransmitter reuptake and treating anxiety or depressive disorders. In some cases, a compound provided herein can be used to treat major depressive disorder. In addition, the methods provided herein for synthesizing compounds allow for synthesis in a reliable and efficient manner.

In general, one aspect of this document features a composition comprising, or consisting essentially of, 3-chloro-N-methyl-2-(naphthalen-2-yl)-3-phenylpropan-1-amine or a salt thereof. The 3-chloro-N-methyl-2-(naphthalen-2-yl)-3-phenylpropan-1-amine can comprise (2R, 3R)-3-chloro-N-methyl-2-(naphthalen-2-yl)-3-phenylpropan-1-amine or (2S, 3S)-3-chloro-N-methyl-2-(naphthalen-2-yl)-3-phenylpropan-1-amine. The 3-chloro-N-methyl-2-(naphthalen-2-yl)-3-phenylpropan-1-amine can comprise (2R, 3S)-3-chloro-N-methyl-2-(naphthalen-2-yl)-3-phenylpropan-1-amine or (2S, 3R)-3-chloro-N-methyl-2-(naphthalen-2-yl)-3-phenylpropan-1-amine. The 3-chloro-N-methyl-2-(naphthalen-2-yl)-3-phenylpropan-1-amine can comprise: (i) two compounds selected from the group consisting of (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, and (2S, 3R)-3-chloro-N-methyl-2-(naphthalen-2-yl)-3-phenylpropan-1-amine; or (ii) three compounds selected from the group consisting of (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, and (2S, 3R)-3-chloro-N-methyl-2-(naphthalen-2-yl)-3-phenylpropan-1-amine; or (iii) (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, and (2S, 3R)-3-chloro-N-methyl-2-(naphthalen-2-yl)-3-phenylpropan-1-amine. The composition can comprise a pharmaceutically acceptable carrier.

In another aspect, this document features a composition comprising, or consisting essentially of, 3-fluoro-N-methyl-2-(naphthalen-2-yl)-3-phenylpropan-1-amine or a salt thereof. The 3-fluoro-N-methyl-2-(naphthalen-2-yl)-3-phenylpropan-1-amine can comprise (2R, 3R)-3-fluoro-N-methyl-2-(naphthalen-2-yl)-3-phenylpropan-1-amine or (2S, 3S)-3-fluoro-N-methyl-2-(naphthalen-2-yl)-3-phenylpropan-1-amine. The 3-fluoro-N-methyl-2-(naphthalen-2-yl)-3-phenylpropan-1-amine can comprise (2R, 3S)-3-fluoro-N-methyl-2-(naphthalen-2-yl)-3-phenylpropan-1-amine or (2S, 3R)-3-fluoro-N-methyl-2-(naphthalen-2-yl)-3-phenylpropan-1-amine. The 3-fluoro-N-methyl-2-(naphthalen-2-yl)-3-phenylpropan-1-amine can comprise: (i) two compounds selected from the group consisting of (2R, 3R)-3-fluoro-N-methyl-2-(naphthalen-2-yl)-3-phenylpropan-1-amine, (2S, 3S)-3-fluoro-N-methyl-2-(naphthalen-2-yl)-3-phenylpropan-1-amine, (2R, 3S)-3-fluoro-N-methyl-2-(naphthalen-2-yl)-3-phenylpropan-1-amine, and (2S, 3R)-3-fluoro-N-methyl-2-(naphthalen-2-yl)-3-phenylpropan-1-amine; or (ii) three compounds selected from the group consisting of (2R, 3R)-3-fluoro-N-methyl-2-(naphthalen-2-yl)-3-phenylpropan-1-amine, (2S, 3S)-3-fluoro-N-methyl-2-(naphthalen-2-yl)-3-phenylpropan-1-amine, (2R, 3S)-3-fluoro-N-methyl-2-(naphthalen-2-yl)-3-phenylpropan-1-amine, and (2S, 3R)-3-fluoro-N-methyl-2-(naphthalen-2-yl)-3-phenylpropan-1-amine; or (iii) (2R, 3R)-3-fluoro-N-methyl-2-(naphthalen-2-yl)-3-phenylpropan-1-amine, (2S, 3S)-3-fluoro-N-methyl-2-(naphthalen-2-yl)-3-phenylpropan-1-amine, (2R, 3S)-3-fluoro-N-methyl-2-(naphthalen-2-yl)-3-phenylpropan-1-amine, and (2S, 3R)-3-fluoro-N-methyl-2-(naphthalen-2-yl)-3-phenylpropan-1-amine. The composition can comprise a pharmaceutically acceptable carrier.

In another aspect, this document features a composition comprising, or consisting essentially of, 3-azido-N-methyl-2-(naphthalen-2-yl)-3-phenylpropan-1-amine or a salt thereof. The 3-azido-N-methyl-2-(naphthalen-2-yl)-3-phenylpropan-1-amine can comprise (2R, 3R)-3-azido-N-methyl-2-(naphthalen-2-yl)-3-phenylpropan-1-amine or (2S, 3S)-3-azido-N-methyl-2-(naphthalen-2-yl)-3-phenylpropan-1-amine. The 3-azido-N-methyl-2-(naphthalen-2-yl)-3-phenylpropan-1-amine can comprise (2R, 3S)-3-azido-N-methyl-2-(naphthalen-2-yl)-3-phenylpropan-1-amine or (2S, 3R)-3-azido-N-methyl-2-(naphthalen-2-yl)-3-phenylpropan-1-amine. The 3-azido-N-methyl-2-(naphthalen-2-yl)-3-phenylpropan-1-amine can comprise: (i) two compounds selected from the group consisting of (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2- yl)-3-phenylpropan-1-amine, and (2S, 3R)-3-azido-N-methyl-2-(naphthalen-2-yl)-3-phenylpropan-1-amine; or (ii) three compounds selected from the group consisting of (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine; or (iii) (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine. The composition can comprise a pharmaceutically acceptable carrier.

In another aspect, this document features a composition comprising, or consisting essentially of, N1-methyl-2-(naphthalen-2-yl)-3-phenylpropane-1,3-diamine or a salt thereof. The N1-methyl-2-(naphthalen-2-yl)-3-phenylpropane-1,3-diamine can comprise (2R, 3R)—N1-methyl-2-(naphthalen-2-yl)-3-phenylpropane-1,3-diamine or (2S, 3S)—N1-methyl-2-(naphthalen-2-yl)-3-phenylpropane-1,3-diamine. The N1-methyl-2-(naphthalen-2-yl)-3-phenylpropane-1,3-diamine can comprise (2R, 3S)—N1-methyl-2-(naphthalen-2-yl)-3-phenylpropane-1,3-diamine or (2S, 3R)-3-N1-methyl-2-(naphthalen-2-yl)-3-phenylpropane-1,3-diamine. The N1-methyl-2-(naphthalen-2-yl)-3-phenylpropane-1,3-diamine can comprise: (i) two compounds selected from the group consisting of (2R, 3R)—N1-methyl-2-(naphthalen-2-yl)-3-phenylpropane-1,3-diamine, (2S, 3S)—N1-methyl-2-(naphthalen-2-yl)-3-phenylpropane-1,3-diamine, (2R, 3S)—N1-methyl-2-(naphthalen-2-yl)-3-phenylpropane-1,3-diamine, and (2S, 3R)—N1-methyl-2-(naphthalen-2-yl)-3-phenylpropane-1,3-diamine; or (ii) three compounds selected from the group consisting of (2R, 3R)—N1-methyl-2-(naphthalen-2-yl)-3-phenylpropane-1,3-diamine, (2S, 3S)—N1-methyl-2-(naphthalen-2-yl)-3-phenylpropane-1,3-diamine, (2R, 3S)—N1-methyl-2-(naphthalen-2-yl)-3-phenylpropane-1,3-diamine, and (2S, 3R)—N1-methyl-2-(naphthalen-2-yl)-3-phenylpropane-1,3-diamine; or (iii) (2R, 3R)—N1-methyl-2-(naphthalen-2-yl)-3-phenylpropane-1,3-diamine, (2S, 3S)—N1-methyl-2-(naphthalen-2-yl)-3-phenylpropane-1,3-diamine, (2R, 3S)—N1-methyl-2-(naphthalen-2-yl)-3-phenylpropane-1,3-diamine, and (2S, 3R)—N1-methyl-2-(naphthalen-2-yl)-3-phenylpropane-1,3-diamine. The composition can comprise a pharmaceutically acceptable carrier.

In another aspect, this document features a composition comprising, or consisting essentially of, 3-(methylamino)-2-(naphthalen-2-yl)-1-phenylpropyl acetate or a salt thereof. The 3-(methylamino)-2-(naphthalen-2-yl)-1-phenylpropyl acetate can comprise (2R, 3R)-3-(methylamino)-2-(naphthalen-2-yl)-1-phenylpropyl acetate or (2S, 3S)-3-(methylamino)-2-(naphthalen-2-yl)-1-phenylpropyl acetate. The 3-(methylamino)-2-(naphthalen-2-yl)-1-phenylpropyl acetate can comprise (2R, 3S)-3-(methylamino)-2-(naphthalen-2-yl)-1-phenylpropyl acetate or (2S, 3R)-3-(methylamino)-2-(naphthalen-2-yl)-1-phenylpropyl acetate. The 3-(methylamino)-2-(naphthalen-2-yl)-1-phenylpropyl acetate can comprise: (i) two compounds selected from the group consisting of (2R, 3R)-3-(methylamino)-2-(naphthalen-2-yl)-1-phenylpropyl acetate, (2S, 3S)-3-(methylamino)-2-(naphthalen-2-yl)-1-phenylpropyl acetate, (2R, 3S)-3-(methylamino)-2-(naphthalen-2-yl)-1-phenylpropyl acetate, and (2S, 3R)-3-(methylamino)-2-(naphthalen-2-yl)-1-phenylpropyl acetate; or (ii) three compounds selected from the group consisting of (2R, 3R)-3-(methylamino)-2-(naphthalen-2-yl)-1-phenylpropyl acetate, (2S, 3S)-3-(methylamino)-2-(naphthalen-2-yl)-1-phenylpropyl acetate, (2R, 3S)-3-(methylamino)-2-(naphthalen-2-yl)-1-phenylpropyl acetate, and (2S, 3R)-3-(methylamino)-2-(naphthalen-2-yl)-1-phenylpropyl acetate; or (iii) (2R, 3R)-3-(methylamino)-2-(naphthalen-2-yl)-1-phenylpropyl acetate, (2S, 3S)-3-(methylamino)-2-(naphthalen-2-yl)-1-phenylpropyl acetate, (2R, 3S)-3-(methylamino)-2-(naphthalen-2-yl)-1-phenylpropyl acetate, and (2S, 3R)-3-(methylamino)-2-(naphthalen-2-yl)-1-phenylpropyl acetate. The composition can comprise a pharmaceutically acceptable carrier.

In another aspect, this document features a composition comprising, or consisting essentially of, 3-methoxy-N-methyl-2-(naphthalen-2-yl)-3-phenylpropan-1-amine or a salt thereof. The 3-methoxy-N-methyl-2-(naphthalen-2-yl)-3-phenylpropan-1-amine can comprise (2R, 3R)-3-methoxy-N-methyl-2-(naphthalen-2-yl)-3-phenylpropan-1-amine or (2S, 3S)-3-methoxy-N-methyl-2-(naphthalen-2-yl)-3-phenylpropan-1-amine. The 3-methoxy-N-methyl-2-(naphthalen-2-yl)-3-phenylpropan-1-amine can comprise (2R, 3S)-3-methoxy-N-methyl-2-(naphthalen-2-yl)-3-phenylpropan-1-amine or (2S, 3R)-3-methoxy-N-methyl-2-(naphthalen-2-yl)-3-phenylpropan-1-amine. The 3-methoxy-N-methyl-2-(naphthalen-2-yl)-3-phenylpropan-1-amine can comprise: (i) two compounds selected from the group consisting of (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N-methyl-2-(naphthalen-2-yl)-3-phenylpropan-1-amine; or (ii) three compounds selected from the group consisting of (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N-methyl-2-(naphthalen-2-yl)-3-phenylpropan-1-amine; or (iii) (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N-methyl-2-(naphthalen-2-yl)-3-phenylpropan-1-amine. The composition can comprise a pharmaceutically acceptable carrier.

In another aspect, this document features a composition comprising, or consisting essentially of, 3-methoxy-N-methyl-2-(naphthalen-2-yl)-3-phenylpropan-1-amine or a salt thereof. The 3-methoxy-N-methyl-2-(naphthalen-2-yl)-3-phenylpropan-1-amine can comprise (2R, 3R)-3-methoxy-N-methyl-2-(naphthalen-2-yl)-3-phenylpropan-1-amine or (2S, 3S)-3-methoxy-N-methyl-2-(naphthalen-2-yl)-3-phenylpropan-1-amine. The 3-methoxy-N-methyl-2-(naphthalen-2-yl)-3-phenylpropan-1-amine can comprise (2R, 3S)-3-methoxy-N-methyl-2-(naphthalen-2-yl)-3-phenylpropan-1-amine or (2S, 3R)-3-methoxy-N-methyl-2-(naphthalen-2-yl)-3-phenylpropan-1-amine. The 3-methoxy-N-methyl-2-(naphthalen-2-yl)-3-phenylpropan-1-amine can comprise: (i) two compounds selected from the group consisting of (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N-methyl-2-(naphthalen-2-yl)-3-phenylpropan-1-amine; or (ii) three compounds selected from the group consisting of (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N- methyl-2-(naphthalen-2-yl)-3-phenylpropan-1-amine; or (iii) (2R, 3R)-3-methoxy-N-methyl-2-(naphthalen-2-yl)-3-phenylpropan-1-amine, (2S, 3S)-3-methoxy-N-methyl-2-(naphthalen-2-yl)-3-phenylpropan-1-amine, (2R, 3S)-3-methoxy-N-methyl-2-(naphthalen-2-yl)-3-phenylpropan-1-amine, and (2S, 3R)-3-methoxy-N-methyl-2-(naphthalen-2-yl)-3-phenylpropan-1-amine. The composition can comprise a pharmaceutically acceptable carrier.

In another aspect, this document features a composition comprising, or consisting essentially of, 1-methyl-5-(naphthalen-2-yl)-4-phenylhexahydropyrimidine or a salt thereof. The 1-methyl-5-(naphthalen-2-yl)-4-phenylhexahydropyrimidine can comprise (2R, 3R)-1-methyl-5-(naphthalen-2-yl)-4-phenylhexahydropyrimidine or (2S, 3S)-1-methyl-5-(naphthalen-2-yl)-4-phenylhexahydropyrimidine. The 1-methyl-5-(naphthalen-2-yl)-4-phenylhexahydropyrimidine can comprise (2R, 3S)-1-methyl-5-(naphthalen-2-yl)-4-phenylhexahydropyrimidine or (2S, 3R)-1-methyl-5-(naphthalen-2-yl)-4-phenylhexahydropyrimidine. The 1-methyl-5-(naphthalen-2-yl)-4-phenylhexahydropyrimidine can comprise: (i) two compounds selected from the group consisting of (2R, 3R)-1-methyl-5-(naphthalen-2-yl)-4-phenylhexahydropyrimidine, (2S, 3S)-1-methyl-5-(naphthalen-2-yl)-4-phenylhexahydropyrimidine, (2R, 3S)-1-methyl-5-(naphthalen-2-yl)-4-phenylhexahydropyrimidine, and (2S, 3R)-1-methyl-5-(naphthalen-2-yl)-4-phenylhexahydropyrimidine; or (ii) three compounds selected from the group consisting of (2R, 3R)-1-methyl-5-(naphthalen-2-yl)-4-phenylhexahydropyrimidine, (2S, 3S)-1-methyl-5-(naphthalen-2-yl)-4-phenylhexahydropyrimidine, (2R, 3S)-1-methyl-5-(naphthalen-2-yl)-4-phenylhexahydropyrimidine, and (2S, 3R)-1-methyl-5-(naphthalen-2-yl)-4-phenylhexahydropyrimidine; or (iii) (2R, 3R)-1-methyl-5-(naphthalen-2-yl)-4-phenylhexahydropyrimidine, (2S, 3S)-1-methyl-5-(naphthalen-2-yl)-4-phenylhexahydropyrimidine, (2R, 3S)-1-methyl-5-(naphthalen-2-yl)-4-phenylhexahydropyrimidine, and (2S, 3R)-1-methyl-5-(naphthalen-2-yl)-4-phenylhexahydropyrimidine. The composition can comprise a pharmaceutically acceptable carrier.

In another aspect, this document features a composition comprising, or consisting essentially of, N1,N1-dimethyl-2-(naphthalen-2-yl)-3-phenylpropane-1,3-diamine or a salt thereof. The N1,N1-dimethyl-2-(naphthalen-2-yl)-3-phenylpropane-1,3-diamine can comprise (2R, 3R)—N1,N1-dimethyl-2-(naphthalen-2-yl)-3-phenylpropane-1,3-diamine or (2S, 3S)—N1,N1-dimethyl-2-(naphthalen-2-yl)-3-phenylpropane-1,3-diamine. The N1,N1-dimethyl-2-(naphthalen-2-yl)-3-phenylpropane-1,3-diamine can comprise (2R, 3S)—N1,N1-dimethyl-2-(naphthalen-2-yl)-3-phenylpropane-1,3-diamine or (2S, 3R)—N1,N1-dimethyl-2-(naphthalen-2-yl)-3-phenylpropane-1,3-diamine. The N1,N1-dimethyl-2-(naphthalen-2-yl)-3-phenylpropane-1,3-diamine can comprise: (i) two compounds selected from the group consisting of (2R, 3R)—N1,N1-dimethyl-2-(naphthalen-2-yl)-3-phenylpropane-1,3-diamine, (2S, 3S)—N1,N1-dimethyl-2-(naphthalen-2-yl)-3-phenylpropane-1,3-diamine, (2R, 3S)—N1,N1-dimethyl-2-(naphthalen-2-yl)-3-phenylpropane-1,3-diamine, and (2S, 3R)—N1,N1-dimethyl-2-(naphthalen-2-yl)-3-phenylpropane-1,3-diamine; or (ii) three compounds selected from the group consisting of (2R, 3R)—N1,N1-dimethyl-2-(naphthalen-2-yl)-3-phenylpropane-1,3-diamine, (2S, 3S)—N1,N1-dimethyl-2-(naphthalen-2-yl)-3-phenylpropane-1,3-diamine, (2R, 3S)—N1,N1-dimethyl-2-(naphthalen-2-yl)-3-phenylpropane-1,3-diamine, and (2S, 3R)—N1,N1-dimethyl-2-(naphthalen-2-yl)-3-phenylpropane-1,3-diamine; or (iii) (2R, 3R)—N1,N1-dimethyl-2-(naphthalen-2-yl)-3-phenylpropane-1,3-diamine, (2S, 3S)—N1,N1-dimethyl-2-(naphthalen-2-yl)-3-phenylpropane-1,3-diamine, (2R, 3S)—N1,N1-dimethyl-2-(naphthalen-2-yl)-3-phenylpropane-1,3-diamine, and (2S, 3R)—N1,N1-dimethyl-2-(naphthalen-2-yl)-3-phenylpropane-1,3-diamine. The composition can comprise a pharmaceutically acceptable carrier.

In another aspect, this document features a composition comprising, or consisting essentially of, a dimer of 3-(methylamino)-2-(naphthalen-2-yl)-1-phenylpropan-1-ol or a salt thereof. The 3-(methylamino)-2-(naphthalen-2-yl)-1-phenylpropan-1-ol can comprise (2R, 3R)-3-(methylamino)-2-(naphthalen-2-yl)-1-phenylpropan-1-ol or (2S, 3S)-3-(methylamino)-2-(naphthalen-2-yl)-1-phenylpropan-1-ol. The 3-(methylamino)-2-(naphthalen-2-yl)-1-phenylpropan-1-ol can comprise (2R, 3S)-3-(methylamino)-2-(naphthalen-2-yl)-1-phenylpropan-1-ol or (2S, 3R)-3-(methylamino)-2-(naphthalen-2-yl)-1-phenylpropan-1-ol. The 3-(methylamino)-2-(naphthalen-2-yl)-1-phenylpropan-1-ol can comprise: (i) two compounds selected from the group consisting of (2R, 3R)-3-(methylamino)-2-(naphthalen-2-yl)-1-phenylpropan-1-ol, (2S, 3S)-3-(methylamino)-2-(naphthalen-2-yl)-1-phenylpropan-1-ol, (2R, 3S)-3-(methylamino)-2-(naphthalen-2-yl)-1-phenylpropan-1-ol, and (2S, 3R)-3-(methylamino)-2-(naphthalen-2-yl)-1-phenylpropan-1-ol; or (ii) three compounds selected from the group consisting of (2R, 3R)-3-(methylamino)-2-(naphthalen-2-yl)-1-phenylpropan-1-ol, (2S, 3S)-3-(methylamino)-2-(naphthalen-2-yl)-1-phenylpropan-1-ol, (2R, 3S)-3-(methylamino)-2-(naphthalen-2-yl)-1-phenylpropan-1-ol, and (2S, 3R)-3-(methylamino)-2-(naphthalen-2-yl)-1-phenylpropan-1-ol; or (iii) (2R, 3R)-3-(methylamino)-2-(naphthalen-2-yl)-1-phenylpropan-1-ol, (2S, 3S)-3-(methylamino)-2-(naphthalen-2-yl)-1-phenylpropan-1-ol, (2R, 3S)-3-(methylamino)-2-(naphthalen-2-yl)-1-phenylpropan-1-ol, and (2S, 3R)-3-(methylamino)-2-(naphthalen-2-yl)-1-phenylpropan-1-ol. The composition can comprise a pharmaceutically acceptable carrier.

In another aspect, this document features a method for inhibiting neurotransmitter reuptake in a mammal. The method comprises, or consists essentially of, administering a composition comprising a compound selected from the group consisting of 3-chloro-N-methyl-2-(naphthalen-2-yl)-3-phenylpropan-1-amine, 3-fluoro-N-methyl-2-(naphthalen-2-yl)-3-phenylpropan-1-amine, 3-azido-N-methyl-2-(naphthalen-2-yl)-3-phenylpropan-1-amine, N1-methyl-2-(naphthalen-2-yl)-3-phenylpropane-1,3-diamine, 3-(methylamino)-2-(naphthalen-2-yl)-1-phenylpropyl acetate, 3-methoxy-N-methyl-2-(naphthalen-2-yl)-3-phenylpropan-1-amine, 3-methoxy-N-methyl-2-(naphthalen-2-yl)-3-phenylpropan-1-amine, 1-methyl-5-(naphthalen-2-yl)-4-phenylhexahydropyrimidine, N1,N1-dimethyl-2-(naphthalen-2-yl)-3-phenylpropane-1,3-diamine, 3-(methylamino)-2-(naphthalen-2-yl)-1-phenylpropan-1-ol, a salt of any aforementioned compound, an enantiomer of any aforementioned compound or salt, and a combination of any aforementioned compound, salt, or enantiomer. The neurotransmitter reuptake can be norepinephrine or epinephrine reuptake. The neurotransmitter reuptake can be dopamine reuptake. The neurotransmitter reuptake can be serotonin reuptake. The mammal can be a human. The composition can have an CYP2D6 $IC_{50}$ value greater than 250 nM. The composition can have an CYP2D6 $IC_{50}$ value greater than 500 nM. The composition can have an CYP2D6 $IC_{50}$ value greater than 1000 nM.

In another aspect, this document features a composition comprising, or consisting essentially of, 3,3'-(butane-1,4-diylbis(oxy))bis(N-methyl-2-(naphthalen-2-yl)-3-phenylpropan-1-amine) or a salt thereof. The 3,3'-(butane-1,4-diylbis(oxy))bis(N-methyl-2-(naphthalen-2-yl)-3-phenylpropan-1-amine) can comprise (2S,2'S,3R,3'R)-3,3'-(butane-1,4-diylbis(oxy))bis(N-methyl-2-(naphthalen-2-yl)-3-phenylpropan-1-amine). The composition can comprise a pharmaceutically acceptable carrier.

In another aspect, this document features a composition comprising, or consisting essentially of, 3-methyl-5-(naphthalen-2-yl)-6-phenyl-1,3-oxazinane or a salt thereof. The 3-methyl-5-(naphthalen-2-yl)-6-phenyl-1,3-oxazinane can comprise (5R, 6R)-3-methyl-5-(naphthalen-2-yl)-6-phenyl-1,3-oxazinane or (5S, 6S)-3-methyl-5-(naphthalen-2-yl)-6-phenyl-1,3-oxazinane. The 3-methyl-5-(naphthalen-2-yl)-6-phenyl-1,3-oxazinane can comprise (5R, 6S)-3-methyl-5-(naphthalen-2-yl)-6-phenyl-1,3-oxazinane or (5S, 6R)-3-methyl-5-(naphthalen-2-yl)-6-phenyl-1,3-oxazinane. The 3-methyl-5-(naphthalen-2-yl)-6-phenyl-1,3-oxazinane can comprise: (i) two compounds selected from the group consisting of (5R, 6R)-3-methyl-5-(naphthalen-2-yl)-6-phenyl-1,3-oxazinane, (5S, 6S)-3-methyl-5-(naphthalen-2-yl)-6-phenyl-1,3-oxazinane, (5R, 6S)-3-methyl-5-(naphthalen-2-yl)-6-phenyl-1,3-oxazinane, and (5S, 6R)-3-methyl-5-(naphthalen-2-yl)-6-phenyl-1,3-oxazinane; or (ii) three compounds selected from the group consisting of (5R, 6R)-3-methyl-5-(naphthalen-2-yl)-6-phenyl-1,3-oxazinane, (5S, 6S)-3-methyl-5-(naphthalen-2-yl)-6-phenyl-1,3-oxazinane, (5R, 6S)-3-methyl-5-(naphthalen-2-yl)-6-phenyl-1,3-oxazinane, and (5S, 6R)-3-methyl-5-(naphthalen-2-yl)-6-phenyl-1,3-oxazinane; or (iii) (5R, 6R)-3-methyl-5-(naphthalen-2-yl)-6-phenyl-1,3-oxazinane, (5S, 6S)-3-methyl-5-(naphthalen-2-yl)-6-phenyl-1,3-oxazinane, (5R, 6S)-3-methyl-5-(naphthalen-2-yl)-6-phenyl-1,3-oxazinane, and (5S, 6R)-3-methyl-5-(naphthalen-2-yl)-6-phenyl-1,3-oxazinane. The composition can comprise a pharmaceutically acceptable carrier.

In another aspect, this document features a composition comprising, or consisting essentially of, 1,1-dimethyl-5-(naphthalen-2-yl)-4-phenylhexahydropyrimidin-1-ium chloride or a salt thereof. The 1,1-dimethyl-5-(naphthalen-2-yl)-4-phenylhexahydropyrimidin-1-ium chloride can comprise (4R, 5R)-1,1-dimethyl-5-(naphthalen-2-yl)-4-phenylhexahydropyrimidin-1-ium chloride or (4S, 5S)-1,1-dimethyl-5-(naphthalen-2-yl)-4-phenylhexahydropyrimidin-1-ium chloride. The 1,1-dimethyl-5-(naphthalen-2-yl)-4-phenylhexahydropyrimidin-1-ium chloride can comprise (4R, 5S)-1,1-dimethyl-5-(naphthalen-2-yl)-4-phenylhexahydropyrimidin-1-ium chloride or (4S, 5R)-1,1-dimethyl-5-(naphthalen-2-yl)-4-phenylhexahydropyrimidin-1-ium chloride. The 1,1-dimethyl-5-(naphthalen-2-yl)-4-phenylhexahydropyrimidin-1-ium chloride can comprise: (i) two compounds selected from the group consisting of (4R, 5R)-1,1-dimethyl-5-(naphthalen-2-yl)-4-phenylhexahydropyrimidin-1-ium chloride, (4S, 5S)-1,1-dimethyl-5-(naphthalen-2-yl)-4-phenylhexahydropyrimidin-1-ium chloride, (4R, 5S)-1,1-dimethyl-5-(naphthalen-2-yl)-4-phenylhexahydropyrimidin-1-ium chloride, and (4S, 5R)-1,1-dimethyl-5-(naphthalen-2-yl)-4-phenylhexahydropyrimidin-1-ium chloride; or (ii) three compounds selected from the group consisting of (4R, 5R)-1,1-dimethyl-5-(naphthalen-2-yl)-4-phenylhexahydropyrimidin-1-ium chloride, (4S, 5S)-1,1-dimethyl-5-(naphthalen-2-yl)-4-phenylhexahydropyrimidin-1-ium chloride, (4R, 5S)-1,1-dimethyl-5-(naphthalen-2-yl)-4-phenylhexahydropyrimidin-1-ium chloride, and (4S, 5R)-1,1-dimethyl-5-(naphthalen-2-yl)-4-phenylhexahydropyrimidin-1-ium chloride; or (iii) (4R, 5R)-1,1-dimethyl-5-(naphthalen-2-yl)-4-phenylhexahydropyrimidin-1-ium chloride, (4S, 5S)-1,1-dimethyl-5-(naphthalen-2-yl)-4-phenylhexahydropyrimidin-1-ium chloride, (4R, 5S)-1,1-dimethyl-5-(naphthalen-2-yl)-4-phenylhexahydropyrimidin-1-ium chloride, and (4S, 5R)-1,1-dimethyl-5-(naphthalen-2-yl)-4-phenylhexahydropyrimidin-1-ium chloride. The composition can comprise a pharmaceutically acceptable carrier.

In another aspect, this document features a composition comprising, or consisting essentially of, 3-methyl-5-(naphthalen-2-yl)-6-phenyl-1,3-oxazinane or a salt thereof. The 3-methyl-5-(naphthalen-2-yl)-6-phenyl-1,3-oxazinane can comprise (5R, 6R)-3-methyl-5-(naphthalen-2-yl)-6-phenyl-1,3-oxazinane or (5S, 6S)-3-methyl-5-(naphthalen-2-yl)-6-phenyl-1,3-oxazinane. The 3-methyl-5-(naphthalen-2-yl)-6-phenyl-1,3-oxazinane can comprise (5R, 6S)-3-methyl-5-(naphthalen-2-yl)-6-phenyl-1,3-oxazinane or (5S, 6R)-3-methyl-5-(naphthalen-2-yl)-6-phenyl-1,3-oxazinane.

The 3-methyl-5-(naphthalen-2-yl)-6-phenyl-1,3-oxazinane can comprise: (i) two compounds selected from the group consisting of (5R, 6R)-3-methyl-5-(naphthalen-2-yl)-6-phenyl-1,3-oxazinane, (5S, 6S)-3-methyl-5-(naphthalen-2-yl)-6-phenyl-1,3-oxazinane, (5R, 6S)-3-methyl-5-(naphthalen-2-yl)-6-phenyl-1,3-oxazinane, and (5S, 6R)-3-methyl-5-(naphthalen-2-yl)-6-phenyl-1,3-oxazinane; or (ii) three compounds selected from the group consisting of (5R, 6R)-3-methyl-5-(naphthalen-2-yl)-6-phenyl-1,3-oxazinane, (5S, 6S)-3-methyl-5-(naphthalen-2-yl)-6-phenyl-1,3-oxazinane, (5R, 6S)-3-methyl-5-(naphthalen-2-yl)-6-phenyl-1,3-oxazinane, and (5S, 6R)-3-methyl-5-(naphthalen-2-yl)-6-phenyl-1,3-oxazinane. The composition can comprise a pharmaceutically acceptable carrier.

In another aspect, this document features a composition comprising, or consisting essentially of, 5-(naphthalen-2-yl)-6-phenyl-1,3-oxazinane or a salt thereof. The 5-(naphthalen-2-yl)-6-phenyl-1,3-oxazinane can comprise (5R, 6R)-5-(naphthalen-2-yl)-6-phenyl-1,3-oxazinane or (5S, 6S)-5-(naphthalen-2-yl)-6-phenyl-1,3-oxazinane. The 5-(naphthalen-2-yl)-6-phenyl-1,3-oxazinane can comprise (5R, 6S)-5-(naphthalen-2-yl)-6-phenyl-1,3-oxazinane or (5S, 6R)-5-(naphthalen-2-yl)-6-phenyl-1,3-oxazinane. The 5-(naphthalen-2-yl)-6-phenyl-1,3-oxazinane can comprise: (i) two compounds selected from the group consisting of (5R, 6R)-5-(naphthalen-2-yl)-6-phenyl-1,3-oxazinane, (5S, 6S)-5-(naphthalen-2-yl)-6-phenyl-1,3-oxazinane, (5R, 6S)-5-(naphthalen-2-yl)-6-phenyl-1,3-oxazinane, and (5S, 6R)-5-(naphthalen-2-yl)-6-phenyl-1,3-oxazinane; or (ii) three compounds selected from the group consisting of (5R, 6R)-5-(naphthalen-2-yl)-6-phenyl-1,3-oxazinane, (5S, 6S)-5-(naphthalen-2-yl)-6-phenyl-1,3-oxazinane, (5R, 6S)-5-(naphthalen-2-yl)-6-phenyl-1,3-oxazinane, and (5S, 6R)-5-(naphthalen-2-yl)-6-phenyl-1,3-oxazinane; or (iii) (5R, 6R)-5-(naphthalen-2-yl)-6-phenyl-1,3-oxazinane, (5S, 6S)-5-(naphthalen-2-yl)-6-phenyl-1,3-oxazinane, (5R, 6S)-5-(naphthalen-2-yl)-6-phenyl-1,3-oxazinane, and (5S, 6R)-5-(naphthalen-2-yl)-6-phenyl-1,3-oxazinane. The composition can comprise a pharmaceutically acceptable carrier.

In another aspect, this document features a composition comprising, or consisting essentially of, 3-chloro-N-methyl-2-(naphthalen-2-yl)-3-phenylpropan-1-amine or a salt thereof. The 3-chloro-N-methyl-2-(naphthalen-2-yl)-3-phenylpropan-1-amine can comprise (2R, 3R)-3-chloro-N-methyl-2-(naphthalen-2-yl)-3-phenylpropan-1-amine or (2S, 3S)-3-chloro-N-methyl-2-(naphthalen-2-yl)-3-phenylpropan-1-amine. The 3-chloro-N-methyl-2-(naphthalen-2-yl)-3-phenylpropan-1-amine can comprise (2R, 3S)-3-chloro-N-methyl-2-(naphthalen-2-yl)-3-phenylpropan-1-amine or (2S, 3R)-3-chloro-N-methyl-2-(naphthalen-2-yl)-3-phenylpropan-1-amine. The 3-chloro-N-methyl-2-(naphthalen-2-yl)-3-phenylpropan-1-amine can comprise: (i) two compounds selected from the group consisting of (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, and (2S, 3R)-3-chloro-N-methyl-2-(naphthalen-2-yl)-3-phenylpropan-1-amine; or (ii) three compounds selected from the group consisting of (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine; or (iii) (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine. The composition can comprise a pharmaceutically acceptable carrier.

In another aspect, this document features a method for treating pain, depression, major depressive disorder, or anxiety. The method comprises, or consists essentially of, administering, to a mammal, (a) one or more of the compounds of Table 1 or a salt thereof, (b) one or more stereoisomers of a compound of Table 1 or a salt thereof, or (c) a mixture of stereoisomers of a compound of Table 1 or salts thereof.

In another aspect, this document features a composition comprising, or consisting essentially of, a pharmaceutically acceptable carrier and (2R,3R)-3-(methylamino)-2-(naphthalen-2-yl)-1-phenylpropyl acetate or a pharmaceutically acceptable salt of the (2R,3R)-3-(methylamino)-2-(naphthalen-2-yl)-1-phenylpropyl acetate. The (2R,3R)-3-(methylamino)-2-(naphthalen-2-yl)-1-phenylpropyl acetate or pharmaceutically acceptable salt can be enantiomerically pure. The composition can lack (2S,3S)-3-(methylamino)-2-(naphthalen-2-yl)-1-phenylpropyl acetate or a salt thereof. The composition can lack (2R,3S)-3-(methylamino)-2-(naphthalen-2-yl)-1-phenylpropyl acetate or a salt thereof. The composition can lack (2S,3R)-3-(methylamino)-2-(naphthalen-2-yl)-1-phenylpropyl acetate or a salt thereof. The composition can lack (2S,3S)-3-(methylamino)-2-(naphthalen-2-yl)-1-phenylpropyl acetate, (2R,3S)-3-(methylamino)-2-(naphthalen-2-yl)-1-phenylpropyl acetate, (2S, 3R)-3-(methylamino)-2-(naphthalen-2-yl)-1-phenylpropyl acetate, and salts thereof. The composition can comprise the (2R,3R)-3-(methylamino)-2-(naphthalen-2-yl)-1-phenylpropyl acetate. The composition can comprise the pharmaceutically acceptable salt.

In another aspect, this document features a compound selected from the group consisting of (2R,3R)-3-(methylamino)-2-(naphthalen-2-yl)-1-phenylpropyl acetate and a pharmaceutically acceptable salt thereof.

In another aspect, this document features the compound (2R,3R)-3-(methylamino)-2-(naphthalen-2-yl)-1-phenylpropyl hydrochloride.

In another aspect, this document features a composition comprising, or consisting essentially of, a pharmaceutically acceptable carrier and (2S,3S)-3-(methylamino)-2-(naphthalen-2-yl)-1-phenylpropyl acetate or a pharmaceutically acceptable salt of the (2S,3S)-3-(methylamino)-2-(naphthalen-2-yl)-1-phenylpropyl acetate. The (2S,3S)-3-(methylamino)-2-(naphthalen-2-yl)-1-phenylpropyl acetate or pharmaceutically acceptable salt can be enantiomerically pure. The composition can lack (2R,3R)-3-(methylamino)-2-(naphthalen-2-yl)-1-phenylpropyl acetate or a salt thereof. The composition can lack (2R,3S)-3-(methylamino)-2-(naphthalen-2-yl)-1-phenylpropyl acetate or a salt thereof. The composition can lack (2S,3R)-3-(methylamino)-2-(naphthalen-2-yl)-1-phenylpropyl acetate or a salt thereof. The composition can lack (2R,3R)-3-(methylamino)-2-(naphthalen-2-yl)-1-phenylpropyl acetate, (2R,3S)-3-(methylamino)-2-(naphthalen-2-yl)-1-phenylpropyl acetate, (2S, 3R)-3-(methylamino)-2-(naphthalen-2-yl)-1-phenylpropyl acetate, and salts thereof. The composition can comprise the (2S,3S)-3-(methylamino)-2-(naphthalen-2-yl)-1-phenylpropyl acetate. The composition can comprise the pharmaceutically acceptable salt.

In another aspect, this document features a compound selected from the group consisting of (2S,3S)-3-(methylamino)-2-(naphthalen-2-yl)-1-phenylpropyl acetate and a pharmaceutically acceptable salt thereof.

In another aspect, this document features the compound (2S,3S)-3-(methylamino)-2-(naphthalen-2-yl)-1-phenylpropyl hydrochloride.

In another aspect, this document features a composition comprising, or consisting essentially of, a pharmaceutically acceptable carrier and (2S,3R)-3-(methylamino)-2-(naphthalen-2-yl)-1-phenylpropyl acetate or a pharmaceutically acceptable salt of the (2S,3R)-3-(methylamino)-2-(naphthalen-2-yl)-1-phenylpropyl acetate. The (2S,3R)-3-(methylamino)-2-(naphthalen-2-yl)-1-phenylpropyl acetate or pharmaceutically acceptable salt can be enantiomerically pure. The composition can lack (2R,3R)-3-(methylamino)-2-(naphthalen-2-yl)-1-phenylpropyl acetate or a salt thereof. The composition can lack (2S,3S)-3-(methylamino)-2-(naphthalen-2-yl)-1-phenylpropyl acetate or a salt thereof. The composition can lack (2R,3S)-3-(methylamino)-2-(naphthalen-2-yl)-1-phenylpropyl acetate or a salt thereof. The composition can lack (2R,3R)-3-(methylamino)-2-(naphthalen-2-yl)-1-phenylpropyl acetate, (2S,3S)-3-(methylamino)-2-(naphthalen-2-yl)-1-phenylpropyl acetate, (2R,3S)-3-(methylamino)-2-(naphthalen-2-yl)-1-phenylpropyl acetate, and salts thereof. The composition can comprise the (2S,3R)-3-(methylamino)-2-(naphthalen-2-yl)-1-phenylpropyl acetate. The composition can comprise the pharmaceutically acceptable salt.

In another aspect, this document features a compound selected from the group consisting of (2S,3R)-3-(methylamino)-2-(naphthalen-2-yl)-1-phenylpropyl acetate and a pharmaceutically acceptable salt thereof.

In another aspect, this document features the compound (2S,3R)-3-(methylamino)-2-(naphthalen-2-yl)-1-phenylpropyl hydrochloride.

In another aspect, this document features a composition comprising, or consisting essentially of, a pharmaceutically acceptable carrier and enantiomerically pure (2R,3S)-3-(methylamino)-2-(naphthalen-2-yl)-1-phenylpropyl acetate or a pharmaceutically acceptable salt of the enantiomerically pure (2R,3S)-3-(methylamino)-2-(naphthalen-2-yl)-1-phenylpropyl acetate.

The (2R,3S)-3-(methylamino)-2-(naphthalen-2-yl)-1-phenylpropyl acetate or pharmaceutically acceptable salt can be enantiomerically pure. The composition can lack (2R,3R)-3-(methylamino)-2-(naphthalen-2-yl)-1-phenylpropyl acetate or a salt thereof. The composition can lack (2S,3S)-3-(methylamino)-2-(naphthalen-2-yl)-1-phenylpropyl acetate or a salt thereof. The composition can lack (2S,3R)-3-(methylamino)-2-(naphthalen-2-yl)-1-phenylpropyl acetate or a salt thereof. The composition can lack (2R,3R)-3-(methylamino)-2-(naphthalen-2-yl)-1-phenylpropyl acetate, (2S,3S)-3-(methylamino)-2-(naphthalen-2-yl)-1- phenylpropyl acetate, (2S,3R)-3-(methylamino)-2-(naphthalen-2-yl)-1-phenylpropyl acetate, and salts thereof. The composition can comprise the (2R,3S)-3-(methylamino)-2-(naphthalen-2-yl)-1-phenylpropyl acetate. The composition can comprise the pharmaceutically acceptable salt.

In another aspect, this document features a compound selected from the group consisting of (2R,3S)-3-(methylamino)-2-(naphthalen-2-yl)-1-phenylpropyl acetate and a pharmaceutically acceptable salt thereof.

In another aspect, this document features the compound (2R,3S)-3-(methylamino)-2-(naphthalen-2-yl)-1-phenylpropyl hydrochloride.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 5:
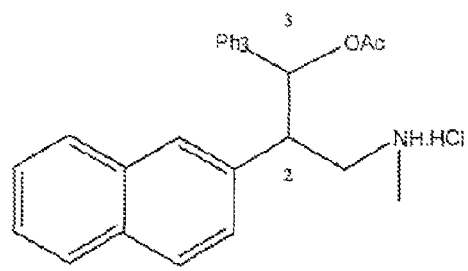
FIG. 5 is a diagram of 3-(methylamino)-2-(naphthalen-2-yl)-1-phenylpropyl acetate and its four stereoisomers.
Figure 5:
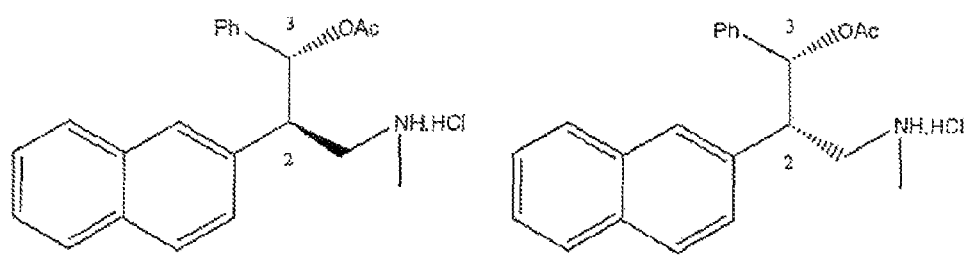
Figure 5:
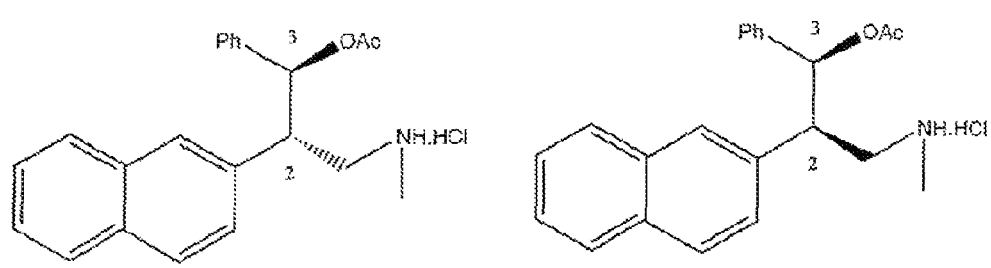
Figure 6:
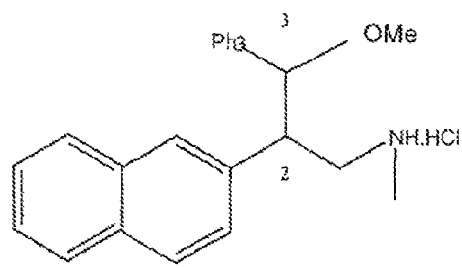
FIG. 6 is a diagram of 3-methoxy-N-methyl-2-(naphthalen-2-yl)-3-phenylpropan-1-amine and its four stereoisomers.
Figure 6:
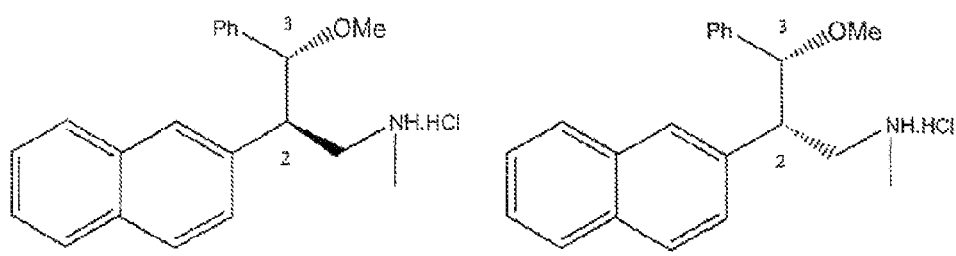
Figure 6:
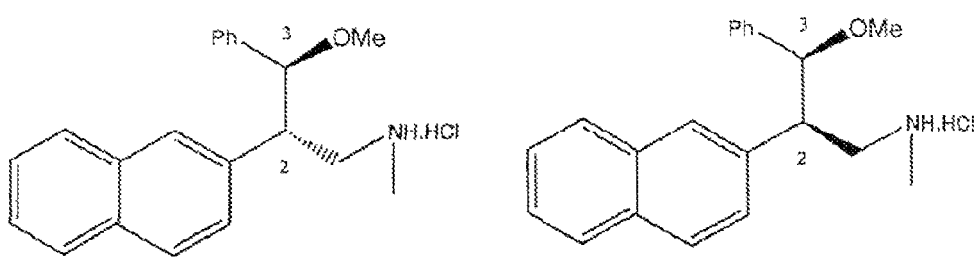
Figure 7:
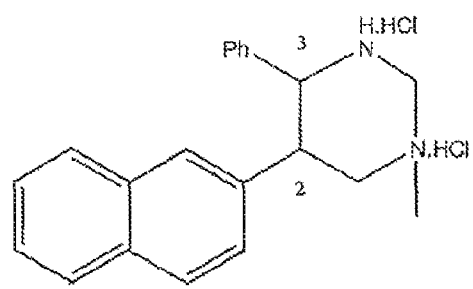
FIG. 7 is a diagram of 1-methyl-5-(naphthalen-2-yl)-4-phenylhexahydropyrimidine and its four stereoisomers.
Figure 7:
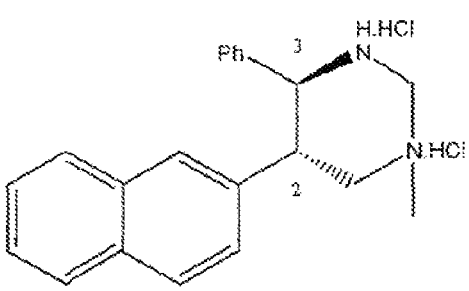
Figure 7:
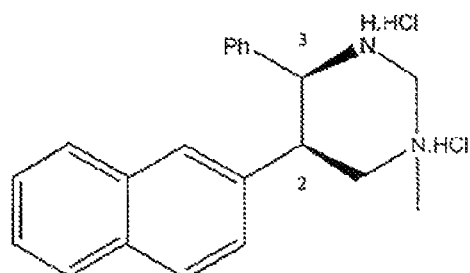
Figure 7:
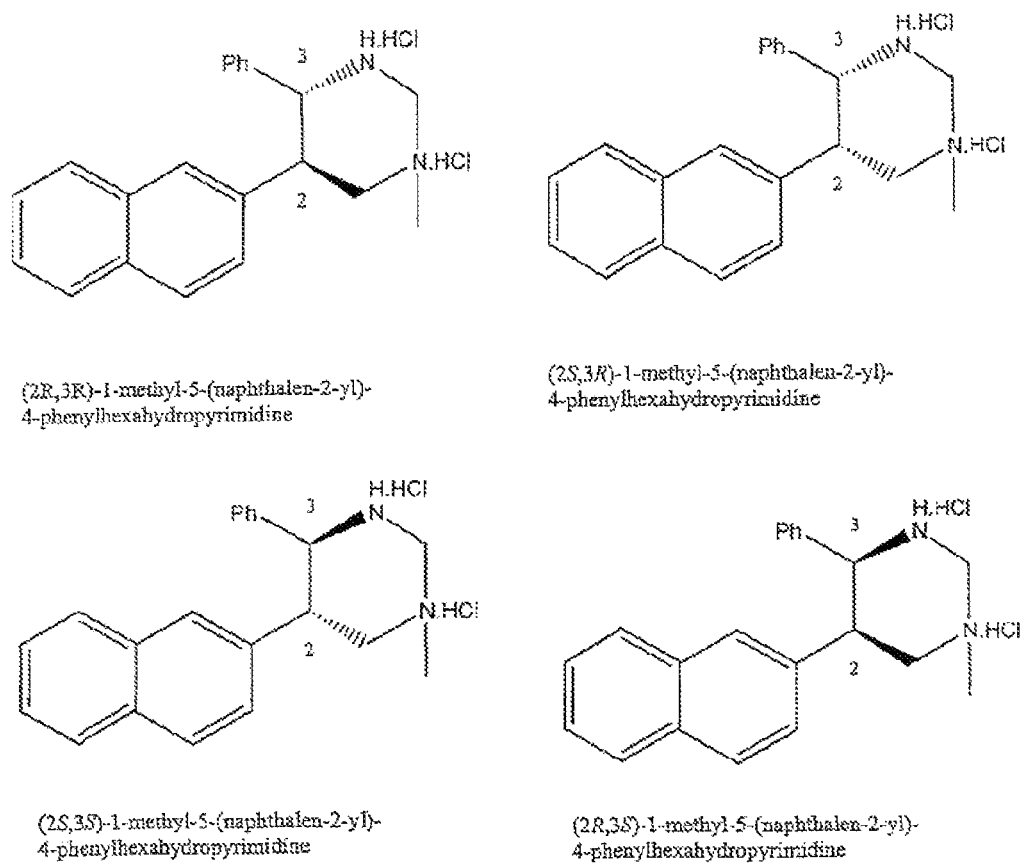
Figure 8:
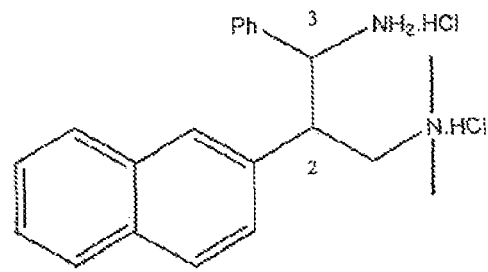
FIG. 8 is a diagram of N1,N1-dimethyl-2-(naphthalen-2-yl)-3-phenylpropane-1,3-diamine and its four stereoisomers.
Figure 8:
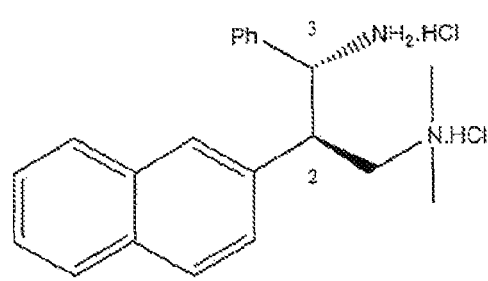
Figure 8:
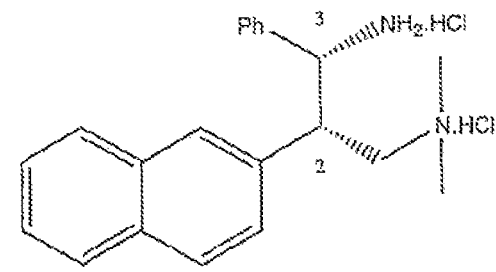
Figure 8:
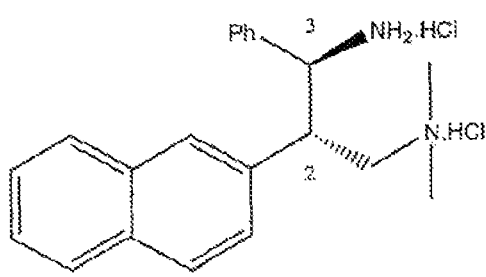
Figure 8:
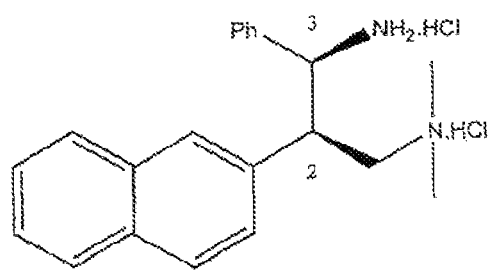
Figure 9:
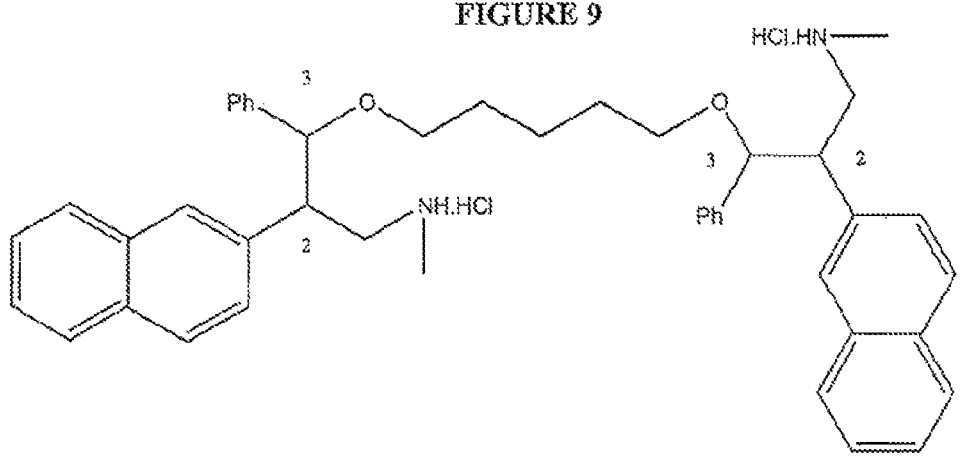
FIG. 9 is a diagram of a dimer of 3-(methylamino)-2-(naphthalen-2-yl)-1-phenylpropan-1-ol and its four stereoisomers.
Figure 9:
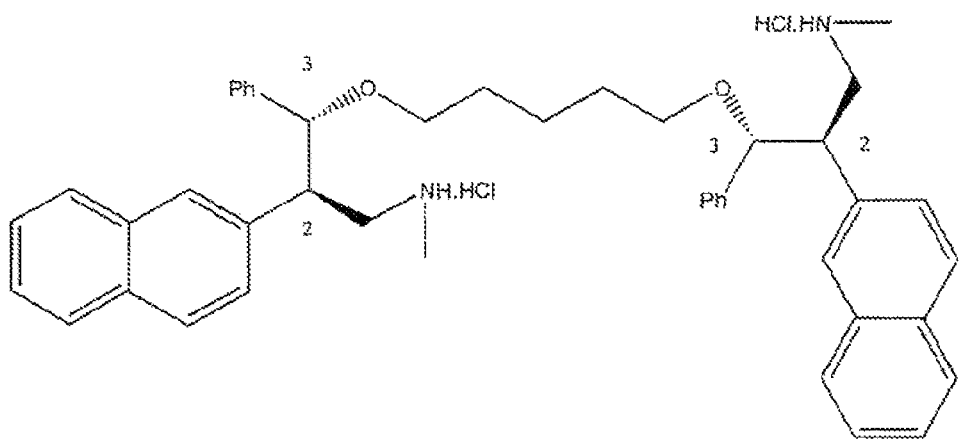
Figure 9:
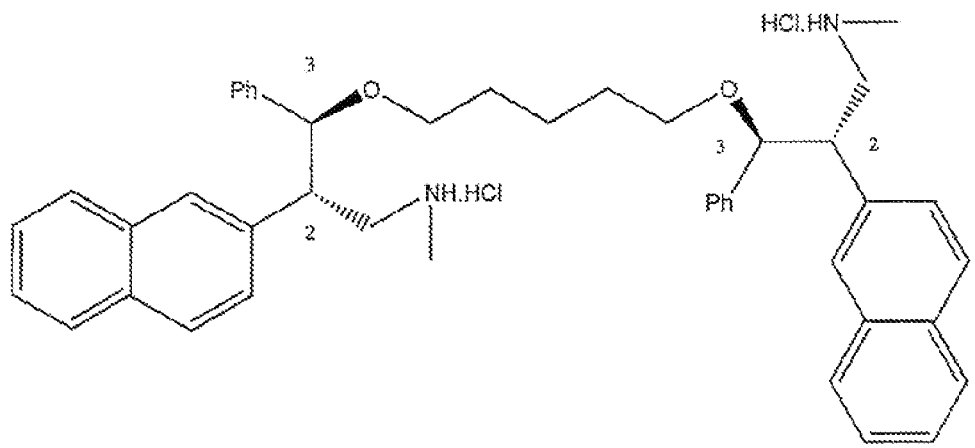
Figure 9:
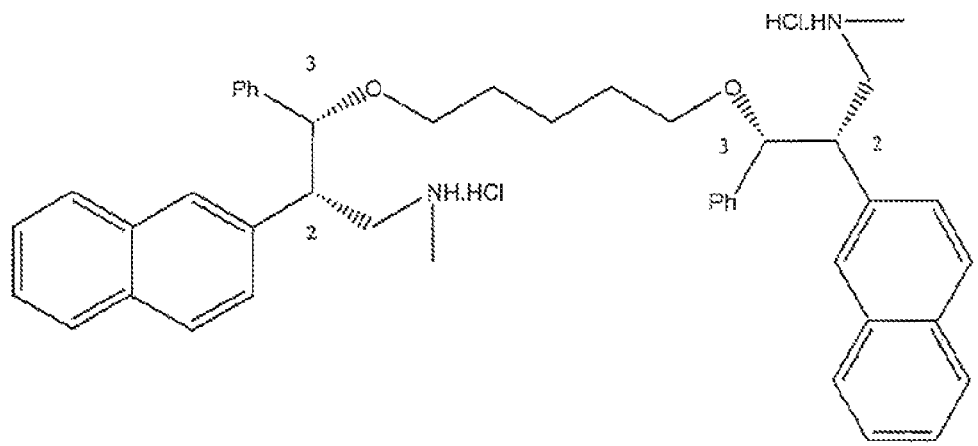
Figure 9:
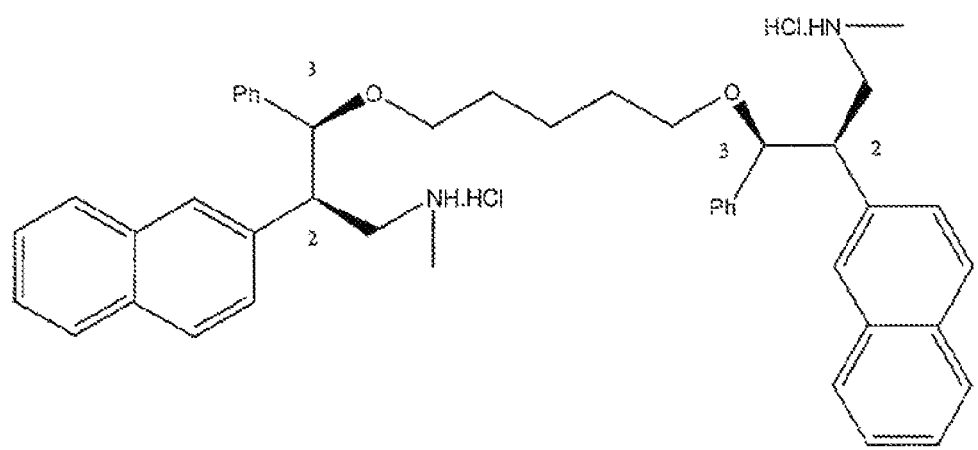
Figure 13:
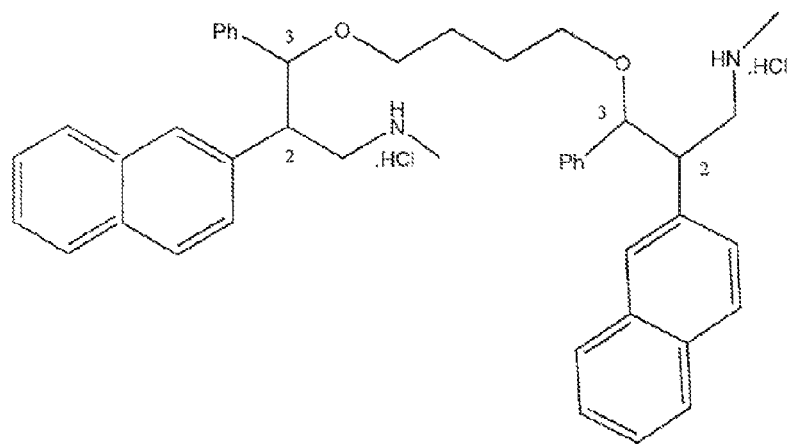
FIG. 13 is a diagram of 3,3'-(butane-1,4-diylbis(oxy))bis(N-methyl-2-(naphthalen-2-yl)-3-phenylpropan-1-amine) and its four stereoisomers.
Figure 13:
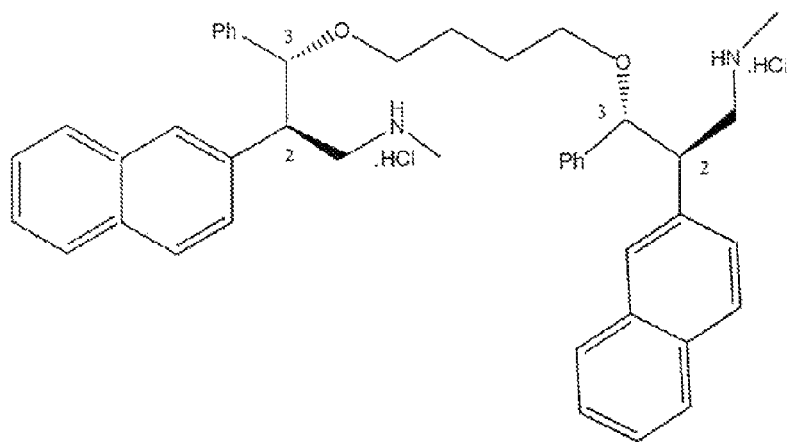
Figure 13:
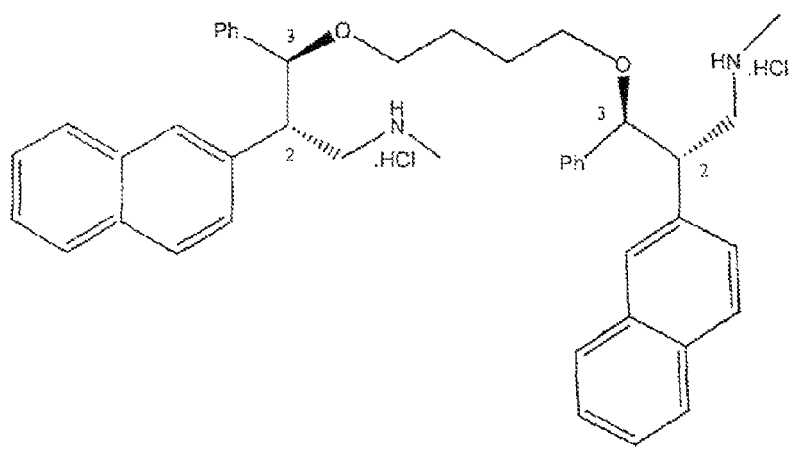
Figure 13:
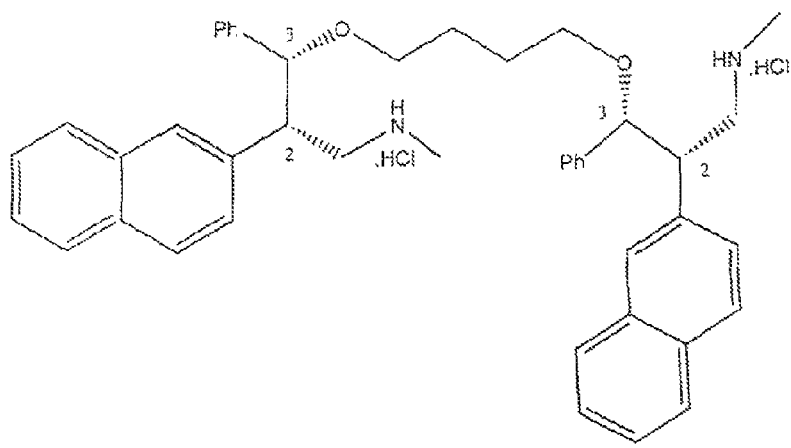
Figure 13:
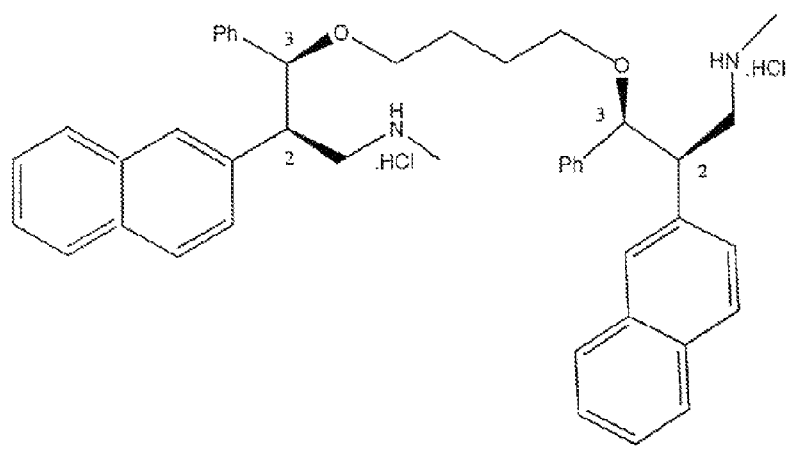
Figure 14:
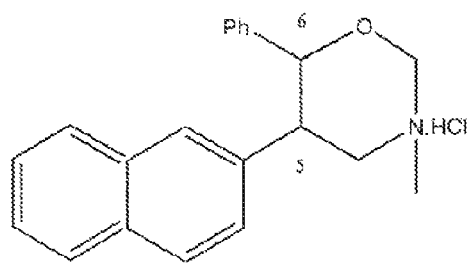
FIG. 14 is a diagram of 3-methyl-5-(naphthalen-2-yl)-6-phenyl-1,3-oxazinane and its four stereoisomers.
Figure 14:
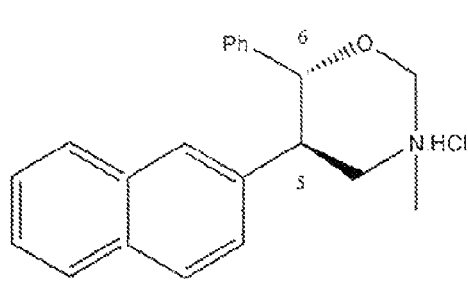
Figure 14:
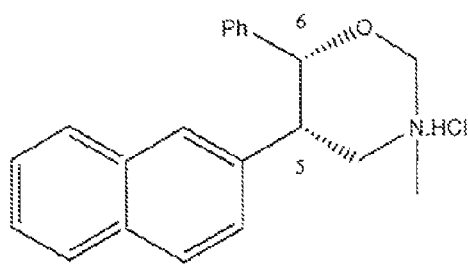
Figure 14:
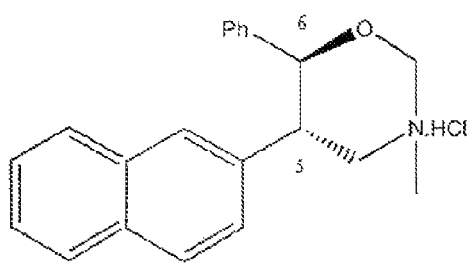
Figure 14:
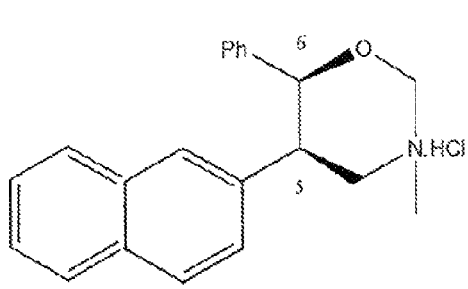
Figure 15:
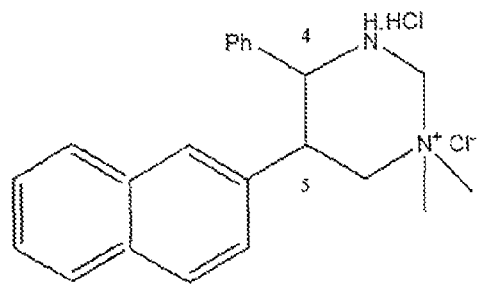
FIG. 15 is a diagram of 1,1-dimethyl-5-(naphthalen-2-yl)-4-phenylhexahydropyrimidin-1-ium chloride and its four stereoisomers.
Figure 15:
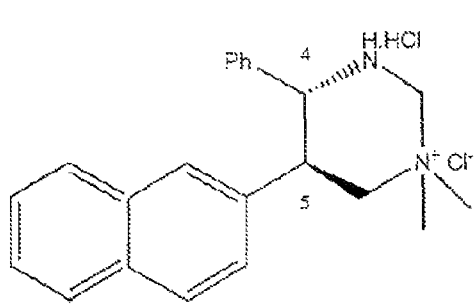
Figure 15:
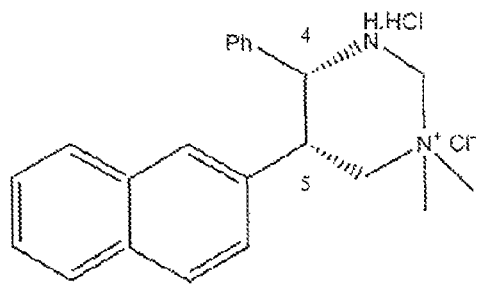
Figure 15:
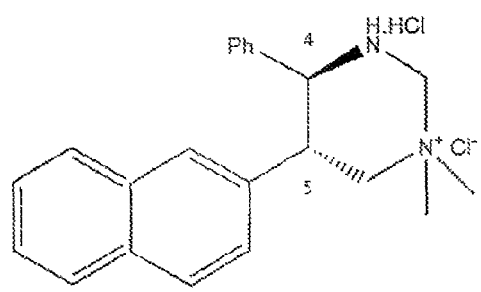
Figure 15:
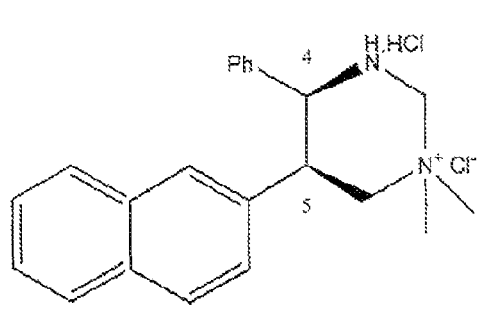
Figure 16:
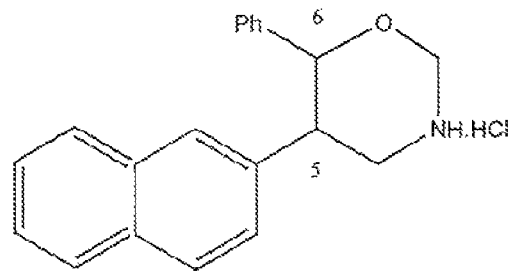
FIG. 16 is a diagram of 5-(naphthalen-2-yl)-6-phenyl-1,3-oxazinane and its four stereoisomers.
Figure 16:
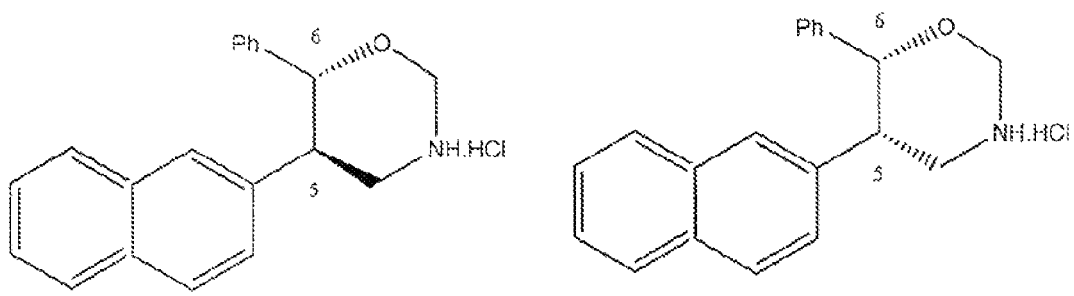
Figure 16:
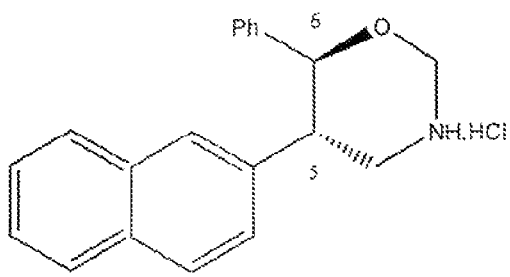

This document relates to compounds as well as methods and materials involved in modulating neurotransmitter reuptake. For example, this document provides compounds (e.g., amine compounds), methods for synthesizing compounds, and methods for inhibiting neurotransmitter reuptake. Examples of compounds provided herein include, without limitation, 3-chloro-N-methyl-2-(naphthalen-2-yl)-3-phenylpropan-1-amine (FIG. 1), 3-fluoro-N-methyl-2-(naphthalen-2-yl)-3-phenylpropan-1-amine (FIG. 2), 3-azido-N-methyl-2-(naphthalen-2-yl)-3-phenylpropan-1-amine (FIG. 3), N1-methyl-2-(naphthalen-2-yl)-3-phenylpropane-1,3-diamine (FIG. 4), 3-(methylamino)-2-(naphthalen-2-yl)-1-phenylpropyl acetate (FIG. 5), 3-methoxy-N-methyl-2-(naphthalen-2-yl)-3-phenylpropan-1-amine (FIG. 6), 1-methyl-5-(naphthalen-2-yl)-4-phenylhexahydropyrimidine (FIG. 7), N1,N1-dimethyl-2-(naphthalen-2-yl)-3-phenylpropane-1,3-diamine (FIG. 8), a dimer of 3-(methylamino)-2-(naphthalen-2-yl)-1-phenylpropan-1-ol (FIG. 9), 3,3'-(butane-1,4-diylbis(oxy))bis(N-methyl-2-(naphthalen-2-yl)-3-phenylpropan-1-amine) (FIG. 13), 3-methyl-5-(naphthalen-2-yl)-6-phenyl-1,3-oxazinane (FIG. 14), 1,1-dimethyl-5-(naphthalen-2-yl)-4-phenylhexahydropyrimidin-1-ium chloride (FIGS. 15), and 5-(naphthalen-2-yl)-6-phenyl-1,3-oxazinane (FIG. 16).

It is understood that a particular compound can include any one of that compound's stereoisomers as well as any combination thereof. For example, an 3-chloro-N-methyl-2-(naphthalen-2-yl)-3-phenylpropan-1-amine compound can be (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, or (2S, 3R)-3-chloro-N-methyl-2-(naphthalen-2-yl)-3-phenylpropan-1-amine, or any combination of (2R, 3R)-3-chloro-N-methyl-2-(naphthalen-2-yl)-3-phenylpropan-1-amine, (2S, 3S)-3-chloro-N-methyl-2-(naphthalen-2-yl)-3-phenylpropan-1-amine, (2R, 3S)-3-chloro-N-methyl-2-(naphthalen-2-yl)-3-phenylpropan-1-amine, and (2S, 3R)-3-chloro-N-methyl-2-(naphthalen-2-yl)-3-phenylpropan-1-amine. Examples of particular stereoisomers are provided in FIGS. 1-9 and 13-16. For example, a compound provided herein can be a (2R,3R)-3-(methylamino)-2-(naphthalen-2-yl)-1-phenylpropyl acetate compound, a (2S,3S)-3-(methylamino)-2-(naphthalen-2-yl)-1-phenylpropyl acetate compound, a (2S,3R)-3-(methylamino)-2-(naphthalen-2-yl)-1-phenylpropyl acetate compound, a (2R,3S)-3-(methylamino)-2-(naphthalen-2-yl)-1-phenylpropyl acetate compound, or any combination thereof. In some cases, a composition can be designed to contain any of the sterioisomers provided herein in an enantiomerically pure manner. For example, composition can be designed to include a (2R,3R)-3-(methylamino)-2-(naphthalen-2-yl)-1-phenylpropyl acetate compound without containing any detectable amounts of a (2S,3S)-3-(methylamino)-2-(naphthalen-2-yl)-1-phenylpropyl acetate compound, a (2S, 3R)-3-(methylamino)-2-(naphthalen-2-yl)-1-phenylpropyl acetate compound, or a (2R,3S)-3-(methylamino)-2-(naphthalen-2-yl)-1-phenylpropyl acetate compound.

This document also provides methods of synthesizing compounds such as amine compounds. For example, the compounds provided herein can be synthesized by a variety of organic chemistry techniques including, without limitation, addition of α-cyanomethylaryl anions to aryl or alkyl aldehydes to give predominantly anti-oriented β-hydroxynitriles, reduction of the resulting nitrile to a primary amine by lithium aluminum hydride or borane, conversion of the primary amine to a mono- or di-methylamine through an appropriate carbamate with reducing agents, such as lithium aluminum hydride or borane, and finally resolving the racemic amines by chiral acid-mediated optical resolution. Other methods of synthesis that can be used include inversion of stereochemistry of a hydroxyl group at the C-3 by variations of Mitsunobu reactions resulting in benzoates, azides, and amines, diethylaminosulfur trifluoride (DAST)-mediated fluorination of a hydroxyl group at C-3, and cyclization of the 1,3-amino alcohols and diamines to 6-membered cyclic hemiaminals and diaminals, respectively. Other compounds with cis-stereochemistry can be isolated either as minor products from aldol-type reactions, or through Mitsunobu reactions of their major anti counterparts containing a hydroxyl group at C-3.

A 3-fluoro-substituted compound provided herein can be synthesized by reaction of an alcohol with DAST. For example, a carbanion derived from 2-naphthylmethyl cyanide by reaction with lithium diisopropylamide can be treated with benzaldehyde to give predominantly a β-hydroxynitrile with anti stereochemistry that can be treated with DAST to produce 3-fluoro-N-methyl-2-(naphthalen-2-yl)-3-phenylpropan-1-amine.

Any compound provided herein can be a mixture of stereoisomers or can be resolved to form a racemic syn-diastereomer composition, or a racemic anti-diastereomer composition, or these racemates can be optically resolved to furnish pure enantiomers. For example, a compound can be resolved to a pure enantiomer by classical resolution using enantiomerically pure acids including, without limitation, (+)- and (−)-tartaric acid, (+)- and (−)-ditoluyl-tartaric acid, (+)- and (−)-camphorsulfonic acid, or any other optically pure acid.

Figure 3:
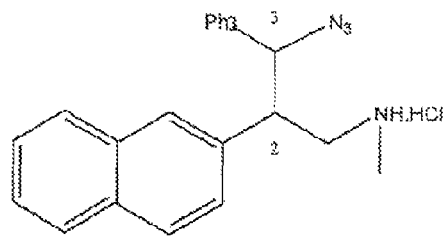
FIG. 3 is a diagram of 3-azido-N-methyl-2-(naphthalen-2-yl)-3-phenylpropan-1-amine and its four stereoisomers.
Figure 3:
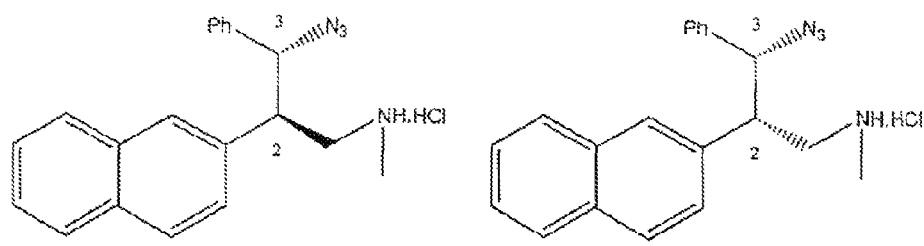
Figure 3:
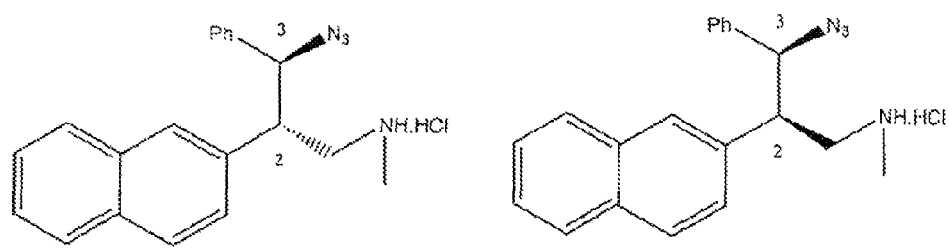

Any appropriate method can be used to isolate diastereomers and enantiomers such as those described elsewhere (Eliel et al., In: Stereochemistry of Organic Compounds; John Wiley & Sons: New York, 1994). For example, a racemic anti-diastereomer of 3-azido-N-methyl-2-(naphthalen-2-yl)-3-phenylpropan-1-amine (50:50 2R,3R and 2S,3S; FIG. 3) can be isolated by: chromatography of the crude product mixture, or the mother liquor of the crystallization used to isolate 3-hydroxy-2-(naphthalen-2-yl)-3-phenylpropanenitrile with anti stereochemistry. Reduction of this racemic compound can yield the racemic anti-diastereomer of 3-hydroxy-2-(naphthalen-2-yl)-3-phenylpropan-1-amine (FIG. 3), which can be N-methylated via a carbamate to give the racemic anti-diastereomer of 3-hydroxy-N-methyl-2-(naphthalen-2-yl)-3-phenylpropan-1-amine. After conversion to a butoxycarbonyl (N-Boc) carbamate of the secondary amine followed by a standard Mitsunobu inversion of the 3-hydroxyl function with an azide, hydrolysis of the N-Boc can be performed to furnish racemic anti-3-azido-N-methyl-2-(naphthalen-2-yl)-3-phenylpropan-1-amine.

The racemic anti-diastereomeric mixture (50:50 of the 2S, 3S and 2R, 3R enantiomers) of any of the derivatives provided herein can be resolved into the pure enantiomers by classical optical resolution methods. For example, racemic 3-hydroxy-N-methyl-2-(naphthalen-2-yl)-3-phenylpropan-1-amine can be treated with several different enantiomerically pure acids. The resulting ammonium carboxylate salts can be selectively recrystallized because of their possible differential solubility. After obtaining a diastereomerically pure salt, the chiral acid can be removed, and the resulting enantiomerically pure free amine can be converted to a hydrochloride salt.

Any compound or enantiomer thereof provided herein can be chemically converted from its free base form to a pharmaceutically acceptable salt by reacting the free base with an equivalent amount of any acid that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. Any compound or pharmaceutically acceptable salt thereof provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants, chelating agents, inert gases, and the like can also be present. It will be appreciated that any compound provided herein that is to be administered to a mammal can contain zero, one, or more than one commonly known pharmaceutically acceptable carriers.

This document provides methods for using the compounds provided herein to inhibit neurotransmitter reuptake in a mammal. The term "inhibit" as used herein with respect to neurotransmitter reuptake refers to any reduction in neurotransmitter reuptake. For example, a reduction in neurotransmitter reuptake greater than zero percent (e.g., greater than 0.1, 0.5, 1, 2, 5, 10, 25, 50, 75, or 99 percent) is considered an inhibition of neurotransmitter reuptake. In some embodiments, a compound provided herein can inhibit neurotransmitter reuptake such that the reduction in neurotransmitter reuptake is greater than zero percent (e.g., greater than 0.1, 0.5, 1, 2, 5, 10, 25, 50, 65, 75, 85, 95, or 99 percent) as compared to untreated controls (e.g., untreated mammals or cells). Any appropriate method can be used to assess whether or not neurotransmitter reuptake has been inhibited in a mammal. Such methods can be qualitative or quantitative. An example of a qualitative method includes assessing whether or not a mammal with depression experiences loss of pleasure in daily activities, significant weight loss or gain, changes in mobility (e.g., lethargy, nervousness), feelings of worthlessness, diminished ability to concentrate, or suicidal thoughts to a lesser extent following treatment with a compound provided herein than the extent experienced before treatment. In some cases, such methods can be quantitative. For example, the concentration of serotonin in a platelet sample from a mammal after treatment with a compound provided herein can be measured and compared to the concentration of serotonin in a platelet sample from the same mammal before treatment with that compound. If the concentration of serotonin after treatment is reduced compared to the concentration of serotonin before treatment, then that compound inhibited neurotransmitter reuptake in that mammal.

To inhibit neurotransmitter reuptake, an effective amount of any compound provided herein can be administered to a mammal. The term "effective" as used herein refers to any amount that induces a desired level of neurotransmitter reuptake inhibition while not inducing significant toxicity in the mammal. Such an amount can be determined using the methods and materials provided herein. An effective amount of a compound or formulation containing a compound can be any amount that reduces, prevents, or eliminates an anxiety or depressive disorder upon administration to a mammal without producing significant toxicity to that mammal. Some compounds may have a relatively broad concentration range that is effective while others may have a relatively narrow effective concentration range. In addition, the effective amount can vary depending upon the specific mammal or the specific anxiety or depressive disorder to be treated because certain mammals and anxiety or depressive disorders can be more or less responsive to a particular compound. Such effective amounts can be determined for individual compounds using commonly available or easily ascertainable information involving equilibrium dissociation constants, mammal toxicity concentrations, and bioavailability. For example, non-toxic compounds typically can be directly or indirectly administered to a mammal in any amount that reduces, prevents, or eliminates an anxiety or depressive disorder in that mammal. Using the information provided herein, such effective amounts can also be determined by routine experimentation in vitro or in vivo. For example, a patient having an anxiety or depressive disorder can receive direct administration of a compound provided herein in an amount to achieve a blood level close to the equilibrium dissociation constant (i.e., $K_d$) calculated from in vitro analysis sufficient to inhibit the uptake of a particular neurotransmitter. If the patient fails to respond, then the amount can be increased by, for example, two fold. After receiving this higher concentration, the patient can be monitored for both responsiveness to the treatment and toxicity symptoms, as well as blood levels of the drug, and adjustments made accordingly.

To help determine effective amounts of different compounds, it can be useful to refer to an effective amount equivalent based on the effective amount of a common drug used to treat anxiety or depressive disorders. For example, the direct administration of 0.30 mg/kg Prozac® (fluoxetine) daily for three weeks to a mammal can be an effective amount for treating anxiety or depressive disorders. The effects produced by this effective amount can be used as a reference point to compare the effects observed for other compounds used at varying concentrations. Once an equivalent effect is observed, then the specific effective amount for that particular compound can be determined. In this case, that particular amount would be termed a Prozac® effective amount equivalent.

The ability of a compound to inhibit neurotransmitter reuptake also can be assessed in vitro. For example, the level of serotonin reuptake can be determined by measuring the amount of radiolabeled serotonin taken up by synaptosomes ("pinched-off" nerve endings) purified from a tissue source abundant in serotonin transporters (e.g., rat brain cortical tissue). Rat brain cortical tissue can be isolated to produce neuronal membrane fragments such that the membrane fragments close back on themselves to form synaptosomes that retain functional serotonin transporters. The serotonin transporters concentrate serotonin by transporting it from the fluid in which the synaptosomes are suspended to the interior of the synaptosomes. If the serotonin in the suspension fluid is radiolabeled, then the level of serotonin reuptake can be measured by counting the radioactivity in the synaptosomal pellet obtained by rapid filtration or centrifugation. The ability of a compound to inhibit the level of serotonin reuptake can be determined by adding different concentrations to aliquots of the same synaptosomal preparation. For example, the potency of 3-methoxy-N-methyl-2-(naphthalen-2-yl)-3-phenylpropan-1-amine as an inhibitor of serotonin reuptake can be measured by (1) adding different concentrations of 3-methoxy-N-methyl-2-(naphthalen-2-yl)-3-phenylpropan-1-amine to aliquots of synaptosomes purified from rat brain cortical tissue, (2) adding the same concentration of radiolabeled serotonin to each aliquot, (3) allowing the serotonin transporters to concentrate the radiolabeled serotonin in the synaptosomes, and (4) counting the radioactivity in the synaptosomal pellet of each aliquot obtained after centrifugation. Compounds with a higher potency will more effectively inhibit reuptake at lower concentrations thus resulting in less detectable radioactivity in the synaptosomal pellet.

In another in vitro example, intact cultured mammalian cells expressing a particular recombinant neurotransmitter transporter can be used to assess the ability of a compound to inhibit neurotransmitter reuptake. For example, the potency of 3-chloro-N-methyl-2-(naphthalen-2-yl)-3-phenylpropan-1-amine as an inhibitor of norepinephrine transport can be measured using cultured mammalian cells expressing the norepinephrine transporter. In addition, the potency of a particular compound to inhibit multiple neurotransmitter transporters can be measured. For example, the potency of N,N-dimethyl-3-cyclohexyl-3-hydroxy-2-(2'-naphthyl) propylamine as an inhibitor of both serotonin and norepinephrine transport can be measured using separate cultured mammalian cells expressing the serotonin transporter and cultured mammalian cells expressing the norepinephrine transporter. It is understood that measured neurotransmitter transport levels are compared to controls. Controls include, without limitation, vehicle only as well as known inhibitors such as Prozac®, Paxil® (paroxetine), Effexor® (venlafaxine), or Norpramin® (desipramine).

In addition, the potency of a compound to inhibit the reuptake of different neurotransmitters can be assessed by determining the equilibrium dissociation constant (i.e., $K_d$) of that particular compound for a particular neurotransmitter transporter. Typically, the $K_d$ value is determined as described elsewhere (Tatsumi et al, *Eur. J. Pharmacol.*, 340:249-258 (1997)). Once determined, the $K_d$ value for a particular compound can be used to compare that compound's potency with the potency of other compounds or other known inhibitors. For example, if a particular compound has a $K_d$ of 4.1 nM for the serotonin transporter and a $K_d$ of 12.5 nM for the norepinephrine transporter, then that particular compound can be characterized as having a greater ability to inhibit serotonin reuptake compared to norepinephrine reuptake. Likewise, if a first compound has a $K_d$ of 54 nM for the dopamine transporter and a second compound has a $K_d$ of 134 nM for the dopamine transporter, then the first compound can be characterized as having a greater ability to inhibit dopamine reuptake compared to the second compound.

Various factors can influence the actual effective amount used for a particular application. For example, the frequency of administration, duration of treatment, rate of metabolism of the drug, combination of other compounds, and site of administration may require an increase or decrease in the actual effective amount administered.

The frequency of administration can be any frequency that reduces, prevents, or eliminates an anxiety disorder or depression in a mammal without producing significant toxicity to the mammal. For example, the frequency of administration can be from about once a day to about once a month, or more specifically, from about twice a day to about once a week. In addition, the frequency of administration can remain constant or can be variable during the duration of treatment. As with the effective amount, various factors can influence the actual frequency of administration used for a particular application. For example, the effective amount, duration of treatment, rate of metabolism of the drug, combination of other compounds, and site of administration may require an increase or decrease in administration frequency.

An effective duration for amine compound administration can be any duration that reduces, prevents, or eliminates an anxiety or depressive disorder in a mammal without producing significant toxicity to the mammal. Thus, the effective duration can vary from several days to several weeks, months, or years. In general, the effective duration for the treatment of an anxiety or depressive disorder can range in duration from several days to several years. Once the compound administrations are stopped, however, the treated anxiety or depressive disorder may return. Thus, the effective duration for the prevention of an anxiety or depressive disorder can last in some cases for as long as the individual is alive.

Multiple factors can influence the actual effective duration used for a particular treatment or prevention regimen. For example, an effective duration can vary with the frequency of compound administration, effective compound amount, combination of multiple compounds, and site of administration. It is noted that diagnostic algorithm methods can be devised to determine or reflect appropriate effective doses, durations, and frequencies.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity. Significant toxicity can vary for each particular mammal and each particular composition.

Any combination of compounds provided herein can be administered to a mammal. For example, two compounds can be administered together to a mammal to inhibit norepinephrine reuptake in that mammal. In another example, one or more compounds that can inhibit serotonin reuptake and one or more compounds that can inhibit dopamine reuptake can be administered together to a mammal to inhibit both serotonin and dopamine reuptake in that mammal. The efficacy of such combinations can be assessed using the methods and materials provided herein.

A compound or combination of compounds provided herein can be administered to any part of a mammal's body. For example, a compound can be delivered to, without limitation, spinal fluid, blood, lungs, intestines, muscle tissues, skin, joints, peritoneal cavity, or brain of a mammal. In addition, a compound or combination of compounds can be administered intravenously, intraperitoneally, intramuscularly, subcutaneously, intrathecally, intracerebroventricularly, intradermally, orally, by inhalation, or by gradual perfusion over time. The duration of treatment can be any length of time from as short as one day to as long as the life span of the mammal (e.g., many years). For example, a compound provided herein can be administered daily for three months or ten years. It is also noted that the frequency of treatment can be variable. For example, a compound can be administered once (or twice, three times, etc.) daily, weekly, monthly, or yearly.

The invention will be further described in the following examples, which do not limit the scope of the invention described in the claims.

EXAMPLES

Example 1

Human Transporter Binding Studies

Human embryonic kidney (HEK-293) cells stably transfected and constitutively expressing the human norepinephrine transporter (hNET; Pacholczyk et al., *Nature*, 350:350-354 (1991)), the human dopamine transporter (hDAT; Pristupa et al., *Mol. Pharmacol.*, 45:125-135 (1994)), or the human serotonin transporter (hSERT; Ramamoorthy et al., *Proc. Natl. Acad. Sci. U.S.A.* 90:2542-2546 (1993)) were grown and passaged in 150-mm Petri dishes with 17.5 mL of medium. HEK-293 cells expressing the recombinant hSERT or hDAT were incubated with Dulbecco's modified Eagles medium (MEM) supplemented with 0.1 mM nonessential amino acid solution for MEM, 5% v/v fetal bovine serum and 1 U/mL penicillin/streptomycin solution. Cells expressing the hNET transporter were incubated with Dulbecco's modified Eagles medium supplemented with 10% v/v fetal bovine serum and 100 U/mL penicillin/streptomycin solution and 2 mM L-glutamine. The cells were grown until 70-80% confluent on 175 cm² flasks in a humidified 10% $CO_2$/90% air environment at 37° C., with the selecting antibiotic Geneticin sulfate at 250 µg/mL. The cells were incubated in 10% $CO_2$, 90% air at 37° C. and 100% humidity.

Cell membranes containing hSERT, hNET, or hDAT were prepared from the cell lines to assay ligand binding for each of the transporters. Briefly, the cell medium was removed by aspiration, and the cells were washed with 4 mL modified Puck's D1 solution (solution 1; Richelson et al. in "Methods in Neurotransmitter Receptor Analysis" Yamamura, H. I.; Enna, S. J.; Kuhar, M. J. Eds.; New York, Raven Press, 1990, pp 147-175). The washed cells were incubated for 5 minutes at 37° C. in 10 mL solution 1 containing 100 mM ethylene glycol-bis N,N,N',N'-tetraacetic acid (EGTA). The cells were then scraped from the flask surface with a rubber spatula, placed into a centrifuge tube, and collected by centrifugation at 1000×g for 5 minutes at 4° C. The resulting supernatant was discarded, and the cell pellet was resuspended in 0.5 to 1.0 mL of the appropriate binding buffer (described below). The resuspended cell pellet was homogenized using a Polytron for 10 seconds at setting 6. The resulting homogenate was centrifuged at about 36,000×g for 10 minutes at 4° C. The supernatant was discarded, and the pellet was resuspended in the same volume of the appropriate binding buffer and centrifuged again. The supernatant was discarded, and the final pellet containing cell membranes was resuspended in the appropriate binding buffer and stored at −80° C. until use. The final protein concentration was determined by the Lowry assay using bovine serum albumin as a standard (Lowry et al., *J. Biol. Chem.*, 193:265-275 (1951)).

Radioligand binding assays for the indicated transporters were performed as follows. To assess binding to the cloned hSERT, cells expressing hSERT were homogenized in 50 mM Tris-HCl with 120 mM NaCl and 5 mM KCl (pH 7.4). The binding reaction consisted of 10 µg cell membrane protein, 1.0 nM [$^3$H]citalopram (citalopram, [N-methyl-$^3$H], specific activity 79.0 Ci/mmol; PerkinElmer, Boston, Mass.), and varying concentrations of either unlabeled citalopram or the test compound. A reaction to determine non-specific binding consisted of 10 µg cell membrane protein, 0.5 nM [$^3$H] citalopram, and 1 µM final concentration of unlabeled citalopram. The reactions were incubated at 22° C. for 60 minutes. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman-Coulter, Fullerton, Calif.). Radioactivity was measured with a Beckman liquid scintillation counter (LS 6000TA).

To assess binding to the cloned hNET, cells expressing hNET were homogenized in 50 mM Tris-HCl with 300 mM NaCl and 5 mM KCl (pH 7.4). The binding reaction consisted of 5 µg cell membrane protein, 0.5 nM [$^3$H]nisoxetine (nisoxetine HCl, [N-methyl-$^3$H], specific activity 82.0 Ci/mmol; Amersham, Arlington Hts., Ill.), and varying concentrations of either unlabeled nisoxetine or the test compound. A reaction to determine non-specific binding consisted of 5 µg cell membrane protein, 0.5 nM [$^3$H]nisoxetine, and 1 µM final concentration of unlabeled nisoxetine. The reactions were incubated at 22° C. for 60 minutes. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman-Coulter, Fullerton, Calif.). Radioactivity was measured with a Beckman liquid scintillation counter (LS 6000TA).

To assess binding to the cloned hDAT, cells expressing hDAT were homogenized in 50 mM Tris-HCl with 120 mM NaCl (pH 7.4). The binding reaction contained 15 µg cell membrane protein, 1 nM [$^3$H]WIN35428 (WIN35428, [N-methyl-$^3$H], specific activity 85.9 Ci/mmol; PerkinElmer, Boston, Mass.), and varying concentrations of either unlabeled WIN35428 or the test compound. A reaction to determine non-specific binding contained 15 µg cell membrane protein, 1 nM [$^3$H]WIN35428, and 10 µM final concentration of unlabeled WIN35428. The reactions were incubated at 22° C. for 1 hour. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman-Coulter, Fullerton, Calif.). Radioactivity was measured with a Beckman liquid scintillation counter (LS 6000TA).

Following the radioligand binding assays, the data were analyzed using the LIGAND program (Munson and Rodbard, *Analyt. Biochem.*, 107:220-239 (1980)) to provide values for the equilibrium dissociation constants ($K_d$). The program was modified to calculate the Hill coefficient (nH). Data are presented as geometric mean±S.E.M. of at least three independent experiments. One-component models and two-component models were compared using the root mean square error of each fit and the F test. A low $K_d$ for a compound indicates strong binding to the transporter (i.e., reuptake inhibition).

CYP2D6 $IC_{50}$ values were obtained with the use of a kit from BD Biosciences (CYP2D6/AMMC; Cat. No. 459200, BD Biosciences, San Jose, Calif.) according to the manufacturer's instructions. This kit includes the use of a fluorescent P450 substrate (AMMC or 3-[2-(N,N-diethyl-N-methylamino)ethyl]-7-methoxy-4-methylcoumarin) and recombinant human P450. Quinidine was used as the positive control inhibitor.

Human "ether-a-go-go" (hERG) is an ion channel. Blockade of this channel can be predictive of causing cardiac arrhythmias in humans. hERG assays were performed to measure the ability of a compound to block rubidium ion ($Rb^+$) efflux from cells expressing hERG. Cells were preloaded with $Rb^+$, incubated with test compound, and then exposed to a buffer that opens the channel and allows the efflux of ions. Compounds as powder were dissolved in 100% DMSO to prepare 100 mM stock solutions. These stocks were subsequently used to prepare eight stock concentrations at 100× in 100% DMSO (Sigma Chemical Co., Cat #D-8418). The stocks were stored at 23° C. Astemizole (Sigma Chemical Co. Cat #A-6424) was used as positive control.

Eight doses in duplicate were tested for astemizole (range 1 nM to 3000 nM) and for test compounds (Table 2; PRC200-SS, MCJ001-Cl-SS, MCJ001-F—RS, MCJ001-F—SR, MCJ001-F—SS, MCJ001-N3-RS, MCJ001-OAc-SS, MCJ002-NH2-SS, and MCJ001-OMe-SS). The range of doses for the test compounds was 30 nM through 100,000 nM. The results reveal that MCJ001-Cl-SS, MCJ001-F—RS, MCJ001-F—SR, MCJ001-F—SS, MCJ001-N3-RS, MCJ001-OAc-SS, MCJ002-NH2-SS, and MCJ001-OMe-SS are weaker than PRC200-SS at blocking this channel (Table 2). None was close to the potency of astemizole.

HCl salts of the test compounds listed in Table 1 were made and tested as described herein.

TABLE 1

Test compounds.

| Compound Name | Simple Name | Molecular Weight |
|---|---|---|
| (1S,2S)-3-(methylamino)-2-(naphthalen-2-yl)-1-phenylpropan-1-ol | PRC200-SS | 327.85 |
| Dimer of PRC200-SS | MCJ001-Dimer5-SS | 723.81 |
| (2R,3R)-3-chloro-N-methyl-2-(naphthalen-2-yl)-3-phenylpropan-1-amine | MCJ001-Cl-RR | 346.29 |
| (2R,3S)-3-chloro-N-methyl-2-(naphthalen-2-yl)-3-phenylpropan-1-amine | MCJ001-Cl-SR | 346.29 |
| (2S,3S)-3-chloro-N-methyl-2-(naphthalen-2-yl)-3-phenylpropan-1-amine | MCJ001-Cl-SS | 346.23 |
| (2R,3R/2S,3S)-3-fluoro-N-methyl-2-(naphthalen-2-yl)-3-phenylpropan-1-amine | MCJ001-F-(±)-RR | 329.85 |
| (2R,3R)-3-fluoro-N-methyl-2-(naphthalen-2-yl)-3-phenylpropan-1-amine | MCJ001-F-RR | 329.84 |

TABLE 1-continued

Test compounds.

| Compound Name | Simple Name | Molecular Weight |
|---|---|---|
| (2S,3R)-3-fluoro-N-methyl-2-(naphthalen-2-yl)-3-phenylpropan-1-amine | MCJ001-F-RS | 329.85 |
| (2R,3S)-3-fluoro-N-methyl-2-(naphthalen-2-yl)-3-phenylpropan-1-amine | MCJ001-F-SR | 329.85 |
| (2S,3S)-3-fluoro-N-methyl-2-(naphthalen-2-yl)-3-phenylpropan-1-amine | MCJ001-F-SS | 329.85 |
| (2S,3R)-3-azido-N-methyl-2-(naphthalen-2-yl)-3-phenylpropan-1-amine | MCJ001-N3-RS | 352.86 |
| (2R,3S)-3-azido-N-methyl-2-(naphthalen-2-yl)-3-phenylpropan-1-amine | MCJ001-N3-SR | 352.86 |
| (2R,3R)-N1-methyl-2-(naphthalen-2-yl)-3-phenylpropane-1,3-diamine | MCJ001-NH2-(±)-RR | 363.32 |
| (2S,3R)-N1-methyl-2-(naphthalen-2-yl)-3-phenylpropane-1,3-diamine | MCJ001-NH2-RS | 363.32 |
| (2R,3S)-N1-methyl-2-(naphthalen-2-yl)-3-phenylpropane-1,3-diamine | MCJ001-NH2-SR | 363.32 |
| (1S,2S)-3-(methylamino)-2-(naphthalen-2-yl)-1-phenylpropyl acetate | MCJ001-OAc-SS | 369.88 |
| (2R,3S/2S,3R)-3-methoxy-N-methyl-2-(naphthalen-2-yl)-3-phenylpropan-1-amine | MCJ001-OMe-(±)-SR | 341.85 |
| (2S,3S)-3-methoxy-N-methyl-2-(naphthalen-2-yl)-3-phenylpropan-1-amine | MCJ001-OMe-SS | 341.85 |
| (4S,5S)-1-methyl-5-(naphthalen-2-yl)-4-phenylhexahydropyrimidine | MCJ001-NH2-Cyc-SS | 375.33 |
| (2S,3S)-N1,N1-dimethyl-2-(naphthalen-2-yl)-3-phenylpropane-1,3-diamine | MCJ002-NH2-SS | 377.32 |
| (2S,2'S,3S,3'S)-3,3'-(butane-1,4-diylbis(oxy))bis(N-methyl-2-(naphthalen-2-yl)-3-phenylpropan-1-amine) | MCJ001-Dimer4-SS | 709.78 |
| (5S,6S)-3-methyl-5-(naphthalen-2-yl)-6-phenyl-1,3-oxazinane | MCJ001-OH-Cyc-SS | 339.8 |
| (4S,5S)-1,1-dimethyl-5-(naphthalen-2-yl)-4-phenylhexahydropyrimidin-1-ium chloride | MCJ002-NH2-Cyc-SS | 389.9 |
| (5R,6R)-3-methyl-5-(naphthalen-2-yl)-6-phenyl-1,3-oxazinane | MCJ001-OH-Cyc-RR | 339.8 |
| (5S,6S)-5-(naphthalen-2-yl)-6-phenyl-1,3-oxazinane | MCJ000-OH-Cyc-SS | 325.8 |
| (2S,3R)-3-chloro-N-methyl-2-(naphthalen-2-yl)-3-phenylpropan-1-amine | MCJ001-Cl-RS | 346.3 |

Human transporter binding data are presented in Table 2 for the test compounds listed in Table 1. Compared to PRC200-SS, MCJ001-NH2-Cyc-SS had a markedly enhanced potency at binding to hSERT, a several fold enhanced potency at binding to hDAT, and lower potency of binding to hNET. This compound therefore had a different rank-order of potency (S>D>N) from that of PRC200 (N>S>D). In fact, 19 of the 25 compounds had a different rank-order of potency from that of PRC200. Nine compounds (MCJ001-NH2-cyc-SS, MCJ001-F—SS, MCJ001-Cl-SS, MCJ001-Cl-RS, racemic MCJ001-NH2-(±)-RR, MCJ001-OH-Cyc-SS, MCJ002-NH2-Cyc-SS, MCJ002-NH2-SS, MCJ001-F—RS, and racemic MCJ001-F-(±)-RR) exhibited greater binding at hSERT than that observed with PRC200-SS. Also, MCJ002-NH2-SS, MCJ001-NH2-Cyc-SS, and MCJ001-Cl-RS exhibited several fold more potent binding at hDAT, when compared to PRC200-SS. Enhanced binding to hDAT over that for PRC200-SS was also found with MCJ002-NH2-Cyc-SS, MCJ001-F—RS, and MCJ001-F—SS. MCJ001-F—SR is unique, since it potently binds to hDAT, in the range of that seen with PRC200-SS, while much more weakly at hNET and hSERT than that exhibited by PRC200-SS. As a result, the rank-order of potency of MCJ001-F—SR is D>S>N. Additionally, for 22 of the 25 compounds (the exceptions being MCJ001-Cl-SS, MCJ001-NH2-cyc-SS, and MCJ002-NH2-Cyc-SS), the structural changes narrowed the range of the potencies at the three human transporters. While PRC200-SS has a difference of 45 fold between its most potent binding (hNET) and its least potent binding (hDAT), for each compound but three, this range is smaller. For example, for MCJ002-NH2-SS, the range was 5.3, making it more likely that at a given dosage, there will be significant binding at the three transporters. More specifically, as an example, and assuming minimal competition from endogenous neurotransmitter, when MCJ002-NH2-SS occupies 95% of hSERT binding sites, a calculation based on occupancy theory gives the result that it will occupy 79% of hNET and 92% of hDAT binding sites.

Cytochrome P450 2D6 (CYP2D6) is a drug-metabolizing enzyme that breaks down a very large percentage of drugs given to patients. Potently inhibiting this enzyme, as seen with PRC200-SS (Table 2), has the potential of inhibiting, in patients, the metabolism of other drugs that the patient may be taking This pharmacokinetic interaction can affect the dosing of the other drugs and potentially can lead to serious consequences as a result of too high blood levels of the other drugs. Some of the compounds of Table 2 have been tested for CYP2D6 inhibition. Modifications to PRC200-SS, which potently inhibited CYP2D6, markedly reduced the potency of inhibition at CYP2D6 of MCJ001-F—RS, MCJ001-N3-RS, MCJ001-NH2-SR, MCJ001-OAc-SS, and MCJ001-OMe-SS. These results demonstrate that MCJ001-F—RS, MCJ001-N3-RS, MCJ001-NH2-SR, MCJ001-OAc-SS, and MCJ001-OMe-SS can have markedly different pharmacokinetic drug interactions than those observed with PRC200-SS.

TABLE 2

Human transporter binding data.

| | Equilibrium Dissociation Constant ($K_D$) for Transporter Binding (Geometric Mean; nM ± SEM) | | | | Mean Potency Range | CYP2D6 ($IC_{50}$, nM) | hERG ($IC_{50}$, μM) |
|---|---|---|---|---|---|---|---|
| Simple Name | hSERT (S) | hNET (N) | hDAT (D) | Potency | | | |
| PRC200-SS | 3.8 ± 0.3 | 0.6 ± 0.2 | 27 ± 3 | N > S > D | 45 | 80 | 32.6 |
| MCJ001-Cl-RR | 35 ± 2 | 234 ± 5 | 290 ± 20 | S > N > D | 8.3 | | |
| MCJ001-Cl-SR | 55 ± 5 | 700 ± 50 | 350 ± 20 | S > D > N | 13 | | |
| MCJ001-Cl-SS | 1.1 ± 0.1 | 3.7 ± 0.5 | 78 ± 5 | S > N > D | 71 | | 45.4 |
| MCJ001-Dimer5-SS | 140 ± 30 | 160 ± 30 | 113 ± 6 | D > S > N | 1.4 | | |

TABLE 2-continued

Human transporter binding data.

| Simple Name | Equilibrium Dissociation Constant ($K_D$) for Transporter Binding (Geometric Mean; nM ± SEM) | | | Potency | Potency Range | Mean CYP2D6 ($IC_{50}$, nM) | hERG ($IC_{50}$, µM) |
| --- | --- | --- | --- | --- | --- | --- | --- |
| | hSERT (S) | hNET (N) | hDAT (D) | | | | |
| MCJ001-F-(±)-RR | 3.9 ± 0.1 | 4.5 ± 0.8 | 140 ± 10 | S > N > D | 36 | | |
| MCJ001-F-RR | 16 ± 1 | 170 ± 10 | 150 ± 9 | S > D > N | 11 | | |
| MCJ001-F-RS | 2.8 ± 0.3 | 0.9 ± 0.1 | 19 ± 2 | N > S > D | 21 | 160 | 92.4 |
| MCJ001-F-SR | 130 ± 20 | 430 ± 70 | 36 ± 6 | D > S > N | 12 | | 94.0 |
| MCJ001-F-SS | 0.82 ± 0.09 | 1.3 ± 0.2 | 23.5 ± 0.9 | S > N > D | 29 | 60 | 51.8 |
| MCJ001-N3-RS | 124 ± 9 | 64 ± 7 | 190 ± 20 | N > S > D | 3.0 | 4000 | 39.2 |
| MCJ001-N3-SR | 380 ± 40 | 700 ± 100 | 1440 ± 70 | S > N > D | 3.8 | | |
| MCJ001-NH2-(±)-RR | 1.27 ± 0.06 | 2.5 ± 0.1 | 28 ± 4 | S > N > D | 22 | | |
| MCJ001-NH2-cyc-SS | 0.26 ± 0.02 | 13 ± 1 | 7.7 ± 0.6 | S > D > N | 50 | | |
| MCJ001-NH2-RS | 100 ± 7 | 78 ± 4 | 380 ± 30 | N > S > D | 4.9 | | |
| MCJ001-NH2-SR | 180 ± 10 | 166 ± 8 | 260 ± 20 | N > S > D | 1.6 | 4100 | |
| MCJ001-OAc-SS | 55 ± 6 | 44 ± 5 | 150 ± 20 | N > S > D | 3.4 | 600 | 78.8 |
| MCJ001-Ome-(±)-SR | 710 ± 50 | 580 ± 70 | 600 ± 100 | N = D > S | 1.2 | | |
| MCJ001-Ome-SS | 13 ± 2 | 1.4 ± 0.2 | 40.6 ± 0.8 | N > S > D | 29 | 400 | 84.8 |
| MCJ002-NH2-SS | 2.4 ± 0.3 | 12.6 ± 0.9 | 4.2 ± 0.2 | S > D > N | 5.3 | | 67.9 |
| MCJ001-Dimer4-SS | 94 ± 10 | 259 ± 5 | 240 ± 1 | S > D > N | 2.8 | | |
| MCJ001-OH-Cyc-SS | 1.8 ± 0.2 | 2.7 ± 0.3 | 52 ± 5 | S > N > D | 29 | | |
| MCJ002-NH2-Cyc-SS | 1.9 ± 0.2 | 100 ± 10 | 18 ± 2 | S > D > N | 53 | | |
| MCJ001-OH-Cyc-RR | 240 ± 20 | 460 ± 50 | 180 ± 20 | D > S > N | 2.6 | | |
| MCJ000-OH-Cyc-SS | 8 ± 1 | 99 ± 6 | 330 ± 50 | S > D > N | 41 | | |
| MCJ001-Cl-RS | 1.1 ± 0.1 | 10.4 ± 0.4 | 7.9 ± 0.4 | S > D > N | 9.5 | | |
| Desipramine | 17.6 ± 0.7 | 0.83 ± 0.05 | 3190 ± 40 | N > S > D | | | |
| Duloxetine | 0.22 ± 0.06 | 4.2 ± 0.4 | 840 ± 90 | S > N > D | | | |
| Fluoxetine | 0.81 ± 0.02 | 240 ± 10 | 3600 ± 100 | S > N > D | | | |
| Imipramine | 1.4 ± 0.03 | 37 ± 2 | 8500 ± 100 | S > N > D | | | |
| Milnacipran | 9 ± 1 | 80 ± 10 | >10000 | S > N > D | | | |
| Nomifensine | 1010 ± 30 | 16.0 ± 0.4 | 56 ± 3 | N > D > S | | | |
| Paroxetine | 0.13 ± 0.01 | 40 ± 2 | 490 ± 20 | S > N > D | | | |
| Reboxetine | 57.5 ± 0.6 | 7.2 ± 0.8 | >10000 | N > S > D | | | |
| Sertraline | 0.29 ± 0.01 | 420 ± 20 | 25 ± 2 | S > D > N | | | |
| Venlafaxine | 9.0 ± 0.3 | 1060 ± 40 | 9300 ± 50 | S > N > D | | | |
| Quinidine (CYP2D6 reference inhibitor) | — | — | — | — | — | 12.9 | |
| Astemizole (hERG reference inhibitor) | — | — | — | — | — | — | 0.041 |

Reference compounds (Tatsumi et al, *Eur. J. Pharmacol.*, 340: 249-258 (1997) and E. Richelson, unpublished data - duloxetine, milnacipran, and reboxetine).

Example 2

Inhibition of Transport into Whole Cells Expressing Human Transporters

HEK-293 cells were grown in 175 cm² culture flasks. Medium was removed, and cells washed with phosphate-buffered saline (PBS). Transport buffer (10.5 mM HEPES, pH 7.4, 128 mM NaCl, 4.96 mM KCl, 1.2 mM KH$_2$PO$_4$, 1.2 mM MgSO$_4$, 2.3 mM CaCl$_2$, 10 mM glucose, 10 µM pargyline, 0.2 mg/mL sodium ascorbate) was added, and cells gently scraped. Cell clusters were separated by trituration with a pipette for 5-10 aspirations and ejections. Aliquots (50 µL) of the suspended cells were added to assay tubes containing drug and transport buffer in a final volume of 0.5 mL. Compounds were tested in duplicate over 11 concentrations spanning 6 orders of magnitude. Following a 30 minute pre-incubation in a 37° C. water bath, [³H]-neurotransmitter (10 nM final concentration) was added, and the mixture was incubated for a further 10 minutes. Transport was stopped by the addition of 4 mL ice-cold wash buffer consisting of 0.9% (w/v) sodium chloride. The contents of each test tubes were then rapidly filtered through a Whatman GF/B glass fiber filter (pre-soaked in 0.2% [w/v] polyethylimine) in a 48-place Brandel cell harvester. The filters containing deposited cells and bound radioactivity were then rapidly washed with an additional 8 mL of wash buffer. The washed filters were placed in a scintillation vial containing 5 mL of Redi-Safe (Beckman Instruments, Fullerton, Calif.). Radioactivity was measured with a Beckman liquid scintillation counter (LS 6000TA). Specific transport was calculated as the difference between the total transport (zero unlabelled neurotransmitter) and nonspecific transport (excess unlabelled neurotransmitter).

The data for inhibition of neurotransmitter transport into cells expressing the human transporters inhibition data are presented in Table 3 for some of the compounds listed in Table 1.

TABLE 3

Inhibition of neurotransmitter transport into cells expressing the human transporters.

| Simple name | Inhibitor Constant ($K_i$, Geometric Mean; nM ± SEM) | | | Potency |
| --- | --- | --- | --- | --- |
| | 5-HT | NE | DA | |
| PRC200-SS | 2.8 ± 0.4 | 6 ± 2 | nd | nd |
| MCJ001-Dimer5-SS | 14 ± 2 | 720 (n = 1) | 52 (n = 2) | S > D > N |
| MCJ001-F-(±)-RR | 18 ± 3 | 2.1 ± 0.5 | 33 ± 1 | N > S > D |
| MCJ001-F-RS | 3.5 ± 0.9 | 4.8 (n = 1) | 30 ± 5 | S > N > D |
| MCJ001-F-SR | 150 (n = 2) | nd | nd | nd |
| MCJ001-N3-RS | 48 ± 10 | 24 ± 4 | 64 (n = 2) | N > S > D |

TABLE 3-continued

Inhibition of neurotransmitter transport into cells expressing the human transporters.

| Simple name | Inhibitor Constant ($K_i$, Geometric Mean; nM ± SEM) | | | Potency |
|---|---|---|---|---|
| | 5-HT | NE | DA | |
| MCJ001-N3-SR | 46 ± 6 | 1400 (n = 1) | 77 (n = 1) | S > D > N |
| MCJ001-OMe-(±)-SR | 60 ± 7 | 20 ± 1 | 2400 (n = 1) | N > S > D |
| MCJ001-OMe-SS | 12 ± 2 | 1.2 ± 0.2 | 21 ± 3 | N > S > D |
| 5-HT | 700 ± 200 | | | |
| NE | | 6000 ± 1000 | | |
| DA | | | 3400 ± 700 | | nd = not determined

Example 3

Neurotransmitter Reuptake in Rat Brain Synaptosomes

Rat synaptosomal preparations were prepared from frontal and occipital cortical tissues for transport of serotonin and norepinephrine, respectively, and striatal tissues for transport of dopamine. Tissues were dissected from freshly decapitated male Sprague-Dawley rats (125-250 g; Harlan Sprague-Dawley, Indianapolis, Ind., USA). The dissected tissues were separately homogenized in 20 volumes (cortical) or 40 volumes (striatal) of ice-cold, oxygenated HEPES buffer 0.32 M sucrose containing 11 mM glucose (pH 7.4) in a glass Potter-Elvehjem homogenizer with Teflon® pestle (8 strokes, 900 rpm). The homogenates were centrifuged at 1,000×g for 10 minutes. The resulting supernatant was decanted and further centrifuged at 20,000×g for 20 minutes at 4° C. The supernatant was discarded, and the synaptosomes contained in the pellet were gently resuspended in oxygenated incubation buffer containing 10.5 mM HEPES (pH 7.4), 128 mM NaCl, 4.96 mM KCl, 1.2 mM KH2PO4, 1.2 mM $MgSO_4$, 2.3 mM $CaCl_2$, 10 mM dextrose, 10 μM pargyline, and 0.2 mg/mL sodium ascorbate (pH 7.4). The synaptosomal protein concentration was determined by using the BCA assay (Pierce Biotechnology Inc, Rockford, Ill.), according to the manufacturer's instructions. Synaptosomal protein (1.0-2.5 mg) was suspended in 1 mL oxygenated incubation buffer as defined above. Test amine compound was pre-incubated with the synaptosomal preparation for 30 minutes at 37° C. in a shaking water bath (80 oscillations/minute). After preincubation, the neurotransmitter reuptake reaction was initiated by the addition of 8 nM levo-[ring-2,5,6-$^3$H]norepinephrine ([$^3$H]NE; 54.6 Ci/mmol; PerkinElmer, Boston, Mass.), 4 nM 5-[1,2-3H (N)]hydroxytryptamine creatine sulfate ([$^3$H]5-HT; 30.0 Ci/mmol; PerkinElmer), or 2 nM [7,8-$^3$H]dopamine (DA) ([$^3$H]DA; 45 Ci/mmol; PerkinElmer. The reaction was stopped after 10 minutes by adding 4 mL ice-cold 0.9% (w/v) sodium chloride. The stopped reactions were rapidly filtered through a Whatman GF/B glass fiber filter (pre-soaked in 0.2% (w/v) polyethylimine) in a 48-place Brandel cell harvester. The filters containing deposited synaptosomes were then washed with an additional 8 mL of wash buffer. The washed filters were placed in a scintillation vial containing 5 mL of Redi-Safe (Beckman Instruments, Fullerton, Calif.) and counted. Specific reuptake was calculated as the difference between the total reuptake (zero unlabelled ligand) and nonspecific reuptake (excess unlabelled ligand).

TABLE 4

Inhibition of neurotransmitter transport into rat brain synaptosomal preparations.
Inhibitor Constant ($K_i$, Geometric Mean; nM ± SEM)

| Simple name | Ki (nM) | | | Potency |
|---|---|---|---|---|
| | 5HT | NE | DA | |
| PRC200-SS | 2.12 ± 0.9 | 6 ± 2 | 61 ± 4 | S > N > D |
| MCJ001-Dimer5-SS | 150 ± 10 | 200 ± 30 | 800 ± 300 | S > N > D |
| MCJ001-F-(±)-RR | 90 ± 7 | 47 ± 5 | 250 ± 9 | N > S > D |
| MCJ001-F-RS | 9.0 ± 1.5 | 9 ± 1 | 58 ± 6 | S = N > D |
| MCJ001-F-SR | 53 ± 12 | 110 ± 20 | 130 ± 20 | S > N > D |
| MCJ001-N3-RS | 88 ± 10 | 56 ± 3 | 270 ± 50 | N > S > D |
| MCJ001-N3-SR | 640 ± 50 | 250 ± 20 | 2000 ± 300 | N > S > D |
| MCJ001-OMe-(±)-SR | 90 ± 36 | 210 ± 30 | 1030 ± 30 | S > N > D |
| MCJ001-OMe-SS | 12.8 ± 0.9 | 24 ± 2 | 46 ± 5 | S > N > D |
| Imipramine* | 41 ± 3 | 14 ± 1 | 11000 ± 1000 | N > S > D |
| Nomifensine# | 1280 ± 80 | 5.0 ± 0.4 | 51 ± 8 | N > D > S |
| Paroxetine* | 0.73 ± 0.04 | 33 ± 2 | 1700 ± 300 | S > N > D |
| Sertraline* | 3.4 ± 0.4 | 220 ± 40 | 260 ± 40 | S > N = D |
| Venlafaxine* | 39 ± 3 | 210 ± 20 | 5300 ± 600 | S > N > D |
| 5-HT | 18 ± 3 | | | |
| NE | | 160 ± 20 | | |
| DA | | | 62 ± 4 | |

*Bolden-Watson and Richelson, Life Sci., 52: 1023-1029 (1993)
Richelson and Pfenning, Eur. J. Pharmacol. 104: 277-286 (1984)

Comparison of the data of Tables 3 and 4 reveals that some compounds may exhibit species selectivity between human and rat in the transporter studied.) Specifically, MCJ001-N3-SR and MCJ001-Dimer5-SS appear to be much more potent at blocking transport by the human serotonin and dopamine transporters in cells expressing these transporters than by the rat serotonin and dopamine transporters in synaptosomal preparations.

Example 4

Assessing Antidepressant Activity

A tail suspension test in mice similar to that described elsewhere (Stem et al., Psychopharmacology (Berl), 85:367-370 (1985)) can corroborate the results found using the forced swim test, with possible sensitivity to a broader range of antidepressants. When mice are suspended by their tail, there is an initial period of agitation, followed by immobility. This test identifies antidepressant compounds, which decrease the duration of immobility.

Figures 10A, 10B, 10C, 10D:
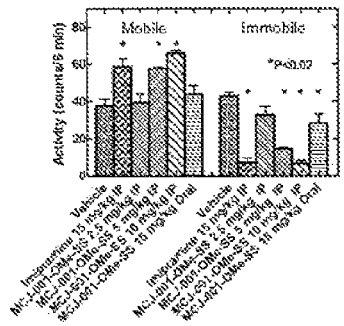
FIGS. 10A-D contain graphs plotting activity levels (counts/6 minutes) for mice treated with the indicated compound at the indicated amount.
Figure 10E:
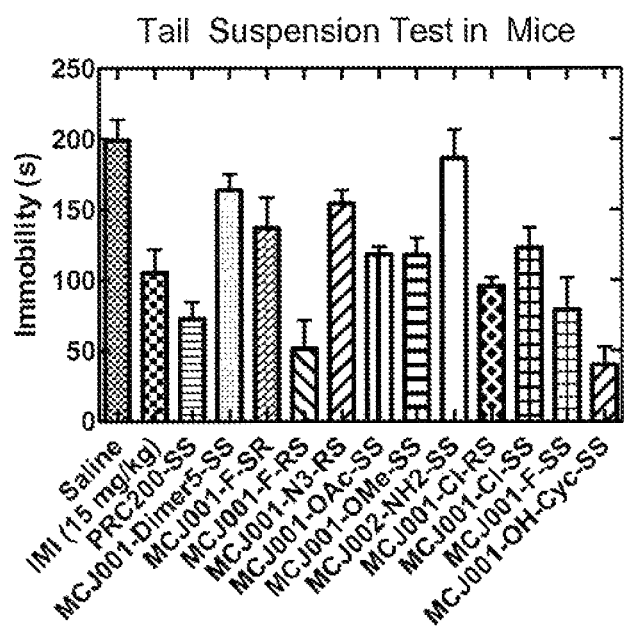
FIG. 10E is a graph plotting the duration of immobility (seconds) during a tail suspension test of mice intraperitoneally treated with 5 mg/kg of the indicated compound, except that imipramine was administered at 15 mg/kg. Compound-treated groups of mice exhibited a statistically different ($P \leq 0.03$) immobility result as compared to the group of mice treated with saline, except for the groups treated with MCJ001-Dimer5-SS or MCJ002-NH2-SS. Each group of mice included between three and seven mice.
Figure 10F:
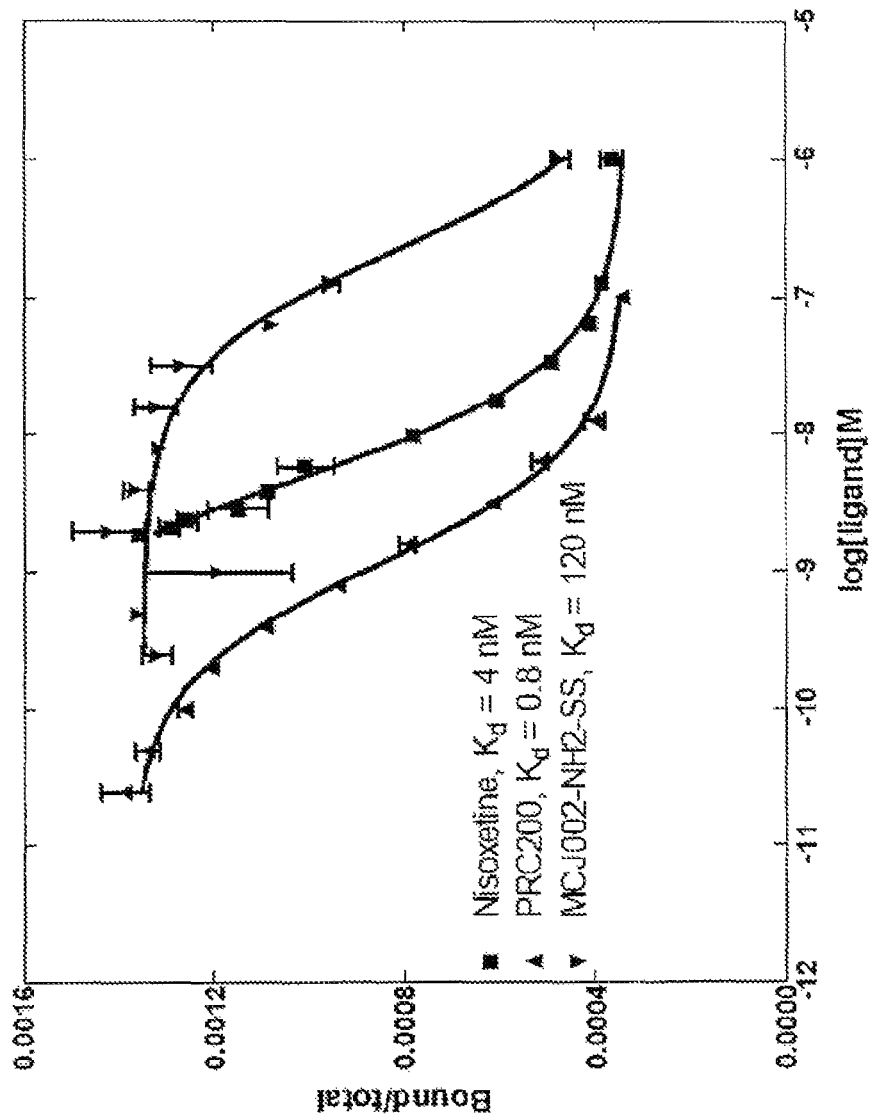
FIGS. 10F is a line graph plotting the competition binding of the indicated compound against [$^3$H]nisoxetine for mouse hippocampus tissue.
Figure 10G:
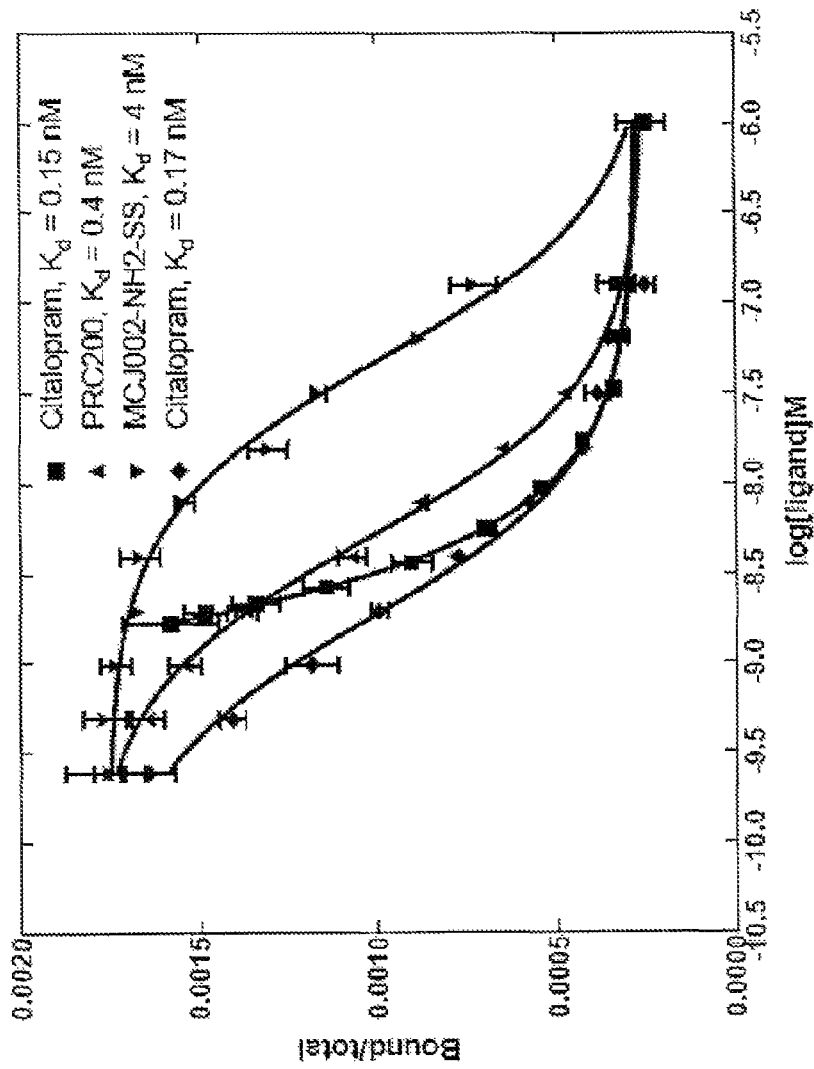
FIGS. 10G is a line graph plotting the competition binding of the indicated compound against [$^3$H]citalopram for mouse cortex tissue.
Figure 10H:
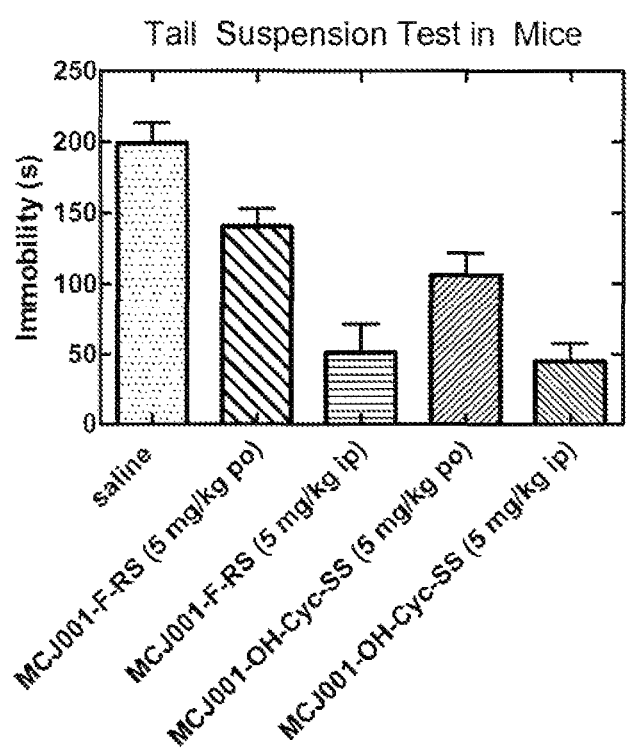
FIG. 10H is a bar graph plotting the duration of immobility (seconds) during a tail suspension test of mice intraperitoneally (ip) or per os (po; orally) treated with 5 mg/kg of the indicated compound. Compound-treated groups of mice exhibited a statistically different ($P \leq 0.01$) immobility result as compared to the group of mice treated with saline. Groups of mice treated intraperitoneally with a particular compound exhibited statistically ($P \leq 0.01$) shorter immobility times than the groups of mice treated orally with the same compound. Each group of mice included between seven and nine mice.

Test compounds were prepared by formulating the compounds with a pharmaceutically acceptable carrier such as saline. To determine the potential antidepressant effects of some of these compounds, male C57BL/6J mice (22-32 g) were injected with either MCJ001-OMe-SS, MCJ001-F—RS, MCJ001-F—SR, or MCJ001-F-(±)-RR at doses ranging between 1 mg/kg and 10 mg/kg, imipramine (15 mg/kg) intraperitoneally (IP) as a positive control, or saline/vehicle 30 minutes before testing. Additionally, MCJ001-OMe-SS (15 mg/kg) was given by gastric gavage to test its effects orally. Each mouse was then subjected to the tail-suspension test (TST). Each mouse (n>3) was suspended by its tail 45 cm above the table top with the use of adhesive tape placed 1 cm from the tip of its tail. Behavior was scored every 5 seconds throughout the 6-minute test as either mobile or immobile (FIG. 10A-D) or total duration of immobility during the 6-minute test (FIGS. 10E and 10H). Mice were considered immobile only when hanging passively and completely motionless. Scores for each behavior were expressed as total counts per 6-minute session. Imipramine (15 mg/kg IP) and MCJ001-OMe-SS at 5 and 10 mg/kg IP significantly (P<0.02) increased mobility, and imipramine (15 mg/kg IP) and MCJ001-OMe-SS at 5 and 10 mg/kg IP and at 15 mg/kg orally significantly (P<0.02) reduced immobility (FIG. 10A). MCJ001-F—RS at 2.5 and 5 mg/kg IP significantly (P<0.005) increased mobility, and MCJ001-F—RS at 1, 2.5, and 5 mg/kg IP significantly (P<0.005) reduced immobility (FIG. 10B). MCJ001-F—SR at 10 mg/kg IP significantly (P≦0.033) increased mobility, and MCJ001-F—SR at 10 mg/kg IP significantly (P<0.033) reduced immobility (FIG. 10C). MCJ001-F-(±)-RR at 5 and 10 mg/kg IP significantly (P≦0.016) increased mobility, and MCJ001-F-(±)-RR at 5 and 10 mg/kg IP significantly (P≦0.016) reduced immobility (FIG. 10D).

In another study that measured the duration of immobility in the tail suspension test with mice, all compounds indicated in FIG. 10E at 5 mg/kg IP, except MCJ002-NH2-SS and MCJ001-Dimer5-SS, significantly reduced the time that the animals were immobile compared to saline (FIG. 10E).

In another study that also measured duration of immobility in the tail suspension test with mice, all compounds indicated in FIG. 10H either IP or PO significantly (P<0.01) reduced the time that the animals were immobile compared to saline (FIG. 10H). In addition, for each compound indicated in FIG. 10H, the IP route of administration significantly (P<0.01) reduced the time that the animals were immobile compared to the compound by the PO route, respectively (FIG. 10H).

Since MCJ002-NH2-SS was potent at human transporters (Table 2) and exhibited antidepressant-like activity in the rat forced swim test (FIG. 12A), this result suggested that it was less potent at some transporter in mouse. Radioligand binding studies with the use of mouse brain tissue indicated that MCJ002-NH2-SS was 10 fold weaker at the mouse NET (FIG. 10F) as compared to its potency at human NET (Table 2), while having about the same potency at mouse SERT (FIG. 10G), as that for human SERT.

Figure 11:
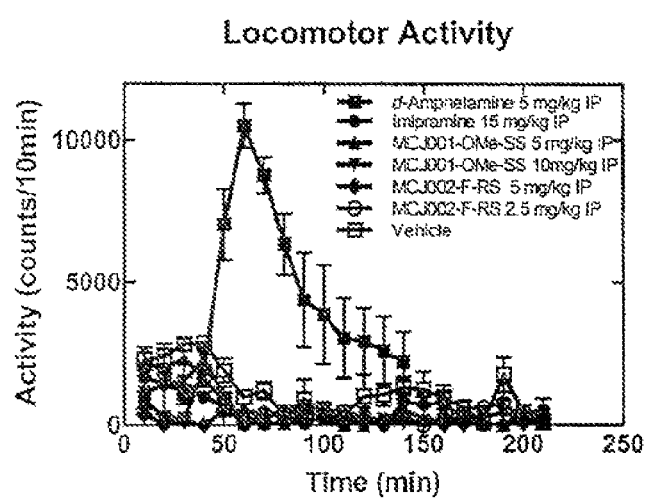
FIG. 11 is a graph plotting activity levels (counts/10 minutes) for mice treated with the indicated compound at the indicated amount.

If a compound increases locomotor activity, as do psychostimulants such as d-amphetamine, then the results of the tail-suspension test may be invalid. Therefore, mice were tested in a Plexiglas Opto-Varimex Minor motility chamber (Columbus Instruments, Columbus Ohio) to determine whether compounds exhibiting a positive effect in the TST affected locomotor activity. Animals were acclimated to the test chamber for 2 hours. After a 30 minute session of baseline readings, animals (n≧3) were injected with either MCJ001-OMe-SS or MCJ001-F—RS at doses that exhibited positive effects in the TST, and activity was measured in 10 minute intervals for 3 hours. For comparison, other mice were injected with imipramine (15 mg/kg IP), d-amphetamine (5 mg/kg IP), or vehicle. Only d-amphetamine caused a significant effect on locomotor activity (FIG. 11).

When rats are placed in a cylinder of water from which they cannot escape, they will remain immobile in the water for the majority of the test. Administration of antidepressants to rats decreases the amount of time spent immobile and increases swimming activity in the chamber (Porsolt et al., *Nature*, 266:730-732 (1977)). This test can be used to screen compounds for potential antidepressant activity (Cryan et al., *Trends Pharmacol. Sci.*, 23:238-245 (2002)).

Male Sprague-Dawley rats (200-250 g) were individually placed in vertical cylinders (height 40 cm, internal diameter 19 cm) containing water (25° C.) to a level of 15 cm, as described elsewhere (Porsolt et al., *Nature*, 266:730-732 (1977)). Water was changed between trials, and the procedure involved a pretest and a 5-minute test separated by 24 hours. During the pretest, rats (adapted to the experimental room for no less than one hour) were placed in the cylinder for 15 minutes. Following this initial exposure, the rats were dried with towels and transferred to a "drying cage" situated under a warming lamp. Fifteen minutes later, rats were injected IP with imipramine (15 mg/kg) as a positive control, a test compound (5 mg/kg), or saline, and were returned to their home cages. The following day, rats were transferred to the experimental room and acclimated for at least one hour. Rats were injected with imipramine (15 mg/kg), a test compound (5 mg/kg), or saline both five hours and 30 minutes before testing, and then were placed in the test chambers.

A time sampling technique was used to score behavior every five seconds during the five minute test period as described elsewhere (Detke et al., *Psychopharmacology (Berl)*, 121:66-72 (1995)). At the end of each 5-second interval, the rat's behavior was observed and scored based on the criteria described elsewhere (Porsolt et al., *Nature*, 266:730-732 (1977)). The rat was considered immobile when floating motionless or making only those movements necessary to keep its head above the surface of the water. Scores for each behavior (swimming or immobility) were expressed as total counts per 5-minute session. Statistical analysis was performed using ANOVA followed by the Tukey test for post-hoc comparisons.

Figure 12A:
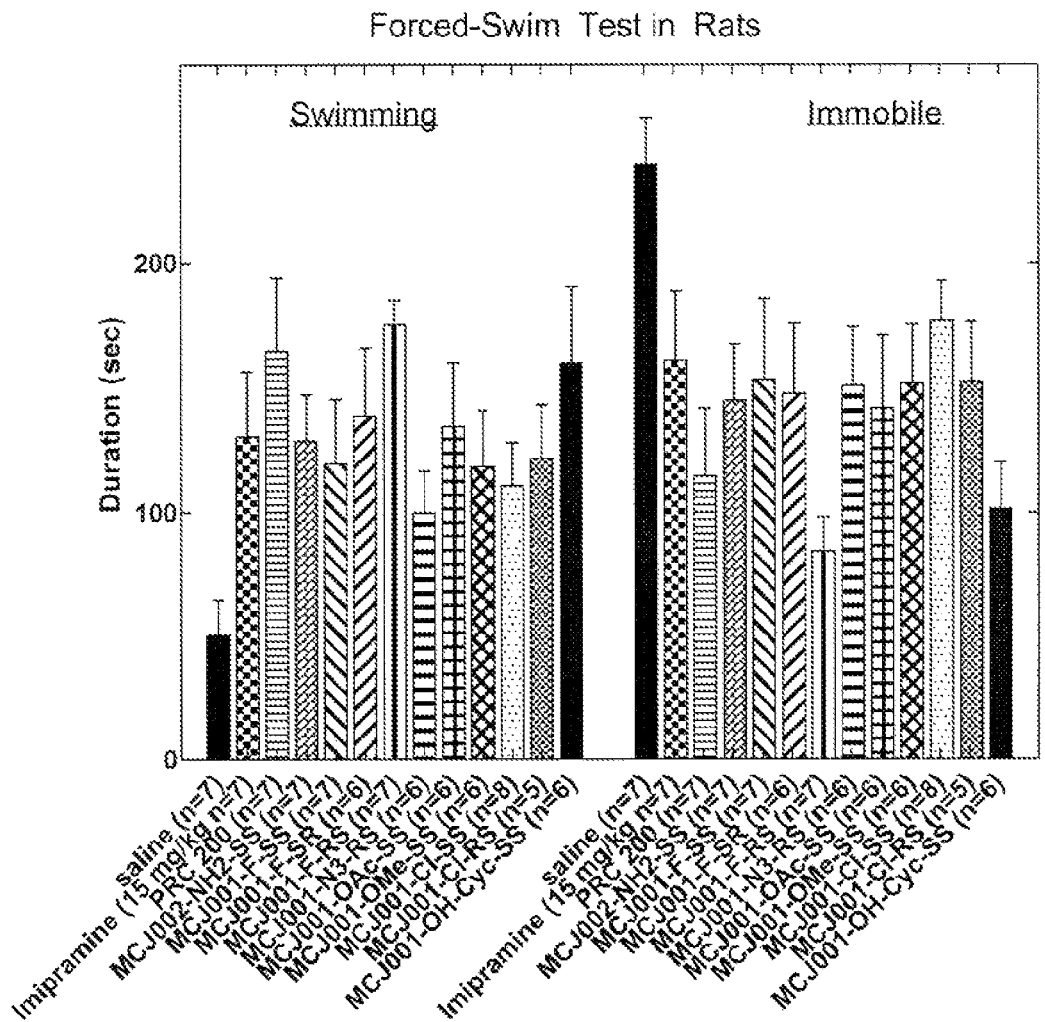
FIG. 12A is a graph plotting the time in seconds spent either swimming or immobile during a 5-minute observation period for rats treated intraperitoneally with 5 mg/kg of the indicated compound, except that imipramine was administered at 15 mg/kg intraperitoneally. Each group of rats includes between five and eight animals. Compound-treated groups of rats exhibited a statistically different ($P \leq 0.01$) result as compared to the group of rats treated with saline.

Rats treated with PRC200-SS (5 mg/kg IP), MCJ002-NH2-SS (5 mg/kg IP), MCJ001-F—SS (5 mg/kg IP), MCJ001-F—SR (5 mg/kg IP), MCJ001-F—RS (5 mg/kg IP), MCJ001-N3-RS (5 mg/kg IP), MCJ001-OAc-SS (5 mg/kg IP), MCJ001-OMe-SS (5 mg/kg IP), MCJ001-Cl-SS (5 mg/kg IP), MCJ001-Cl-RS (5 mg/kg IP), and MCJ001-OH-Cyc-SS (5 mg/kg IP) exhibited antidepressant activity that was similar to that observed in rats treated with the positive control, imipramine (15 mg/kg IP) (FIG. 12A). Thus, rats treated with PRC200-SS, MCJ002-NH2-SS, MCJ001-F—SS, MCJ001-F—SR, MCJ001-F—RS, MCJ001-N3-RS, MCJ001-OAc-SS, MCJ001-OMe-SS, MCJ001-Cl-SS, MCJ001-Cl-RS, MCJ001-OH-Cyc-SS, or imipramine exhibited statistically (P<0.04) more swimming behavior and statistically (P<0.04) less immobility than rats treated with saline (FIG. 12A). In addition, MCJ001-F—RS exhibited statistically (P<0.04) less immobility than rats treated with imipramine (FIG. 12A).

Figure 12B:
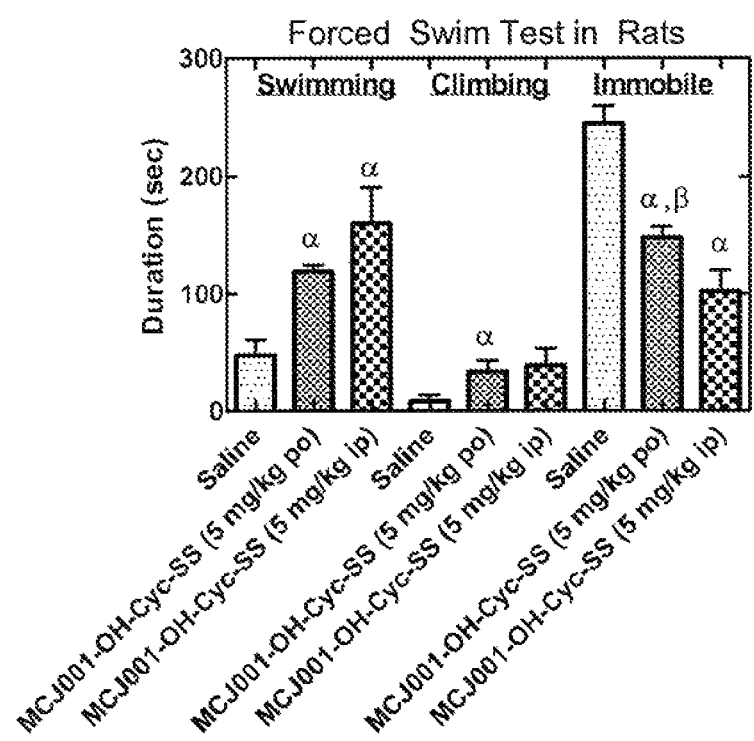
FIGS. 12B is a graph plotting the duration of swimming, climbing, and immobility (seconds) during a forced swim test of rats intraperitoneally (ip) or orally (po) treated with 5 mg/kg of the indicated compound. α indicates $P<0.04$ vs. saline; β indicates $P<0.04$ po vs. ip administration.
Figure 12C:
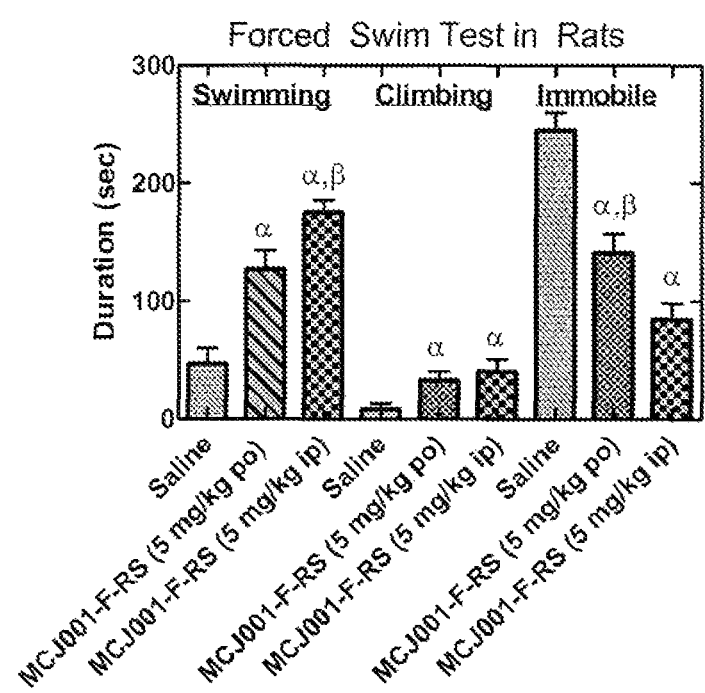
FIG. 12C is a graph plotting the duration of swimming, climbing, and immobility (seconds) during a forced swim test of rats intraperitoneally (ip) or orally (po) treated with 5 mg/kg of the indicated compound. α indicates $P<0.02$ vs. saline; β indicates $P<0.02$ po vs. ip administration.

In another study, rats treated with MCJ001-OH-Cyc-SS (5 mg/kg IP or 5 mg/kg PO) exhibited statistically (P≦0.04) more swimming and statistically (P≦0.04) less immobility than rats treated with saline (FIG. 12B). In addition, rats treated with MCJ001-OH-Cyc-SS (5 mg/kg PO) exhibited statistically (P≦0.04) more climbing than rats treated with saline (FIG. 12B). Also, rats treated with MCJ001-OH-Cyc-SS (5 mg/kg IP) exhibited statistically (P≦0.04) less immobility than rats treated with MCJ001-OH-Cyc-SS (5 mg/kg PO) (FIG. 12B). In yet another study, rats treated with MCJ001-F—RS (5 mg/kg IP or 5 mg/kg PO) exhibited statistically (P<0.02) more swimming and climbing; and statistically (P<0.02) less immobility than rats treated with saline (FIG. 12C). In addition, rats treated with MCJ001-F—RS (5 mg/kg IP) exhibited statistically (P<0.02) more swimming and less immobility than rats treated with MCJ001-F—RS (5 mg/kg IP) exhibited (FIG. 12C).

Example 5

Synthesis of (2R, 3R)-3-chloro-N-methyl-2-(naphthalen-2-yl)-3-phenylpropan-1-amine (MCJ001-Cl-RR)

The compound MCJ001-Cl-RR was made in four steps.
Step 1: Preparation of N-Boc-MCJ001-OH—RR: The compound MCJ001-F—RR/SS was made in three steps as follows: Step 1: An N-Boc derivative of (2R,3R)-3-hydroxy-N-methyl-2-(naphthalen-2-yl)-3-phenylpropan-1-amine hydrochloride was made by combing it (1.0 g, 3.05 mmol) with di-t-butyl dicarbonate (N-Boc)$_2$O) (832 mg, 3.81 mmol) in the presence of triethylamine (926 mg, 9.15 mmol) in DCM (30 mL) and allowing the reaction to proceed at room temperature for 6 hours, followed by standard extraction of the crude product with diethyl ether and silica gel purification. Yield 972 mg, 81%. $^1$H NMR (CDCl$_3$) δ 7.81-7.67 (m, 3H), 7.63 (bs, 1H), 7.47-7.38 (m, 3H), 7.23-7.09 (m, 5H), 5.03 (d, J=7.72 Hz, 1H), 4.5-4.35 (m, 1H), 3.84 (d, J=6.1 Hz, 2H), 3.55-3.41 (m, 1H), 1.56 (s, 3H), 1.48 (s, 9H); MS (ESI): m/z 414.23 (M +Na)$^+$.

Step 2: Preparation of N-Boc-MCJ001-OH—RS by Mitsunobu reaction. To a cooled (0° C.) solution of N-Boc-(2R, 3R)-3-hydroxy-N-methyl-2-(naphthale2-yl)-3-phenylpropan-1-amine (1.17 g, 2.99 mmol) in 25 mL of THF was added under nitrogen benzoic acid (547 mg, 4.48 mmol). To this stirred solution was added sequentially triphenylphosphine (1.18 g, 4.48 mmol) and diisopropyl azodicarboxylate (DIAD, 906 mg, 4.48 mmol). The mixture was slowly allowed to warm to room temperature and then left stirred for two days. The excess benzoic acid was destroyed by slow addition of aqueous NaHCO$_3$. The aqueous phase was extracted with EtOAc (3×), organic layers were combined, and the combined organic layer was washed with water and brine, then dried (MgSO$_4$). Filtering and evaporating the volatiles under reduced pressure left a crude that was purified by Flash chromatography (10% EtOAc/hexane) to furnish a mixture of the desired syn-N-Boc-protected benzoate ester (major) and the undesired anti-benzoate ester as a colorless gum. Yield of the mixture of syn- and anti-diastereomeric benzoate esters was 975 mg, 65.8%.

Separation of these diastereomers by Flash chromatography proved to be difficult at this stage, hence this mixture was directly taken to the saponification after which the corresponding alcohols were readily separated by Flash chromatography. The saponification was carried out by heating the diastereomeric benzoate mixture with KOH (1.14 g, 20.35 mmol) dissolved in 5 mL each of MeOH, EtOH, and water at 60° C. overnight. After standard work up with EtOAc the diastereomeric alcohols (N-Boc-MCJ001-OH—SR and N-Boc-MCJ001-OH—RR) could be readily separated by Flash chromatography. Yield: major N-Boc-MCJ001-OH—RS 427 mg, (55.7%), minor N-Boc-MCJ001-OH—SS 312 mg, (40.7%). $^1$H NMR of N-Boc-MCJ001-OH—RS (CDCl$_3$) δ 7.85-7.03 (m, 12H), 4.97 (d, J=5.65 Hz, 1H), 4.41-4.24 (m, 1H), 3.67-3.07 (m, 2H), 2.91 (s, 3H), 1.55 (s, 3H); MS: m/z (ESI) 414 (M+Na)$^+$.

Step 3: The N-Boc protecting group of N-Boc-(2R,3S)-3-hydroxy-N-methyl-2-(naphthalen-2-yl)-3-phenylpropan-1-amine was readily removed by reacting it for 1 hour at room temperature with excess 2M HCl in dioxane. The reaction mixture was evaporated under reduced pressure the gummy residue leached several times with dry diethyl ether, and dried. The HPLC profile, $^1$H NMR, and MS established purity of the product. $^1$H NMR (CDCl$_3$) δ 7.86-7.67 (m, 3H), 7.67-7.58 (m, 2H), 7.52-7.37 (m, 3H), 7.17-7.03 (m, 4H), 4.97 (d, J=4.77 Hz, 1H), 4.37-4.24 (t, 1H), 3.62-3.43 (m, 1H), 3.33-3.08 (m, 1H), 2.91(s, 3H), 2.61 (s, 1H), 1.46 (s, 9H); MS (ESI): m/z 414 (M+Na)$^+$.

Step 4: A mixture of (2R,3S)-3-hydroxy-N-methyl-2-(naphthalen-2-yl)-3-phenylpropan-1-amine.HCl (70 mg, 0.24 mmol) and 1 mL of thionyl chloride in 3 mL of dry dichloromethane (DCM) was stirred at room temperature for 30 minutes under nitrogen. The mass spectrum (MS) of the crude indicated clean and complete conversion. The volatiles were evaporated at reduced pressure. The product MCJ001-C1-RR was washed with dry diethyl ether, and dried under high vacuum. A white solid was obtained (74 mg, 90%) which was judged pure by $^1$H NMR and MS. $^1$H NMR (CD$_3$OD) δ 7.84-7.71 (m, 4H), 7.65 (s, 1H), 7.49-7.41 (m, 3H), 7.32-7.10 (m, 4H), 5.37 (d, J=9.4 Hz, 1H), 3.86-3.70 (m, 4H), 2.70 (s, 3H); MS (ESI): m/z 310.30 (M+1)$^+$; [α]$_D^{20}$ −11.0 (c 0.2, 9:1 EtOH:H2O).

Example 6

Figure 1:
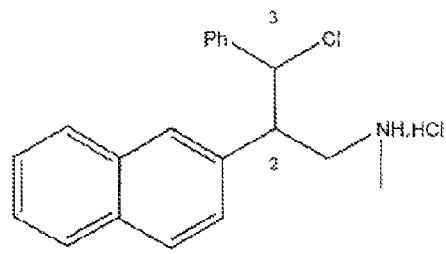
FIG. 1 is a diagram of 3-chloro-N-methyl-2-(naphthalen-2-yl)-3-phenylpropan-1-amine and its four stereoisomers.
Figure 1:
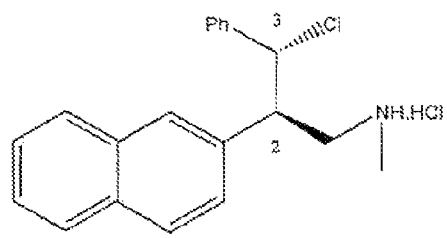
Figure 1:
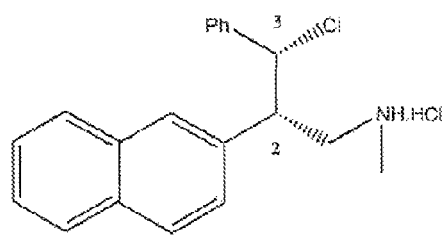
Figure 1:
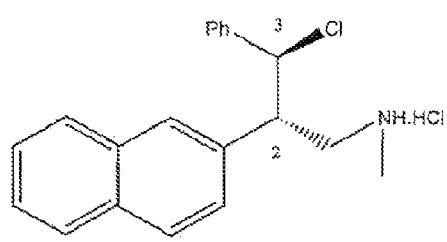
Figure 1:
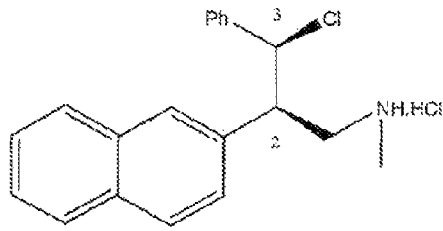

Synthesis of (2S,3S)-3-chloro-N-methyl-2-(naphthalen-2-yl)-3-phenylpropan-1-amine (MCJ001-C1-SS, FIG. 1)

The compound MCJ001-C1-SS was synthesized in four steps by following the same procedure as described in Example 5 except that the starting material in step 1 was PRC200 which has opposite stereochemical configuration to MCJ001-OH—RR. The 1H NMR and MS was identical to the corresponding (2R,3R) enantiomer. $^1$H NMR (CD$_3$OD) δ 7.85-7.69 (m, 4H), 7.66 (s, 1H), 7.49-7.41 (m, 3H), 7.33-7.04 (m, 4H), 5.38 (d, J=9.4 Hz, 1H), 4.07-3.-3.07 (m, 4H), 2.69 (s, 3H); MS (z/m) 310.30 (M+1)$^+$; [α]$_D^{20}$+9.5 (c 0.335, 9:1 EtOH:H2O).

Example 7

Figure 2:
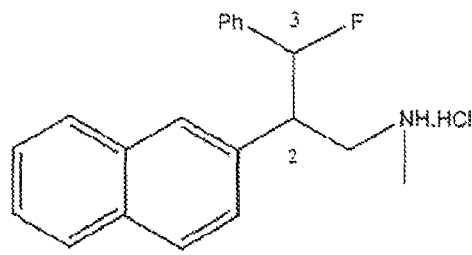
FIG. 2 is a diagram of 3-fluoro-N-methyl-2-(naphthalen-2-yl)-3-phenylpropan-1-amine and its four stereoisomers.
Figure 2:
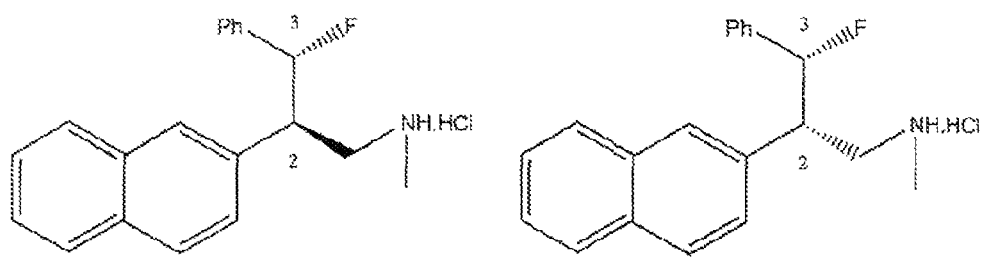
Figure 2:
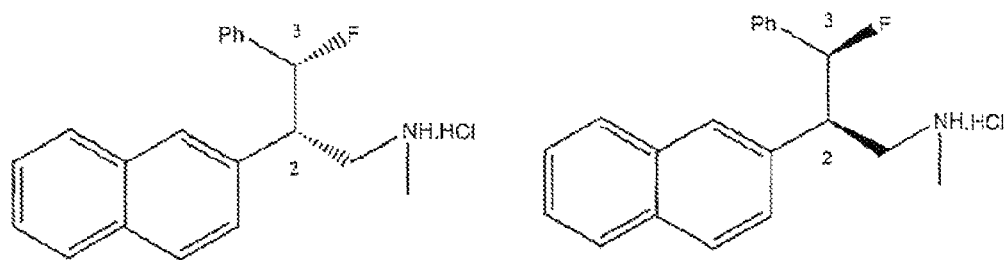

Synthesis of (2R,3R/2S,3S)-3-fluoro-N-methyl-2-(naphthalen-2-yl)-3-phenylpropan-1-amine (MCJ001-F—RR/SS, FIG. 2)

The compound MCJ001-F—RR/SS was made in three steps as follows. Step 1: A N-Boc derivative of (2S,3R/2R,3S)-3-hydroxy-N-methyl-2-(naphthalen-2-yl)-3-phenylpropan-1-amine hydrochloride was made essentially in quantitative yield by combing (2S, 3R/2R,3S)-3-hydroxy-N-methyl-2-(naphthalen-2-yl)-3-phenylpropan-1-amine hydrochloride (130 mg, 0.40 mmol) with di-t-butyl dicarbonate ((N-Boc)$_2$O) (108 mg, 0.50 mmol) in the presence of triethylamine (120 mg, 1.19 mmol) in DCM (3 mL) and allowing the reaction to proceed at room temperature 6 hours. Standard work up with diethyl ether and purification by Flash chromatography afforded pure N-Boc-MCJ001-OH—RS/SR. $^1$H NMR (CDCl$_3$) δ 7.87-7.01 (m, 12H), 4.98 (dd, J=3.8, 3.8 Hz, 1H), 4.45-4.23 (m, 1H), 3.59-3.42 (m, 1H), 3.34-3.09 (m, 2H), 2.92 (s, 3H), 1.53 (s, 3H), 1.47 (s, 6H); MS (ESI): m/z 414.36 (M+1), 392.26 (M+Na)$^+$.

Step 2: To a suspension of the N-Boc-(2S,3R/2R,3S)-3-hydroxy-N-methyl-2-(naphthalen-2-yl)-3-phenylpropan-1-amine (35.6 mg, 0.091 mmol), was added 2 mL of DCM and diethylaminosulfur trifluoride (0.02 mL, 0.182 mmol). The resulting mixture was stirred for 15 minutes. Saturated NaHCO$_3$ was cautiously added (exothermic reaction), and the reaction mixture was extracted 3× with EtOAc. The combined EtOAc extracts were washed sequentially with water and brine, and dried (MgSO$_4$). After filtering and concentration, the crude product was purified by Flash silica gel chromatography (eluting with 5-20% EtOAc/hex) to furnish the product N-Boc-MCJ001-F—SS/RR as a colorless oil in good yield. $^1$H NMR (CD$_3$OD) δ 7.84-7.67 (m, 3H), 7.57 (s, 1H), 7.49-7.39 (m, 3H), 7.26 (s, 3H), 7.24-7.14 (m, 2H), 7.14-7.05 (m, 1H), 5.76 (dd, J=46.3, 6.9 Hz, 1H), 3.95-3.68 (m, 1H), 2.75 (s, 1H), 2.63 (s, 1H), 2.55 (s, 3H), 1.55 (s, 9H); MS (ESI): m/z 416 (M+Na).

Step 3: The N-Boc protecting group of N-Boc-(2R,3R/2S, 3S)-3-fluoro-N-methyl-2-(naphthalen-2-yl)-3-phenylpropan-1-amine was readily removed by reacting it for 1 hour at room temperature with excess 2M HCl in dioxane. The reaction mixture was evaporated under reduced pressure, and the gummy crude after leaching several times with dry diethyl ether was dried under high vacuum. $^1$H NMR, and MS indicated that the desired product was pure. $^1$H NMR (CD$_3$OD) δ 7.87-7.72 (m, 4H), 7.67 (s, 1H), 7.52-7.43 (m, 3H), 7.32-7.13 (m, 4H), 5.81 (dd, J=46.5, 8.5 Hz, 1H), 3.91-3.65 (m, 4H), 2.72 (s, 3H); MS (ESI): m/z 294.26 (M+1)$^+$.

Example 8

Synthesis of (2R,3R)-3-fluoro-N-methyl-2-(naphthalen-2-yl)-3-phenylpropan-1-amine (MCJ001-F—RR, FIG. 2) and (2R,3R)-3-chloro-N-methyl-2-(naphthalen-2-yl)-3-phenylpropan-1-amine (MCJ001-C1-RR)

The MCJ001-F—RR (and MCJ001-C1-RR as a by-product) was made as follows.

To a suspension of the (2R,3S)-3-hydroxy-N-methyl-2-(naphthalen-2-yl)-3-phenylpropan-1-amine.HCl (169 mg, 0.89 mmol) in 20 mL of DCM, was added diethylaminosulfur trifluoride (0.31 mL, 2.36 mmol). The resulting mixture was stirred overnight at room temperature. Saturated NaHCO$_3$ (10 mL) was carefully added (exothermic reaction), and the reaction mixture was extracted 3x with EtOAc. The combined EtOAc extracts were washed sequentially with water and brine, and dried (MgSO$_4$). The major MCJ001-F—RR and the minor MCJ001-C1-RR were isolated by Flash chromatography eluting with 5% MeOH/DCM containing 0.1%) TEA. Rotary evaporation of the volatile fractions containing the products gave pure samples of the 3F— and 3-Cl products which were subsequently converted to their hydrochloride salts. Yield 110 mg (64.2%) for MCJ001-F—RR, and 24.6 mg (13.5%) for MCJ001-C1-RR. MCJ001-F—RR: $^1$H NMR (CD$_3$OD) δ 7.89-7.71 (m, 4H), 7.67 (s, 1H), 7.53-7.42 (m, 3H), 7.32-7.14 (m, 4H), 5.80 (dd, J=47.1, 8.9 Hz, 1H), 3.94-3.64 (m, 4H), 2.72 (s, 3H); MS (ESI): m/z 294.12 (M+1)$^+$. $[α]_D^{20}$–87.3 (c 0.3, 9:1 EtOH:H$_2$O). MCJ001-C1-RR $^1$H NMR (CD$_3$OD) δ 7.84-7.71 (m, 4H), 7.65 (s, 1H), 7.49-7.41 (m, 3H), 7.32-7.10 (m, 4H), 5.37 (d, J=9.4 Hz, 1H), 3.86-3.70 (m, 4H), 2.70 (s, 3H); MS: m/z 310.30 (M+1)$^+$; $[α]_D^{20}$–11.0 (c 0.2, 9:1 EtOH:H$_2$O).

Example 9

Synthesis of (2S,3R)-3-fluoro-N-methyl-2-(naphthalen-2-yl)-3-phenylpropan-1-amine (MCJ001-F—RS) and (2S, 3R)-3-chloro-N-methyl-2-(naphthalen-2-yl)-3-phenylpropan-1-amine (MCJ001-C1-RS)

To a suspension of the (2S,3S)-3-hydroxy-N-methyl-2-(naphthalen-2-yl)-3-phenylpropan-1-amine.HCl (PRC200) (500 mg, 1.72 mmol) in 20 mL of DCM, was added diethylaminosulfur trifluoride (1.12 mL, 8.58 mmol). The resulting mixture was stirred overnight at room temperature. Saturated NaHCO$_3$ (10 mL) was added very cautiously (exothermic reaction) and the reaction mixture was extracted 3× with EtOAc. The combined EtOAc extracts were washed sequentially with water and brine, and dried (MgSO$_4$). After filtering and concentrating the dried organic layer, the crude product was purified by Flash chromatography (using 5% MeOH/DCM containing 0.2% triethylamine as eluent) which gave the product (MCJ001-F—RS) as a colorless oil; yield 167 mg, 33.3%. A relatively small amount (72 mg, 7.8%) of the (2S,3R)-3-chloro-N-methyl-2-(naphthalen-2-yl)-3-phenylpropan-1-amine (MCJ001-C1-RS) was also isolated. MCJ001-F—RS: $^1$H NMR (CD$_3$OD) δ 7.89-7.74 (m, 4H), 7.68 (s, 1H), 7.54-7.42 (m, 3H), 7.34-7.09 (m, 4H), 5.83 (dd, J=48.2, 8.15 Hz, 1H), 3.93-3.66 (m, 4H), 2.74 (s, 3H); MS (ESI): m/z 294.26 (M+1)$^α$; $[α]_D^{20}$+97.2 (c 0.25, 9:1 EtOH:H$_2$O). MCJ001-C1-RS: $^1$H NMR (CD$_3$OD) δ 7.76-7.56 (m,4H), 7.39-7.29 (m, 3H), 7.24 (d, J=9.6 Hz, 1H), 7.19-7.11 (m, 2H), 7.07-6.92 (m, 2H), 5.81 (d, J=9.8 Hz, 1H), 3.98-3.78 (m, 2H), 3.76-3.61 (m, 2H), 2.60 (s, 3H); MS (ESI): m/z 310 (major peak, M+1)$^+$; $[α]_D^{20}$+14.4 (c, 0.235, 9:1 EtOH:H$_2$O).

Example 10

Synthesis of (2R,3S)-3-fluoro-N-methyl-2-(naphthalen-2-yl)-3-phenylpropan-1-amine (MCJ001-F—SR, FIG. 2) and (2S,3S)-3-chloro-N-methyl-2-(naphthalen-2-yl)-3-phenylpropan-1-amine (MCJ001-C1-SR)

The compound MCJ001-F—SR was synthesized as follows. To a suspension of the (2R,3R)-3-hydroxy-N-methyl-2-(naphthalen-2-yl)-3-phenylpropan-1-amine.HCl (200 mg, 0.686 mmol) in 20 mL of DCM, was added diethylaminosulfur trifluoride (0.36 mL, 2.75 mmol). The resulting mixture was stirred overnight at room temperature. Saturated NaHCO$_3$ (10 mL) was added very cautiously (exothermic reaction). the reaction mixture was extracted 3× with EtOAc. The EtOAc extracts were combined and washed sequentially with water and brine, and dried (MgSO$_4$). The crude product after filtering and concentration of the organic layer, was purified by Flash silica gel chromatography (eluting with 5% MeOH/DCM containing 0.1% triethylamine) which furnished the product as a colorless oil; yield 104 mg, 51.8%. A small amount (29.6 mg, 13.9%) of the (2S,3R)-3-chloro-N-methyl-2-(naphthalen-2-yl)-3-phenylpropan-1-amine (MCJ001-C1-SR) was also isolated. MCJ001-F—SR:_$^1$H NMR (CD$_3$OD) δ 7.91-7.72 (m, 4H), 7.66 (s, 1H), 7.54-7.42 (m, 3H), 7.35-7.07 (m, 4H), 5.83 (dd, J=47.09, 8.3 Hz, 1H), 3.93-3.64 (m, 4H), 2.72 (s, 3H); MS (ESI): m/z 294 (M+1)$^+$; $[α]_D^{20}$–92.0 (c 0.3, 9:1 EtOH:H$_2$O). MCJ001-C1-SR: $^1$H NMR (CD$_3$OD) δ 7.80-7.69 (m, 4H), 7.65 (s, 1H), 7.49-7.39 (m, 3H), 7.32-7.05 (m, 4H), 5.37 (d, J=9.4 Hz, 1H), 4.01 (d, J=11.3 Hz, 1H), 3.91-3.69 (m, 4H), 2.69 (s, 3H). MS: m/z 310 (M+1)$^+$; $[α]_D^{20}$–18.3 (c 0.35, 9:1 EtOH:H$_2$O).

Example 11

Synthesis of (2S,3S)-3-fluoro-N-methyl-2-(naphthalen-2-yl)-3-phenylpropan-1-amine (MCJ001-F—SS)

To a suspension of the (2S,3R)-3-hydroxy-N-methyl-2-(naphthalen-2-yl)-3-phenylpropan-1-amine.HCl (48.6 mg, 0.167 mmol) in 2 mL of DCM was added neat diethylaminosulfur trifluoride (0.073 mL, 0.67 mmol). The reaction mixture was stirred for 1 h at room temperature. Water (10 mL) was added very cautiously (exothermic reaction), and the aqueous reaction mixture was filtered through 0.45μ Teflon filters. The pure product was isolated by reverse phase HPLC (Vydac 2.2×25 cm, C-8, elution with a gradient of 10% B-100% B in 90 min, B=80% aq. CH$_3$CN with 0.1% TFA, A=H$_2$O with 0.1% TFA); FR=8 mL/min; $λ_{max}$=254 nm; RT=48.5 min). Evaporation of the solvent from product containing HPLC fractions furnished the product as a gummy residue that turned into a white solid after conversion to a hydrochloride salt and drying under high vacuum. Yield 8.9 mg, 18.2%. MCJ001-F-55: $^1$H NMR (CD$_3$OD) δ 7.87-7.72 (m, 4H), 7.67 (s, 1H), 7.52-7.43 (m, 3H), 7.32-7.13 (m, 4H), 5.81 (dd, J=46.5, 8.5 Hz, 1H), 3.91-3.65 (m, 4H), 2.72 (s, 3H); MS (ESI): m/z 294.12 (M+1)+; [α]$_D^{20}$ c 0.03, 9:1 EtOH:H$_2$O). MCJ001-C1-SS: $^1$H NMR (CD$_3$OD) δ 7.85-7.69 (m, 4H), 7.66 (s, 1H), 7.49-7.41 (m, 3H), 7.33-7.04 (m, 4H), 5.38 (d, J=9.4 Hz, 1H), 4.07-3.-3.07 (m, 4H), 2.69 (s, 3H); MS: m/z 310.30 (M+1)+; [α]$^{20}_D$ c,+9.5 (c 0.335, 9:1 EtOH:H$_2$O)

Example 12

Synthesis of (2S,3R)-3-azido-N-methyl-2-(naphthalen-2-yl)-3-phenylpropan-1-amine (MCJ001-N$_3$—RS FIG. 3)

The compound MCJ001-N$_3$—RS was made in three steps via a sequence involving a Mitsunobu reaction, or in four steps via an azide displacement of a methanesufonate (mesylate) intermediate. These independent sequences are described below.

Method A: Step 1: Preparation of N-Boc-(2S,3S)-3-hydroxy-N-methyl-2-(naphthalen-2-yl)-3-phenylpropan-1-amine (N-Boc-PRC200): The reagent di-t-butyldicarbonate (Boc)$_2$O, 499 mg, 2.29 mmol) was added portion wise at room temperature to a stirred mixture of (2S,3S)-3-hydroxy-N-methyl-2-(naphthalen-2-yl)-3-phenylpropan-1-amine-.HCl (600 mg, 1.83 mmol), and triethylamine (0.765 mL, 5.49 mmol) in 16 mL of DCM. Stirring was continued for 10-30 minutes while the progress of the reaction was monitored by thin layer chromatography (TLC). The reaction was quenched by adding a saturated aqueous NaHCO$_3$, and the aqueous phase was extracted with EtOAc (3×). The combined EtOAc extracts were sequentially washed with water and brine, and then dried (MgSO$_4$). Evaporation of the volatiles and purifying the residue by Flash chromatography (10% EtOAc/hexane) furnished the pure product as a colorless oil in essentially quantitative yield. $^1$H NMR (CDCl$_3$) δ 7.81-7.67 (m, 3H) 7.63 (bs, 1H), 7.47-7.38 (m, 3H), 7.23-7.09 (m, 5H), 5.03(d, J=7.72 Hz, 1H), 4.5-4.35 (m, 1H), 3.84 (d, J=6.1 Hz, 2H), 3.55-3.41 (m, 1H), 1.56 (s, 3H), 1.48 (s, 9H); MS (ESI): m/z 414.23 (M+Na)+.

Step2a-Mitsunobu reaction using hydrazoic acid: An approximately 2.5 M solution of hydrazoic acid (caution: extremely toxic and explosive when concentrated, use hood) in benzene was prepared by adding carefully 4.9 mL of con. H$_2$SO$_4$ at 0° C. to a stirred suspension of 6.5 g sodium azide (NaN$_3$) and 6.5 mL of water in 40 mL of benzene, stirring the resulting inhomogeneous mixture well for several minutes, then finally separating and drying (MgSO$_4$) the benzene layer.

To a cooled (0° C.) solution of N-Boc-(2S,3S)-3-hydroxy-N-methyl-2-(naphthale2-yl)-3-phenylpropan-1-amine (400 mg, 1.02 mmol) in 15 mL of THF was added under nitrogen 2.04 mL of freshly made hydrazoic acid solution (ca. 2.5 M in benzene). To this stirred solution was then added sequentially triphenylphosphine (402 mg, 1.53 mmol) and diisopropyl azodicarboxylate (DIAD, 310 mg, 1.53 mmol). The mixture was slowly allowed to warm to room temperature and then left stirred for two days. The excess hydrazoic acid was destroyed by slow addition of aqueous NaHCO$_3$. The aqueous phase was extracted with EtOAc (3×), organic layers were combined, and the combined organic layer was washed with water and brine, then dried (MgSO$_4$). Filtering and evaporating the volatiles under reduced pressure left a crude that was purified by Flash chromatography (10% EtOAc/hexane) to furnish the desired N-Boc-protected azide as colorless gum. Yield 365 mg, 86%. 1H NMR (CDCl3) δ 7.92-7.08 (m, 12H), 4.83 (d, J=6.2 Hz, 1H), 3.63-3.26 (m, 4H), 2.53 (s, 3H), 1.32 (s, 9H); MS (ESI): m/z, 439.17 (M+Na+); IR: 2100 cm-1.

Step 2b-Mitsunobu reaction using diphenylphosphoryl chloride: To N-Boc-PRC-200 (120 mg, 0.307 mmol) dissolved in 2 mL of THF cooled to 0° C. under nitrogen was added triphenylphosphine (80 mg, 0.307 mmol). This was followed by sequential drop wise addition of diisopropyl azodicarboxylate (DIAD, 0.06 mL, 0.307 mmol) and diphenylphosphoryl azide (DPPA, 0.065 mL, 0.307 mmol).

Stir and slowly bring to room temperature. The resulting mixture was slowly warmed to room temperature and stirred overnight. The progress of the reaction was monitored by TLC. After quenching the reaction with NaHCO$_3$, the aqueous phase was extracted with EtOAc (3×). The organic layers were combined, and the combined organic layer was washed with water and brine, then dried (MgSO$_4$). Filtering and evaporating the volatiles under reduced pressure left a crude that was purified by Flash chromatography (10% EtOAc/hexane) to furnish the desired N-Boc-protected azide as colorless gum. Yield 365 mg, 86%. The product was identical by spectral comparison to the one obtained by hydrazoic acid mediate Mitsunobu reaction described above.

Step 3. The N-Boc-(2S,3R)-3-azido-N-methyl-2-(naphthalen-2-yl)-3-phenylpropan-1-amine (148 mg, 0.355 mmol) was treated with a stirred 6.0 mL of 2.0 M solution of HCl in dry dioxane at room temperature for 1 hour. After removing the dioxane under rotary evaporation, the gummy solid was extensively leached with dry diethyl ether. The product (MCJ001-N$_3$—RS) was obtained as white powder after drying under high vacuum. $^1$H NMR (CD$_3$OD) δ 7.96-7.80 (m, 3H), 7.78 (s, 1H), 7.56-7.48 (m, 2H), 7.47-7.41 (m, 2H), 7.40-7.32(m, 2H), 7.31-7.22 (m, 2H), 5.08 (d, J=7.54 Hz, 1H), 3.68-3.45 (m, 2H), 3.16 (dd, J=11.7, 3.2 Hz, 1H), 2.69 (s, 1H), 2.57 (s, 3H); MS (ESI): m/z 339 (M+Na+); [α]$_{20}^D$+ 111.3 (c 0.3, 9:1 EtOH:H$_2$O).

Method B. Starting from N-Boc-PRC200-SS compound MCJ001-N$_3$—RS was also obtained in three steps via a mesylate through the following synthetic sequence.

Step 1: Compound N-Boc-(2S,3S)-3-hydroxy-N-methyl-2-(naphthalen-2-yl)-3-phenylpropan-1-amine (370 mg, 0.95 mmol) and triethylamine (0.40 mL, 2.84 mmol) were dissolved in 20 mL of dry diethyl ether and the solution was cooled to –10° C. under nitrogen. This was followed by a slow addition of methanesulfonyl chloride (either neat, or better, in a small amount of dry diethyl ether). The resulting mixture was stirred for 45 minutes or until the TLC showed completion of reaction, following which the reaction was quenched by adding water (10 mL). The aqueous phase was immediately extracted with diethyl ether (3×). The combined diethyl ether layers were washed once with water, then with brine. After drying over MgSO$_4$, the organic layer was filtered and concentrated under reduced pressure. A pale yellow liquid was obtained which was_characterized by MS and $^1$H NMR. This crude material N-Boc-MCJ001-OMs-SS was used in the next step without purification. MCJ001-N-Boc-OMs-SS: $^1$H NMR (CDCl$_3$) δ 7.77-7.14(m, 12H), 5.76(d, J=9.6 Hz, 1H), 3.97-3.61 (m, 2H), 2.55 (s, 3H), 1.53 (s, 3H), 1.29 (s, 9H); MS (ESI): m/z 470

Step 2: To the N-Boc-PRC200-mesylate (114 mg, 0.243 mmol) dissolved in 3 mL of DMF was added excess sodium azide (500 mg, 7.69 mmol), and the resulting suspension was stirred at room temperature under N$_2$. After the completion of reaction (12-24 hours), the mixture was diluted with water (50 mL), and the aqueous phase was extracted with diethyl ether (3×). The combined diethyl ether layers were washed once with water, then with brine. After drying over MgSO$_4$, the organic layer was filtered and concentrated under reduced pressure. A pale yellow liquid, thus obtained was purified by Flash chromatography (elution with 10% EtOAc/hexane), which gave the desired product as a colorless oil. N-Boc-MCJ001-N-Boc-N$_3$—RS: 1H NMR (CDCl$_3$) δ 7.88-7.18 (m, 12H), 4.83(d, J=6.6 Hz, 1H), 3.60-3.38 (m, 3H), 2.53 (s, 3H), 1.31 (s, 9H): IR: 2100 cm$^{-1}$; MS (ESI): m/z 439.22 (M+Na)$^+$.

Step 3: The N-Boc-MCJ001-N-Boc-N$_3$—RS was deblocked as described above. The spectral comparison between the compound MCJ001-N-Boc-N$_3$—RS obtained by the two routes showed identical product stereochemistry (syn).

Example 13

Synthesis of (2R,3S)-3-azido-N-methyl-2-(naphthalen-2-yl)-3-phenylpropan-1-amine (MCJ001-N$_3$—SR)

The compound MCJ001-N$_3$—SR was made in three steps via a sequence involving a Mitsunobu reaction, or in four steps via an azide displacement of a methanesufonate (mesylate) intermediate. These independents sequences are described below.

Method A: Step 1: N-N-Boc-(2R,3S)-3-azido-N-methyl-2-(naphthalen-2-yl)-3-phenylpropan-1-amine was made as follows. The di-t-butyldicarbonate (N-Boc)$_2$O, 832 mg, 3.81 mmol) was added portion-wise at room temperature to a stirred mixture of (2R,3R)-3-hydroxy-N-methyl-2-(naphthalen-2-yl)-3-phenylpropan-1-amine.HCl (1.00 g, 3.05 mmol), and triethylamine (1.28 mL, 9.15 mmol) in 30 mL of DCM. Stirring was continued for 10-30 minutes while the progress of the reaction was monitored by thin layer chromatography (TLC). The reaction was quenched by adding saturated aqueous NaHCO$_3$, and the aqueous phase was extracted with EtOAc (3×). The combined EtOAc extracts were sequentially washed with water and brine, and then dried (MgSO$_4$). Evaporation of the volatiles and purifying the residue by Flash chromatography (10% EtOAc/hexane) furnished the pure product as a colorless oil in essentially quantitative yield. N-Boc-MCJ001-OH—RR: $^1$H NMR (CDCl$_3$+D$_2$O) δ 7.86-7.07(m, 12H), 5.02 (d, J=6.41 Hz, 1H), 3.96-3.67 (m, 2H), 3.47 (bs, 1H), 2.43 (s, 3H), 1.41 (s, 9H); MS: m/z (ESI) 414 (M$_{+Na}$)+.

Step 2: Mitsunobu reaction using hydrazoic acid: An approximately 2.5 M solution of hydrazoic acid (caution: extremely toxic and explosive when concentrated, use hood) in benzene was prepared as described in Example 12. To a cooled (0° C.) solution of N-Boc-(2R,3R)-3-hydroxy-N-methyl-2-(naphthale2-yl)-3-phenylpropan-1-amine (190 mg, 0.485 mmol) in 10 mL of THF was added under nitrogen 0.97 mL of freshly made hydrazoic acid solution (ca. 2.5 M in benzene). To this stirred solution was then added sequentially triphenylphosphine (191 mg, 0.728 mmol) and diisopropyl azodicarboxylate (DIAD, 147 mg, 0.728 mmol). The mixture was slowly allowed to warm to room temperature and then left stirred for two days. The excess hydrazoic acid was destroyed by slow addition of aqueous NaHCO$_3$. The aqueous phase was extracted with EtOAc (3×), organic layers were combined, and the combined organic layer was washed with water and brine, then dried (MgSO$_4$). Filtering and evaporating the volatiles under reduced pressure left a crude residue from which the product was isolated by Flash chromatography (10% EtOAc/hexane). The desired N-Boc-protected azide was obtained as colorless gum. $^1$H NMR (CDCl$_3$) δ 7.92-7.08 (m, 12H), 4.83 (d, J=6.2 Hz, 1H), 3.63-3.26 (m, 4H), 2.53 (s, 3H), 1.32 (s, 9H); MS (ESI): m/z, 439.17 (M+Na$^+$); IR: 2100 cm$^{-1}$.

Step 3: The N-Boc-(2R,3S)-3-azido-N-methyl-2-(naphthalen-2-yl)-3-phenylpropan-1-amine (148 mg, 0.355 mmol) was treated with a stirred 6.0 mL of 2.0 M solution of HCl in dry dioxane at room temperature for 1 hour. After removing the dioxane under rotary evaporation, the gummy solid was extensively leached with dry diethyl ether. The product (MCJ001-N$_3$—SR) was obtained as white powder after drying under high vacuum. $^1$H NMR (CD$_3$OD) δ 7.96-7.80 (m, 3H), 7.78 (s, 1H), 7.56-7.48 (m, 2H), 7.47-7.41 (m, 2H), 7.40-7.32(m, 2H), 7.31-7.22 (m, 2H), 5.08 (d, J=7.54 Hz, 1H), 3.68-3.45 (m, 2H), 3.16 (dd, J=11.7, 3.2 Hz, 1H), 2.69 (s, 1H), 2.57 (s, 3H). MS (ESI): m/z 339 (M+Na$^+$): [α]$_D^{20}$+111.3 (c 0.3, 9:1 EtOH:H$_2$O).

Method B. Starting from N-Boc-MCJ001-OH—RR, the compound MCJ001-N$_3$—SR was also obtained in three steps via a mesylate through the following synthetic sequence.

Step 1: Compound N-Boc-(2R,3R)-3-hydroxy-N-methyl-2-(naphthalen-2-yl)-3-phenylpropan-1-amine (N-Boc-MCJ001-OH—RR, 370 mg, 0.95 mmol) and triethylamine (0.40 mL, 2.84 mmol) were dissolved in 20 mL of dry diethyl ether, and the solution was cooled to −10° C. under nitrogen. This was followed by a slow addition of methanesulfonyl chloride (either neat, or better, in a small amount of dry diethyl ether). The resulting mixture was stirred for 45 minutes or until the TLC showed completion of reaction, following which the reaction was quenched by adding water (10 mL). The aqueous phase was immediately extracted with diethyl ether (3×). The combined diethyl ether layers were washed once with water, then with brine. After drying the organic layer over MgSO$_4$, the organic layer was filtered and concentrated under reduced pressure. A pale yellow liquid (N-Boc-MCJ001-OMs-RR) was obtained that was characterized by MS and $^1$H NMR and used in the next step without purification. PRC201-N-Boc-OMs-RR: $^1$H NMR (CDCl$_3$) δ 7.77-7.14(m, 12H), 5.76(d, J=9.6 Hz, 1H), 3.97-3.61 (m, 2H), 2.55 (s, 3H), 1.53 (s, 3H), 1.29 (s, 9H); MS (ESI): m/z 470 (M+1)$^+$.

Step 2: To the N-Boc-MCJ001-OMs-RR (200 mg, 0.426 mmol) dissolved in 3 mL of DMF was added excess sodium azide (138 mg, 2.13 mmol), and the resulting suspension was stirred at room temperature under N$_2$. After the completion of reaction (12-24 hours), the mixture was diluted with water (50 mL), and the aqueous phase was extracted with diethyl ether (3×). The combined diethyl ether layers were washed once with water, then with brine. After drying over MgSO$_4$, the organic layer was filtered and concentrated under reduced pressure. A pale yellow liquid, thus obtained was purified by Flash chromatography (elution with 10% EtOAc/hexane) which gave the desired product as a colorless oil. Yield 115 mg, 64.8%. N-Boc-MCJ001-N$_3$—SR: $^1$H NMR (CD$_3$OD) δ 7.92-7.08 (m, 12H), 4.83 (d, J=6.2 Hz, 1H), 3.63-3.26 (m, 4H), 2.53 (s, 3H), 1.32 (s, 9H); IR: 2100 cm$^{-1}$; MS: m/z (ESI) 439 (M+Na)$^+$.

Step 3: The N-Boc-MCJ001-N$_3$—SR was deblocked as described above in the Mitsunobu sequence. The spectral comparison between the samples of MCJ001-N$_3$—SR obtained by the two routes showed identical product stereochemistry (syn).

Example 14

Figure 4:
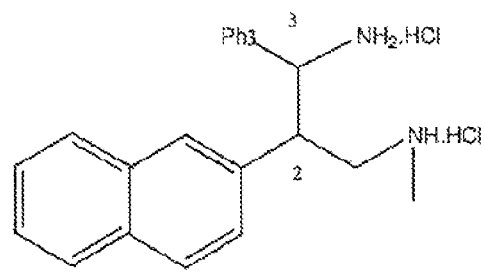
FIG. 4 is a diagram of N1-methyl-2-(naphthalen-2-yl)-3-phenylpropane-1,3-diamine and its four stereoisomers.
Figure 4:
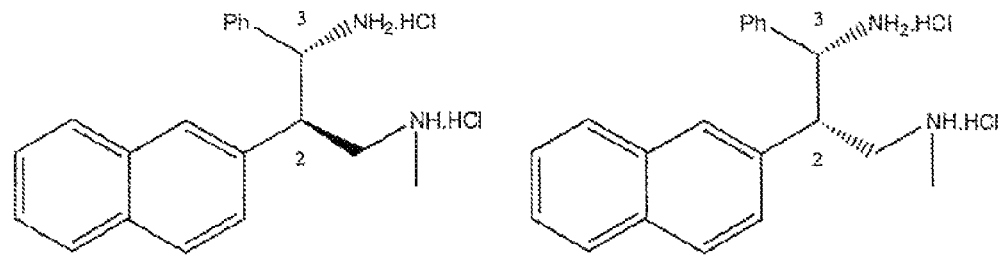
Figure 4:
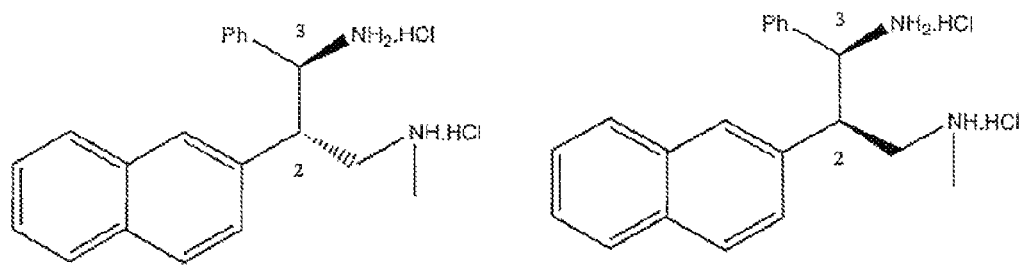

Synthesis of (2R,3R/2S,3S)—N-1-methyl-2-(naphthalen-2-yl)-3-phenylpropane-1,3-diamine (MCJ001-NH$_2$—RR/SS, FIG. 4)

The compound MCJ001-NH$_2$—RR/SS was made in three steps as follows.

Step 1: Preparation of ethyl carbamate derivative of MCJ000-OH—RS/SR. To a solution of MCJ000-OH—RS/

SR (isolated by Flash chromatography of mother liquors left over from the crystallization of anti-product of the aldol reaction) (640 mg, 2.307 mmol) in dry DCM (15 mL) at 0° C. was added ethyl chloroformate (275 mg, 2.54 mmol) drop wise. Pyridine (2.8 mL was added, and after stirring for at 0° C. for one hour, the ice bath was removed, and the mixture was stirred overnight. The reaction mixture was diluted with DCM and poured into a separatory funnel containing 2N-HCl (5 mL). The aqueous phase was magnetically stirred for 30 minutes to decompose small amounts of carbonate byproduct before extracting it with DCM (×3). The combined diethyl ether extracts were washed with water, and then dried over $MgSO_4$. Filtration and evaporation of the filtrate left a flaky solid which was judged almost pure by $^1H$ NMR. Yield 741 mg, 92%.

Step 2: To a cooled (0° C.) solution of ethyl carbamate derivative of MCJ000-OH—RS/SR (1.0 g, 2.86 mmol) in 15 mL of THF was added a 2.5 M benzene solution of Hydrazoic acid (2.29 mL, 5.72 mmol) under nitrogen. This was followed by sequential addition of triphenylphosphine (1.13 g, 4.29 mmol) and diisopropyl azodicarboxylate (DIAD) (2.29 mL, 4.29 mmol). The resulting mixture was slowly allowed to warm to room temperature and then stirred at room temperature until the TLC showed completion of reaction. The reaction was quenched with aqueous $NaHCO_3$, and the aqueous phase was extracted with EtOAc (3×). The extracts were combined and washed with water and brine, and finally dried ($MgSO_4$). After filtration, the organic layer was concentrated using a rotary evaporator to give a crude that was Flash-chromatographed with 15% EtOAc/hexane as eluent to furnish the desired product (N-Ethyl-MCJ000-$N_3$—RR/SS) as a thick oil. $^1H$ NMR ($CDCl_3$) δ 7.80-7.65 (m, 3H), 7.48-7.39 (m, 3H), 7.23-7.09 (m, 6H), 4.79 (d, J=9.2 Hz, 1H), 4.57 (bs, 1H), 4.09-3.93 (m, 3H), 3.62-3.49 (m, 1H), 1.62 (s, 1H), 1.21-1.08 (m, 3); IR: 2100 $cm^{-1}$.

Step 3: To a stirred solution of N-Ethyl-MCJ000-$N_3$—RR/SS (100 mg, 0.267 mmol) in THF (15 mL) was slowly lithium aluminum hydride (80 mg, 2.1 mmol,). The resulting mixture was refluxed overnight under nitrogen. 2N—NaOH solution was added, and the aqueous phase was extracted with EtOAc (3×). The organic layers were combined, washed with water and brine, then dried ($MgSO_4$). The product was purified by reverse phase HPLC (10% B-100% B in 30 minutes; B=80% aq. $CH_3CN$ with 0.1% TFA, A=$H_2O$ with 0.1% TFA), FR=8 mL/min; $λ_{max}$=254 nm, RT=19.8 minutes) to furnish the diamine which was immediately converted to a dihydrochloride salt. Yield 68 mg, 89%.

Example 15

Synthesis of (2S,3R)—N-1-methyl-2-(naphthalen-2-yl)-3-phenylpropane-1,3-diamine (MCJ001-$NH_2$—RS, FIG. 4)

The compound MCJ001-$NH_2$—RS was synthesized as follows.

Step 1: Preparation of butoxycarbonyl (N-Boc) derivative of PRC200. This is described in Example 12.

Step 2: Preparation of N-Boc-MCJ001-$N_3$—RS: To a cooled (0° C.) solution of butoxycarbonyl derivative of N-Boc-PRC200 (300 mg, 0.766 mmol) in 15 mL of THF was added a 2.5 M benzene solution of hydrazoic acid (1.53 mL, 3.83 mmol) under nitrogen. This was followed by sequential addition of triphenylphosphine (301 mg, 1.15 mmol) and diisopropyl azodicarboxylate (DIAD) (0.226 mL, 1.15 mmol). The resulting mixture was slowly allowed to warm to room temperature and then stirred at room temperature until the TLC showed completion of reaction. The reaction was quenched with aqueous $NaHCO_3$, and the aqueous phase was extracted with EtOAc (3×). The extracts were combined and washed with water and brine, and finally dried ($MgSO_4$). After filtration, the organic layer was concentrated using a rotary evaporator to give a crude that was Flash-chromatographed with 15% EtOAc/hexane as eluent to furnish the desired product as a thick oil. $^1H$ NMR ($CDCl_3$) δ 7.92-7.08 (m, 12H), 4.83 (d, J=6.2 Hz, 1H), 3.63-3.26 (m, 4H), 2.53 (s, 3H), 1.32 (s, 9H); MS (ESI): m/z, 439.17 (M+$Na^+$); IR: 2100 $cm^{-1}$. Yield 148 mg, 46.4%.

Step 3: Reduction of azide N-Boc-MCJ001-$N_3$—RS to amine N-Boc-MCJ001-$NH_2$—RS: To a solution of N-Boc-MCJ001-$N_3$—RS (120 mg, 0.288 mmol) in EtOH (10 mL) cooled to −78° C. was added carefully 10% Pd—C (20 mg). The reaction vessel was evacuated and then filled with hydrogen using balloon. After stirring under hydrogen overnight, filtration through Celite and concentration afforded the product in almost pure form. $^1H$ NMR ($CDCl_3$) δ7.87-7.01 (m, 12H), 4.31-4.17 (m, 1H), 3.93-3.79 (m, 1H), 3.47 (s, 1H), 2.53-2.286 (s, 3H), 1.73-1.26 (s, 2H), 1.21 (s, 9H); MS (ESI): m/z 391.32 (M+1)$^+$.

Step 4: Removal of the N-Boc protecting group was achieved by treating the N-Boc-MCJ001-$NH_2$—RS obtained from 120 mg (0.288 mmol) of the N-Boc-MCJ001-$N_3$—RS with 6.0 mL of 2.0 M solution of HCl in dry dioxane at room temperature for 1 hour. After removing the dioxane under rotary evaporation, the gummy solid was extensively leached with dry diethyl ether, converted to a dihydrochloride, and rigorously dried under high vacuum. The product (MCJ001-$NH_2$—RS) was obtained as a white powder. Yield 37.3 mg (35.4% from the N-Boc MCJ001-$N_3$—RS). $^1H$ NMR ($CD_3OD$) δ 8.25 (s,1H), 8.13 (s, 1H), 8.04-7.93 (m, 3H) 7.85-7.72 (m, 3H), 7.65-7.49 (m, 4H), 4.76 (d, J=7.8 Hz, 1H), 4.13-4.00 (m, 1H), 3.76 (dd, 12.6, 3.6 Hz, 1H), 2.66 (s, 3H), 2.52 (s, 3H); MS (ESI): m/z, 291.28 (M+1)$^+$.

Example 16

Synthesis of (2R,3S)—N-1-methyl-2-(naphthalen-2-yl)-3-phenylpropane-1,3-diamine (MCJ001-$NH_2$—SR)

Step 1: Preparation of N-butoxycarbonyl N-Boc-MCJ001-OH—RR. This is described in Example 5.

Step 2: Preparation of mesylate derivative of MCJ001-OH—RR. Compound N-Boc-(2R,3R)-3-hydroxy-N-methyl-2-(naphthalen-2-yl)-3-phenylpropan-1-amine (370 mg, 0.95 mmol) and triethylamine (0.40 mL, 2.84 mmol) were dissolved in 20 mL of dry diethyl ether, and the solution was cooled to −10° C. under nitrogen. This was followed by a slow addition of methanesulfonyl chloride (either neat, or better, in a small amount of dry diethyl ether). The resulting mixture was stirred for 45 minutes or until the TLC showed completion of reaction, following which the reaction was quenched by adding water (10 mL). The aqueous phase was immediately extracted with diethyl ether (3×). The combined diethyl ether layers were washed once with water, then with brine. After drying over $MgSO_4$, the organic layer was filtered and concentrated under reduced pressure. A pale yellow liquid was obtained which was characterized by MS and $^1H$ NMR.

Step 3: To the N-Boc-MCJ-OMs-RR (200 mg, 0.426 mmol) dissolved in 3 mL of DMF was added excess sodium azide (138 mg, 2.13 mmol), and the resulting suspension was stirred at room temperature under $N_2$. After the completion of reaction (12-24 hours), the mixture was diluted with water (10 mL), and the aqueous phase was extracted with diethyl ether (3×). The combined diethyl ether layers were washed once with water, then with brine. After drying over MgSO$_4$, the organic layer was filtered and concentrated under reduced pressure. A pale yellow liquid, thus obtained, was purified by Flash chromatography (elution with 10% EtOAc/hexane) which gave the desired product as a colorless oil. $^1$H NMR (CDCl$_3$) δ 7.88-7.18 (m, 12H), 4.83 (d, J=6.6 Hz, 1H), 3.60-3.38 (m, 3H), 2.53 (s, 3H), 1.31 (s, 9H): IR: 2100 cm$^{-1}$; MS (ESI): m/z 439.22 (M+Na)$^+$. MCJ001-N-Boc-N$_3$—SR: $^1$H NMR (CDCl$_3$) δ 7.92-7.08 (m, 12H), 4.83 (d, J=6.2 Hz, 1H), 3.63-3.26 (m, 4H), 2.53 (s, 3H), 1.32 (s, 9H); IR: 2100 cm$^{-1}$; MS (ESI): m/z 439.17 (M+Na)$^+$.

Step 4: Reduction of azide N-Boc-MCJ001-N$_3$—SR to amine (N-Boc-MCJ001-NH$_2$—SR): To a solution of N-Boc-MCJ001-N$_3$—SR (115 mg, 0.276 mmol) in EtOH (10 mL) cooled to −78° C. was added carefully 10% Pd—C (50 mg). The reaction vessel was evacuated and then filled with hydrogen using balloon. After stirring under hydrogen overnight, filtration through Celite and concentration afforded the product in almost pure form. $^1$H NMR (CDCl$_3$) δ7.87-7.01 (m, 12H), 4.31-4.17 (m, 1H), 3.93-3.79 (m, 1H), 3.47 (s, 1H), 2.53-2.286 (s, 3H), 1.73-1.26 (s, 2H), 1.21 (s, 9H); MS (ESI): m/z 391.32 (M+1)$^+$.

Step 5: Removal of the N-Boc protecting group was achieved by treating N-Boc-MCJ001-NH$_2$—SR (60 mg, 0.144 mmol) with 3.0 mL of 2.0 M solution of HCl in dry dioxane at room temperature for 1 hour. After removing the dioxane under rotary evaporation, the gummy solid was extensively leached with dry diethyl ether. The product (MCJ001-NH$_2$—SR) was obtained as a white powder. Yield 18 mg, 32%. $^1$H NMR (D$_2$O) δ 8.22-7.54 (m, 12H), 3.90-3.79 (m, 1H), 3.76 (m, 1H), 3.57 (t, 1H), 2.91(dd, J=12.4, 4.1 Hz, 1H), 2.49(s, 3H); MS (ESI): m/z 291.21 (M+1)$^+$.

Example 17

Synthesis of (1S,2S)-3-(methylamino)-2-(naphthalen-2-yl)-1-phenylpropyl acetate (MCJ001-OAc-SS)

Step 1: To a solution of N-Boc-PRC-200 (96 mg, 0.245 mmol) in add 5 mL of pyridine was added acetic anhydride (0.464 mL, 4.92 mmol). The resulting mixture was left stirred overnight at room temperature. After evaporating the pyridine with a rotary evaporator, the reaction mixture was neutralized by addition of 1M-HCl, and the aqueous phase was extracted with diethyl ether (3×). The organic layers were combined in a separation funnel, washed first with water, and then with brine, and finally dried with MgSO$_4$. Filtration and evaporation under reduced pressure afforded an oily residue from which judged pure by $^1$H NMR and MS. Yield 98.4 mg, 93%. $^1$H NMR (CDCl$_3$) δ 8.06-6.69 (m, 2H), 6.08 (s, 1H), 3.96-3.52 (m, 3H), 2.54 (s, 3H), 2.13(s, 3H), 1.33 (s, 9H); MS: m/z (ESI) 456.29 (M+Na)$^+$.

Step 2: Removal of N-Boc from N-Boc-MCJ001-OAc-SS: Removal of the N-Boc protecting group was achieved by treating N-Boc-MCJ001-OAc-SS (98.6 mg, 0.227 mmol) with 4.0 mL of 2.0 M solution of HCl in dry dioxane at room temperature for 1 hour. After removing the dioxane under rotary evaporation, the gummy solid was extensively leached with dry diethyl ether. The product (MCJ001-OAc-SS) was purified by reverse phase HPLC (Vydac column, 2.2×25 cm, C-18, 10% B-100% B in 90 minutes, FR 8 mL/minute; RT=46.865 minutes). The relevant HPLC fractions were combined and evaporated under reduced product. Finally, the product was converted to a hydrochloride and lyophilized to furnish the desired product as a white powder. Yield 42.6 mg, 56.2%. $^1$H NMR (CD$_3$OD) δ 7.85-7.73 (m, 4H), 7.68 (s, 1H), 7.49-7.42 (m, 2H), 7.33 (dd, J=8.5, 1.7 Hz, 1H), 7.14 (s, 4H), 5.97 (d, J=8.5 Hz, 1H), 2.67 (s, 3H), 2.14(s, 3H); MS: m/z (ESI) 334 (M+1)$^+$; $[\alpha]_D^{20}$+17.8 (c 0.28, 9:1 EtOH:H$_2$O).

Example 18

Synthesis of (2R,3S/2S,3R)-3-methoxy-N-methyl-2-(naphthalen-2-yl)-3-phenylpropan-1-amine (MCJ001-OMe-RS/SR)

This compound was prepared in three steps.

Step 1: A solution of di-t-butyldicarbonate (N-Boc)$_2$O, 108 mg, 0.496 mmol) in DCM was added portion wise at room temperature to a stirred mixture of (2R,3S/2S,3R)-3-hydroxy-N-methyl-2-(naphthalen-2-yl)-3-phenylpropan-1-amine.HCl (130 mg, 0.397 mmol)), and triethylamine (0.12 mL, 0.166 mmol) in 30 mL of DCM. Stirring was continued for 10-30 minutes while the progress of the reaction was monitored by thin layer chromatography (TLC). The reaction was quenched by adding saturated aqueous NaHCO$_3$, and the aqueous phase was extracted with EtOAc (3×). The combined EtOAc extracts were sequentially washed with water and brine, and then dried (MgSO$_4$). Evaporation of the volatiles and purifying the residue by Flash chromatography (10% EtOAc/hexane) furnished the pure product as a colorless oil in essentially quantitative yield. $^1$H NMR (CDCl$_3$) δ 7.75-7.68 (m, 2H), 7.62 (s, 1H), 7.49-7.39 (m, 2H), 7.30-7.24 (m, 2H), 7.14-7.10 (s, 5H), 4.97 (t, J=4.1 Hz, 1H), 3.31-3.10 (m, 3H), 2.91 (s, 3H), 1.47 (s, 9H); MS: m/z (ESI) 414.28 (M+Na)$^+$.

Step 2: N-Boc-MCJ001-OH—RS/SR (293 mg, 0.748 mmol) was dissolved in 5 mL of DMF. After cooling the solution to 0° C., sodium hydride (50% oil suspension, 22 mg, 0.897 mmol) was added under nitrogen. The resulting suspension was stirred for 5 minutes at 0° C. for completion of alkoxide formation. Then, a solution of iodomethane (0.07 mL, 1.12 mmol) in DMF was cannulated into it, and the reaction mixture was left stirred 2 hours. Work up consisted of adding water to the reaction mixture, extracting with EtOAc (×3), combining the organic layers, and washing them sequentially with water and brine, and then drying with MgSO$_4$. Filtration and evaporation under reduced pressure left a residue that was purified by silica gel chromatography (20% EtOAc/hexane). The product (N-Boc-MCJ001-OMe-SS) was obtained as a colorless oil. Yield 237 mg (78%). $^1$H NMR (CDCl$_3$) δ 7.82-7.71 (m, 3H), 7.54 (br s, 7.42-7.29 (m, 3H), 7.27-7.10 (m, 5H), 4.45 (d, J=6.0 Hz, 1H), 3.80-3.22 (m, 3H), 3.15 (s, 3H), 2.59 (s, 3H), 1.37 (s, 9H); MS: m/z 428.38 (M+Na)$^+$.

Step 3: Removal of the N-Boc protecting group of N-Boc-MCJ001-OMe-RS/SR was achieved by treating N-Boc-MCJ001-OMe-RS/SR (237 mg, 0.585 mmol) with 4.0 mL of 1:1 mixture of dry DCM and TFA at room temperature for 1 hour. After removing the volatiles under rotary evaporation, the gummy solid was extensively leached with dry diethyl ether. After drying under high vacuum, the product (MCJ001-OMe-RS/SR) was obtained as a white powder in essentially quantitative yield. $^1$H NMR (CD$_3$OD) δ (CDCl$_3$) 7.81-7.60 (m, 4H), 7.46-7.39 (m, 2H), 7.29-7.19 (m, 3H), 7.01 (dd, J=7.4, 1.5 Hz, 1H), 6.88 (d, J=7.8 Hz, 2H), 4.75 (d, J=3.4 Hz, 3.62 (m, 1H), 3.48-3.29 (m, 2H), 3.22 (s, 3H), 2.03 (s, 3H); MS: m/z (ESI) 306.30 (M+1)$^+$.

Example 19

Synthesis of (2S,3S)-3-methoxy-N-methyl-2-(naphthalen-2-yl)-3-phenylpropan-1-amine (MCJ001-OMe-SS)

Step 1: N-Boc-PRC200 (200 mg, 0.511 mmol) was dissolved in 5 mL of DMF. After cooling the solution to 0° C., sodium hydride (50% oil suspension, 37 mg, 1.53 mmol) was added under nitrogen. The resulting suspension was stirred for 5 minutes at 0° C. for completion of alkoxide formation. Then, a solution of iodomethane (0.064 mL, 1.02 mmol) in DMF was cannulated into it, and the reaction mixture was left stirred 2 hours. Work up consisted of adding water to the reaction mixture, extracting with EtOAc (×3), combining the organic layers, and washing them sequentially with water and brine, and then drying with MgSO$_4$. Filtration and evaporation under reduced pressure left a residue that was purified by silica gel chromatography (10-15% EtOAc/hexane). The product (N-Boc-MCJ001-OMe-SS) was obtained as a colorless oil. Yield 157 mg (76%); $^1$H NMR (CDCl$_3$) δ 7.86-6.93 (m, 12H), 5.83 (d, J=8.10 Hz, 1H), 4.40 (d, J=6.0 Hz, 1H), 3.63-3.41 (m, 3H), 3.25 (s, 3H), 2.55 (s, 3H), 1.35-1.03 (m, 9H). MS: m/z 406.23 (M+1)$^+$.

Step 2: Removal of the N-Boc protecting group of N-Boc-MCJ001-OMe-SS was achieved by treating N-Boc-MCJ001-OMe-SS (157 mg, 0.144 mmol) with 3.0 mL of 2.0 M solution of HCl in dry dioxane at room temperature for 1 hour. After removing the dioxane under rotary evaporation, the gummy solid was extensively leached with dry diethyl ether. After drying under high vacuum, the product (MCJ001-OMe-SS) was obtained as a white powder. Yield 115 mg, 97%. $^1$H NMR (CD$_3$OD) δ 7.83-7.66 (m, 4H), 7.53(s, 1H), 7.47-7.39 (m, 3H), 7.26 (m, 5H), 4.60 (d, J=9.5 Hz, 1H), 3.95-3.82 (m, 1H), 3.50-3.38 (m, 2H), 3.26 (s, 3H), 2.74 (s, 3H); MS: m/z (ESI) 306 (M+1)$^+$; [α]$_D^{20}$+105.1 (c 0.35, 9:1 EtOH:H$_2$O).

Example 20

Synthesis of (4S,5S)-1-methyl-5-(naphthalen-2-yl)-4-phenylhexahydropyrimidine (MCJ001-CycNH$_2$—SS)

This compound was obtained as a second product in the lithium aluminum hydride reduction of N-Boc-MCJ001-N$_3$—SS, and is described and characterized in Example 21.

Example 21

Synthesis of (2S,3S)-N1,N1-dimethyl-2-(naphthalen-2-yl)-3-phenylpropane-1,3-diamine (MCJ002-NH$_2$—SS) and MCJ001-CycNH2-SS The compound MCJ002-NH$_2$—SS was obtained from MCJ001-OH—RS in three steps.

Step 1: Preparation of N-Boc-MCJ001-OH—RS by Mitsunobu reaction. To a cooled (0° C.) solution of N-Boc-(2S, 3S)-3-hydroxy-N-methyl-2-(naphthale2-yl)-3-phenylpropan-1-amine (500 mg, 1.28 mmol) in 10 mL of THF was added under nitrogen 2.04 mL of freshly made benzoic acid (156 mg, 1.28 mmol). To this stirred solution was then added sequentially triphenylphosphine (335 mg, 1.28 mmol) and diisopropyl azodicarboxylate (DIAD, 258 mg, 1.28 mmol). The mixture was slowly allowed to warm to room temperature and then left stirred for two days. The excess benzoic acid was destroyed by slow addition of aqueous NaHCO$_3$. The aqueous phase was extracted with EtOAc (3×), organic layers were combined, and the combined organic layer was washed with water and brine, then dried (MgSO4). Filtering and evaporating the volatiles under reduced pressure left a crude that was purified by Flash chromatography (10% EtOAc/hexane) to furnish a mixture of the desired anti-N-Boc-protected benzoate ester (major) and the undesired syn-benzoate ester as a colorless gum. Yield of the mixture of anti- and syn-diastereomeric benzoate esters was 506 mg, 80%.

Separation of these diastereomers by Flash chromatography proved to be difficult at this stage, hence this mixture was directly taken to the saponification at which point the corresponding alcohols were readily separated by Flash chromatography. The saponification was carried out by heating the diastereomeric mixture at 60° C. with a solution of KOH (1.14 g, 20.35 mmol) in a 1:1 mixture of MeOH and water (10 ml) overnight. After standard work up with EtOAc, the diastereomeric alcohols (N-Boc-MCJ001-OH—RS and N-Boc-MCJ001-OH—SS) could readily be separated by Flash chromatography. Yield: major N-Boc-MCJ001-OH—RS 187 mg, 47%, minor N-Boc-MCJ001-OH—SS 136 mg, 34.3%). $^1$H NMR of N-Boc-MCJ001-OH—RS (CDCl$_3$) δ 7.85-7.03 (m, 12H), 4.97 (d, J=5.65 Hz, 1H), 4.41-4.24(m, 1H), 3.67-3.07 (m, 2H), 2.91 (s, 3H), 1.55 (s, 3H); MS: m/z (ESI) 414 (M+Na)$^+$.

Step 2: Preparation of N-Boc-MCJ001-N$_3$—SS by Mitsunobu reaction: To a cooled (0° C.) solution of N-Boc-(2S, 3R)-3-hydroxy-N-methyl-2-(naphthale2-yl)-3-phenylpropan-1-amine (30 mg, 0.077 mmol) in 1 mL of THF was added under nitrogen 0.153 mL of freshly made hydrazoic acid solution (ca. 2.5 M in benzene). To this stirred solution was then added sequentially triphenylphosphine (30 mg, 0.115 mmol) and diisopropyl azodicarboxylate (DIAD, 23 mg, 0.115 mmol). The mixture was slowly allowed to warm to room temperature and then left stirred for two days. The excess hydrazoic acid was destroyed by slow addition of aqueous NaHCO$_3$. The aqueous phase was extracted with EtOAc (3×), organic layers were combined, and the combined organic layer was washed with water and brine, then dried (MgSO4). Filtering and evaporating the volatiles under reduced pressure left a crude that was purified by Flash chromatography (10% EtOAc/hexane) to furnish the desired N-Boc-protected azide as colorless gum.

Step 3: Reduction of N-Boc-MCJ001-N$_3$—SS to MCJ002-NH$_2$—SS and MCJ001-Cyc-NH$_2$—SS. To a stirred solution of N-Boc-MCJ001-N$_3$—SS (89 mg, 0.214 mmol) in THF (10 mL) was slowly lithium aluminum hydride (65 mg, 1.71 mmol). The resulting mixture was refluxed overnight under nitrogen. After quenching with 10% NaOH, the aqueous phase was extracted with EtOAc (3×). The extracts were combined and washed with brine, and finally dried (Na$_2$SO$_4$). After filtration, the organic layer was concentrated using a rotary evaporator to give a crude that was purified by reverse phase HPLC (10% B-100% B in 30 minutes; B=80% aq. CH$_3$CN with 0.1% TFA, A=H$_2$O with 0.1% TFA), FR=8 mL/minute; λ$_{max}$=254 nm, RT=18.7 minutes (MS=305) and RT=24.0 minutes (MS=303)) to furnish the diamine (MS=305) and its cyclic analogue (MS=303) which were immediately converted to dihydrochloride salts. Yield of MCJ002-NH$_2$—SS 27 mg, 41.5%; yield of the $^1$H NMR for MCJ002-NH2-SS: (CD$_3$OD) δ 7.86-7.14 (m, 3H), 7.64 (s, 1H), 7.52-7.44 (m, 3H), 7.35-7.25 (m, 2H), 7.19-7.12(m, 3H), 4.76 (d, J=7.8 Hz, 1H), 4.13-4.00 (m, 1H), 3.76 (dd, 12.6, 3.6 Hz, 1H), 2.66 (s, 3H), 2.52 (s, 3H); MS: m/z (ESI) 305 (M+1)$^+$; [α]$_D^{20}$—11.4 (c 0.21, 9:1 EtOH:H$_2$O).

This reaction also gave a cyclized product, (4S,5S)-1-methyl-5-(naphthalen-2-yl)-4-phenylhexahydropyrimidine (MCJ001-Cyc-NH$_2$—SS: MS) which was also isolated by HPLC procedure as described above for MCJ001-NH$_2$—SS. Yield 28 mg, 43.3%. $^1$H NMR for MCJ001-Cyc-NH$_2$—SS: MS: (CD$_3$OD) δ 7.77-7.61 (m,3H), 7.51 (s, 1H), 7.48-7.39 (m,3H), 7.15 (s, 5H), 4.77 (d, J=10.4 Hz,1H), 4.26 (d, J=10.5 Hz, 1H), 4.15 (d, J=11.5 Hz, 1H), 3.83 (d, J=12.6 Hz, 1H), 3.78-3.66 (m, 1H), 3.30 (dd, J=12.6, 12.6 Hz, 1H), 2.81 (s, 3H), 2.55 (s, 1H); m/z (ESI) 303 (M+1)$^+$.

Example 22

Synthesis of (2S,2'S,3S,3'S)-3,3'-(butane-1,4-diylbis (oxy))bis(N-methyl-2-(naphthalen-2-yl)-3-phenyl-propan-1-amine)

To a solution of N-Boc-PRC-200 (39 mg, 0.10 mmol) dissolved in DMF (dry) cooled to 0° C. was added NaH (50% oil, 19 mg, 0.80 mmol) under nitrogen. The reaction mixture was set to stirring while 1,4-dibromobutane (22 mg, 0.10 mmol) was added drop wise, and the resulting reaction mixture was left stirred for 2 hours at room temperature. Upon completion of the reaction water (2 mL) was added, and the mixture was extracted with diethyl ether (3×15 mL). The combined extracts were washed with brine (15 mL), then dried over MgSO$_4$, filtered, and concentrated under reduced pressure. The crude product was purified by silica-gel column chromatography using 20% EtOAc/hexane as eluent. The pure product that was obtained as a colorless oil was then dissolved in 4N HCl-Dioxane (5 mL), and the resulting solution was stirred at room temperature under N$_2$ for 45 minutes. The solvent was evaporated under reduced pressure, and the residue was leached with diethyl ether to afford the title compound as gummy crude. The pure product MCJ001-dimer4-SS was isolated by reverse phase HPLC (0% B-100% B in 45 minutes (B=80% aq. CH$_3$CN with 0.1% TFA, A=H$_2$O with 0.1% aq.TFA); FR=8 mL/minute; $\lambda_{max}$=254 nm. RT=35.75 minutes). The product was converted to a hydrochloride salt. Yield 15 mg, 21.1%. $^1$H NMR: $^1$H NMR (MD$_3$OD) δ 1.65 (m, 4H), 2.68 (s, 6H), 3.19-3.31 (m, 4H), 3.36-3.59 (m, 4H), 3.75 (m, 2H), 4.58 (d, 2H, J=8.5 Hz), 7.06-7.12 (m, 10H), 7.23 (d, 2H, J=8.7 Hz), 7.42-7.45 (m, 4H), 7.57 (br s, 2H), 7.68-7.79 (m, 6H); MS: m/z (ESI) 637.07 (M+1)$^+$.

Example 23

Synthesis of (2S,2'S,3S,3'S)-3,3'-(pentane-1,5-diyl-bis(oxy))bis(N-methyl-2-(naphthalen-2-yl)-3-phenylpropan-1-amine)

To a solution of N-Boc-PRC-200 (100 mg, 0.255 mmol) dissolved in DMF (dry) cooled to 0° C. was added NaH (50% oil, 49 mg, 2.04 mmol) under nitrogen. The reaction mixture was set to stirring, while 1,4-dibromopentane (29 mg, 0.128 mmol) was added drop wise, and the resulting reaction mixture was left stirred for 2 hours at room temperature. Upon completion of the reaction water (2 mL) was added, and the mixture was extracted with diethyl ether (3×15 mL). The combined extracts were washed with brine (15 mL), then dried over MgSO$_4$, filtered, and concentrated under reduced pressure. The crude product was purified by silica-gel column chromatography using 20% EtOAc/hexane as eluent. The pure product that was obtained as a colorless oil was then dissolved in 4N HCl-Dioxane (5 mL), and the resulting solution was stirred at room temperature under N$_2$ for 45 minutes. The solvent was evaporated under reduced pressure, and the residue was leached with diethyl ether to afford the title compound as gummy crude. The pure product MCJ001-dimer4-SS was isolated by reverse phase HPLC (0% B-100% B in 50 min (B=80% aq. CH$_3$CN with 0.1% TFA, A=H$_2$O with 0.1% aq.TFA); FR=8 mL/minute; $\lambda_{max}$=254 nm. RT=38.57 minutes). The product was converted to a hydrochloride salt. Yield 44 mg, 23.8%. $^1$H NMR (MeOD) δ 1.33 (m, 2H), 1.56 (m, 4H), 2.66 (br s, 6H), 3.21-3.32 (m, 4H), 3.44 (m, 2H), 3.51 (m, 2H), 3.77 (dd, 2H, J=12.5, 5.9 Hz), 4.58 (d, 2H, J=8.8 Hz), 7.06-7.15 (m, 10H), 7.23 (dd, 2H, J=8.5, 1.6 Hz), 7.38-7.44 (m, 4H), 7.55 (br s, 2H), 7.64-7.77 (m, 6H); m/z (ESI) 651.27 (M+1)$^+$.

Example 24

Synthesis of (5S,6S)-3,3-dimethyl-5-(naphthalen-2-yl)-6-phenyl-1,3-oxazinan-3-ium chloride To a stirred solution of MCJ002-NH$_2$—SS.2HCl (Example 21, 11 mg, 0.036 mmol) dissolved in 1 mL of MeOH was added 36% aq. formaldehyde solution (0.2 mL). This solution was heated at 65° C. overnight. After rotary evaporation of the volatiles, the product was leached with diethyl ether and hexane, converted to a hydrochloride salt and then crystallized from anhydrous diethyl ether. Yield 10.1, 88%. $^1$H NMR (CD$_3$OD) δ 7.77-7.65 (m, 4H), 7.57 (s, 1H), 7.44-7.37 (m, 2H), 7.25-7.11 (m, 5H), 4.55 (d, J=9.4 Hz, 1H), 3.97-3.84 (m, 3H), 3.69-3.52 (m, 4H), 2.96 (s, 3H), 2.26 (s, 3H); MS: m/z (ESI) 317.18 M$^+$.

Example 25

(5S,6S)-5-(naphthalen-2-yl)-6-phenyl-1,3-oxazinane hydrochloride

To a stirred solution of PRC200.HCl (100 mg, 0.361 mmol) dissolved in 2 mL of MeOH was added 36% aq. formaldehyde solution (0.5 mL). This solution was heated at 65° C. overnight. After rotary evaporation of the volatiles, the product was leached with diethyl ether and hexane. The crude product could be purified by converting it to a hydrochloride salt, then crystallization from a solvent mixture prepared by dissolving 5 mL of MeOH, 20 mL of diethyl ether, and 17 mL of hexane. Yield 99 mg, 95%. $^1$H NMR (CD$_3$OD) δ 7.82-7.69 (m,4H), 7.63 (s, 1H), 7.48-7.39 (m,2H), 7.23 (d, J=8.1 Hz, 1H), 7.15 (s, 4H), 5.29 (d, J=9.1 Hz,1H), 5.09 (d, J=10.3 Hz, 1H), 5.02 (d, J=9.2 Hz, 1H), 3.87 (dd, J=12.2, 12.2 Hz, 1H), 3.75 (dd, J=13.0, 4.1 Hz, 1H), 3.71 (dd, J=4.1 Hz, 1H), 3.57-3.45 (m, 1H); MS: m/z (ESI) 290.11(M+1)$^+$; [α]$_D^{20}$+125 (c 0.22, 9:1 EtOH:H$_2$O).

Example 26

(5S,6S)-3-methyl-5-(naphthalen-2-yl)-6-phenyl-1,3-oxazinane hydrochloride

To a stirred solution of PRC200.HCl (Example 21, 50 mg, 0.172 mmol) dissolved in 1 mL of MeOH was added 36% aq. formaldehyde solution (0.5 mL). This solution was heated at 65° C. overnight. After rotary evaporation of the volatiles, the product was leached with diethyl ether and hexane. The pure product was isolated by reverse phase HPLC (Vydac 2.2×25 cm, C-18, elution with a gradient of 10% B-100% B in 30 minutes, B=80% aq. CH$_3$CN with 0.1% TFA, A=H$_2$O with 0.1% TFA); FR=8 mL/minute; $\lambda_{max}$=254 nm; RT=29.9 minutes). Evaporation of the solvent furnished the product as a gummy residue that gave a white solid after conversion to a hydrochloride salt. Alternatively, the crude product could be purified by converting it to a hydrochloride salt, then crystallization from a solvent mixture prepared by dissolving 4 mL of MeOH, 20 mL of diethyl ether, and 17 mL of hexane. Yield 49,9 mg, 96%. $^1$H NMR (CD$_3$OD) δ 7.85-7.68 (m,4H), 7.65 (s, 1H), 7.49-7.38 (m,2H), 7.25 (d, J=8.1 Hz, 1H), 7.15 (s, 4H), 5.28 (d, J=8.1 Hz,1H), 5.10 (d, J=10.2 Hz, 1H), 4.95 (d, J=8.4 Hz, 1H), 3.99-3.3.78 (m, 2H), 3.70-3.56 (m,2H), 2.96 (s, 3H); MS: m/z (ESI) 304.16 (M+1)$^+$; $[\alpha]_D^{20}$+133.8 (c 0.26, 9:1 EtOH:H$_2$O).

Example 27

(5R,6R)-3-methyl-5-(naphthalen-2-yl)-6-phenyl-1,3-oxazinane hydrochloride

To a stirred solution of PRC200.HCl (Example 21, 100 mg, 0.343 mmol) dissolved in 2 mL of MeOH was added 36% aq. formaldehyde solution (0.5 mL). This solution was heated at 65° C. overnight. After rotary evaporation of the volatiles, the product was leached with diethyl ether and hexane. The pure product was isolated first converting to a hydrochloride salt, then crystallizing the crude from a solvent mixture prepared by dissolving 4 mL of MeOH, 20 mL of diethyl ether, and 17 mL of hexane. Yield 104 mg, >99%. $^1$H NMR (CD$_3$OD) δ 7.81-7.70 (m,4H), 7.64 (s, 1H), 7.48-7.41 (m,2H), 7.23 (d, J=8.1 Hz, 1H), 7.15 (s, 4H), 5.29 (d, J=8.5 Hz,1H), 5.09 (d, J=8.6 Hz, 1H), 3.94-3.83 (m, 2H), 3.67-3.53 (m,2H), 2.97 (s, 3H); $[\alpha]_D^{20}$–133.43 (c 0.35, 9:1EtOH:H$_2$O); MS: m/z (ESI); MS: m/z (ESI) 304.16 (M+1)$^+$.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising (2S, 3S)-3-chloro-N-methyl-2-(naphthalen-2-yl)-3-phenylpropan-1-amine or a salt thereof.

2. The composition of claim 1, wherein said composition comprises a pharmaceutically acceptable carrier.

3. A composition comprising (2S, 3S)-3-fluoro-N-methyl-2-(naphthalen-2-yl)-3-phenylpropan-1-amine or a salt thereof.

4. The composition of claim 3, wherein said composition comprises a pharmaceutically acceptable carrier.

5. A composition comprising 3-azido-N-methyl-2-(naphthalen-2-yl)-3-phenylpropan-1-amine or a salt thereof.

6. The composition of claim 5, wherein said 3-azido-N-methyl-2-(naphthalen-2-yl)-3-phenylpropan-1-amine comprises (2R, 3R)-3-azido-N-methyl-2-(naphthalen-2-yl)-3-phenylpropan-1-amine or (2S, 3S)-3-azido-N-methyl-2-(naphthalen-2-yl)-3-phenylpropan-1-amine.

7. The composition of claim 5, wherein said 3-azido-N-methyl-2-(naphthalen-2-yl)-3-phenylpropan-1-amine comprises (2R, 3S)-3-azido-N-methyl-2-(naphthalen-2-yl)-3-phenylpropan-1-amine or (2S, 3R)-3-azido-N-methyl-2-(naphthalen-2-yl)-3-phenylpropan-1-amine.

8. The composition of claim 5, wherein said 3-azido-N-methyl-2-(naphthalen-2-yl)-3-phenylpropan-1-amine comprises:

(i) two compounds selected from the group consisting of (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine; or (ii) three compounds selected from the group consisting of (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine; or (iii) (2R, 3R)-3-azido-N-methyl-2-(naphthalen-2-yl)-3-phenylpropan-1-amine, (2S, 3S)-3-azido-N-methyl-2-(naphthalen-2-yl)-3-phenylpropan-1-amine, (2R, 3S)-3-azido-N-methyl-2-(naphthalen-2-yl)-3-phenylpropan-1-amine, and (2S, 3R)-3-azido-N-methyl-2-(naphthalen-2-yl)-3-phenylpropan-1-amine.

9. The composition of claim 5, wherein said composition comprises a pharmaceutically acceptable carrier.

* * * * *

UNITED STATES PATENT AND TRADEMARK OFFICE
CERTIFICATE OF CORRECTION

PATENT NO. : 8,440,724 B2
APPLICATION NO. : 12/812337
DATED : May 14, 2013
INVENTOR(S) : Elliott Richelson et al.

It is certified that error appears in the above-identified patent and that said Letters Patent is hereby corrected as shown below:

Title Page 2, Column 1, line 39, Other Publications, please delete "y1)" and insert --yl)--, therefor.

Title Page 2, Column 1, lines 56-57, Other Publications, please delete "Cultured" and insert --Cultured Cells of Nervous Tissue--, therefor.

Title Page 2, Column 1, line 58, Other Publications, please delete "Raven Cells of Nervous Tissue" and insert --Raven--, therefor.

Title Page 2, Column 2, Other Publications, please delete "PRCO25" and insert --PRC025--, therefor.

In the Specifications

Column 1, line 10, please delete "Jan. 1, 2009," and insert --Jan. 9, 2009,--, therefor.

Signed and Sealed this
Twentieth Day of August, 2013

Teresa Stanek Rea
*Acting Director of the United States Patent and Trademark Office*